United States Patent
Martínez Escribano et al.

(10) Patent No.: US 11,278,014 B2
(45) Date of Patent: Mar. 22, 2022

(54) **EXPRESSION OF RECOMBINANT PROTEINS IN *TRICHOPLUSIA NI* PUPAE**

(71) Applicant: Alternative Gene Expression, S.L., Madrid (ES)

(72) Inventors: José Ángel Martínez Escribano, Madrid (ES); Carmen Alvarado Fradua, Madrid (ES); Edel Reytor Saavedra, Madrid (ES); Miguel Cid Fernandez, Madrid (ES)

(73) Assignee: Alternative Gene Expression, S.L., Madrid (ES)

(*) Notice: Subject to any disclaimer, the term of this patent is extended or adjusted under 35 U.S.C. 154(b) by 605 days.

(21) Appl. No.: 15/761,055

(22) PCT Filed: Sep. 19, 2016

(86) PCT No.: PCT/EP2016/072143
§ 371 (c)(1),
(2) Date: Mar. 16, 2018

(87) PCT Pub. No.: WO2017/046415
PCT Pub. Date: Mar. 23, 2017

(65) Prior Publication Data
US 2020/0085022 A1    Mar. 19, 2020

(30) Foreign Application Priority Data
Sep. 17, 2015 (EP) ................................. 15382451

(51) Int. Cl.
| A01K 67/033 | (2006.01) |
| A61M 5/20 | (2006.01) |
| C12N 15/86 | (2006.01) |
| C12N 15/85 | (2006.01) |

(52) U.S. Cl.
CPC .......... *A01K 67/0339* (2013.01); *A61M 5/20* (2013.01); *C12N 15/8509* (2013.01); *C12N 15/86* (2013.01); *A01K 2227/706* (2013.01); *A01K 2267/02* (2013.01); *C12N 2710/14141* (2013.01); *C12N 2830/15* (2013.01)

(58) Field of Classification Search
None
See application file for complete search history.

(56) References Cited

U.S. PATENT DOCUMENTS

| 5,351,643 A * | 10/1994 | Hughes | A01K 67/033 119/6.5 |
| 2007/0067855 A1* | 3/2007 | Jarvis | C12N 15/8509 800/13 |
| 2011/0314562 A1 | 12/2011 | Lu et al. | |

FOREIGN PATENT DOCUMENTS

| CA | 2876343 A1 | 12/2012 |
| CA | 2893578 A1 | 6/2014 |
| CN | 102286533 A | 12/2011 |
| CN | 103960204 A | 8/2014 |
| CN | 104735977 A | 6/2015 |
| JP | H09-51742 A | 2/1997 |
| JP | 1997-215499 A | 8/1997 |
| JP | 2008/532518 A | 8/2008 |
| WO | 2012/168492 A2 | 12/2012 |
| WO | 2012/168493 A2 | 12/2012 |
| WO | 2014/086981 A1 | 6/2014 |

OTHER PUBLICATIONS

Capinera, John L. http://entnemdept.ufl.edu/creatures/veg/leaf/cabbage_looper.htm retrieved Nov. 6, 2020.*
Definition of "inoculate" https://www.merriam-webster.com/dictionary/inoculating retrieved May 17, 2021.*
Sasaki et al., "Silkworm expression of proteins by a BmNPV bacmid DNA system," *Protein Science Society of Japan Archives* 4:eQ63, 2011. (14 pages).
Burden et al., "Infectivity, Speed of Kill, and Productivity of a Baculovirus Expressing the Itch Mite Toxin Txp-1 in Second and Fourth Instar Larvae of *Trichoplusia ni*," *Journal of Invertebrate Pathology* 75:226-236, 2000.
Cha et al., "Expression of Green Fluorescent Protein in Insect Larvae and Its Application for Heterologous Protein Production," *Biotechnology and Bioengineering* 56(3):239-247, 1997.
Chazarra et al., "Purification and Kinetic Properties of Human Recombinant Dihydrofolate Reductase Produced in *Bombyx mori* Chrysalides," *Appl Biochem Biotechnol* 162:1834-1846, 2010.
Gomez-Casado et al., "Insect larvae biofactories as a platform for influenza vaccine production," *Protein Expression and Purification* 79:35-43, 2011.
Gómez-Sebastián et al., "Significant Productivity Improvement of the Baculovirus Expression Vector System by Engineering a Novel Expression Cassette," *PLoS ONE* 9(5):e96562, 2014, 10 pages.
Hellers et al., "Diapausing Pupae of *Hyalophora Cecropia*. An Alternative Host for Baculovirus Mediated Expression," *Insect Biochem. Molec. Biol.* 22(1):35-39, 1992.
Hellers et al., "Expression and post-translational processing of preprocecropin A using a baculovirus vector," *Eur. J. Biochem.* 199:435-439, 1991.
International Search Report and Written Opinion of the International Searching Authority, dated Nov. 13, 2017, for International Application No. PCT/EP2016/072143, 22 pages.
Invitrogen™, "Bac-to-Bac® Baculovirus Expression System," User Guide, Revision A.0, Aug. 13, 2015, 80 pages.
Invitrogen™, "Bac-to-Bac® TOPO® Expression System," User Manual, Version A, Dec. 15, 2008, 61 pages.

(Continued)

*Primary Examiner* — Oluwatosin A Ogunbiyi
(74) *Attorney, Agent, or Firm* — Seed Intellectual Property Law Group LLP

(57) ABSTRACT

The present invention covers means and methods to increase the efficiency of recombinant protein expression, in particular to optimize the industrial production of recombinant proteins in insect pupae, particularly in *Trichoplusia ni* (*T. ni*) pupae. Moreover, the present invention is also directed to the pupae itself comprising baculovirus, pupae infected, transformed, transduced or transfected with baculoviruses or bacmids, as well as devices suitable for performing the methods of the present invention.

19 Claims, 8 Drawing Sheets

Specification includes a Sequence Listing.

(56) References Cited

OTHER PUBLICATIONS

Jinn et al., "Aerosol Infectivity of a Baculovirus to *Trichoplusia ni* Larvae: An Alternative Larval Inoculation Strategy for Recombinant Protein Production," *Biotechnol. Prog.* 25(2):384-389, 2009.

Kulakosky et al., "N-Linked glycosylation of a baculovirus-expressed recombinant glycoprotein in insect larvae and tissue culture cells," *Glycobiology* 8(7):741-745, 1998.

Medin et al., "Efficient, low-cost protein factories: Expression of human adenosine deaminase in baculovirus-infected insect larvae," *Proc. Natl. Acad. Sci. USA* 87:2760-2764, 1990.

Mikhailov et al., "Protein synthesis in pupae of the silkworm *Bombyx mori* after infection with nuclear polyhedrosis virus: resistance to viral infection acquired during pupal period," *Journal of General Virology* 73:3195-3202, 1992.

Motohashi et al., "Efficient large-scale protein production of larvae and pupae of silkworm by *Bombyx mori* nuclear polyhedrosis virus bacmid system," *Biochemical and Biophysical Research Communications* 326:564-569, 2005.

NCBI Taxonomy Browser, "Autographa califomica nucleopolyhedrovirus," Taxonomy ID: 46015, downloaded on Apr. 5, 2016 from https://www.ncbi.nlm.nih.gov/Taxonomy/Browser/wwwtax.cgi?mode=Info&id=46015&lvl=3&p=mapview&p=has_linkout&p=blast_url&p=genome_blast&lin=f&keep=1&srchmode=1&unlock, 2 pages.

Nettleship et al., "Recent advances in the production of proteins in insect and mammalian cells for structural biology," *Journal of Structural Biology* 172:55-65, 2010.

Pérez-Filgueira et al., "Development of a low-cost, insect larvae-derived recombinant subunit vaccine against RHDV," *Virology* 364:422-430, 2007.

Pérez-Filgueira et al., "Optimization and Validation of Recombinant Serological Tests for African Swine Fever Diagnosis Based on Detection of the p30 Protein Produced in *Trichoplusia ni* Larvae," *Journal of Clinical Microbiology* 44(9):3114-3121, 2006.

Pérez-Martin et al., "Immunity conferred by an experimental vaccine based on the recombinant PCV2 Cap protein expressed in *Trichoplusia ni*-larvae," *Vaccine* 28:2340-2349, 2010.

Reis et al., "Antibody Production in Silkworm Cells and Silkworm Larvae Infected with a Dual Recombinant *Bombyx mori* Nuclear Polyhedrosis Virus," *Nature BioTechnology* 10:910-912, 1992.

Shafer et al., "Development and Validation of a Competitive Enzyme-linked Immunosorbent Assay for Detection of Type A Influenza Antibodies in Avian Sera," *Avian Diseases* 42:28-34, 1998.

Smith et al., "Production of Human Beta Interferon in Insect Cells Infected with a Baculovirus Expression Vector," *Molecular and Cellular Biology* 3(12):2156-2165, 1983.

Sumathy et al., "Expression of Human Growth Hormone in Silkworm Larvae through Recombinant *Bombyx mori* Nuclear Polyhedrosis Virus," *Protein Expression and Purification* 7:262-268, 1996.

Suzuki et al., "Efficient protein production using a *Bombyx mori* nuclear polyhedrosis virus lacking the cysteine proteinase gene," *Journal of General Virology* 78:3073-3080, 1997.

UniProt, "Taxonomy—Autographa californica nuclear polyhedrosis virus (AcMNPV)," Taxon identifier 46015, downloaded on Apr. 5, 2016 from https://www.uniprot.org/taxonomy/46015, 1 page.

Usami et al., "Comparison of recombinant protein expression in a baculovirus system in insect cells (Sf9) and silkworm," *J. Biochem.* 149(2):219-227, 2011.

Wang et al., "Cloning of Anti-LPS Factor cDNA from *Tachypleus tridentatus*, Expression in *Bombyx mori* Larvae and Its Biological Activity In Vitro," *Molecular Biotechnology* 21, 2002, 7 pages.

Wöltje et al., "Transgenic protein production in silkworm silk glands requires cathepsin and chitinase of *Autographa californica* multicapsid nucleopolyhedrovirus," *Appl Microbiol Biotechnol* 98:4571-4580, 2014.

Wu et al., "High-Level Expression of Human Acidic Fibroblast Growth Factor and Basic Fibroblast Growth Factor in Silkworm (*Bombyx mori* L.) Using Recombinant Baculovirus," *Protein Expression and Purification* 21:192-200, 2001.

Milks et al., "Serial Selection for Resistance to a Wild-Type and to a Genetically Modified Nucleopolyhedrovirus in *Trichoplusia ni*," *Biological Control* 19:283-289, 2000. (8 pages).

Andersons et al., "Biologically active and amidated cecropin produced in a baculovirus expression system from a fusion construct containing the antibody-binding part of protein A," *Biochem. J.* 280:219-224, 1991.

Carpenter et al., "Progress on Extraction of Codling Moth Pupae From Diet to Facilitate Handling, Shipping and Irradiation of Insects," Improvement of Codling Moth SIT to Facilitate Expansion of Field Application, *Proc. of the Second Research Co-ordination Meeting, FAO/IAEA Coordinated Research Program*, Stellenbosch, South Africa, Mar. 8-12, 2004, p. 119-124. (2 pages).

Dyck, "Rearing codling moth for the sterile insect technique," FAO Plant Production and Protection Paper 199, *Food and Agriculture Organization of the United Nations*, 2010. (195 pages).

Escribano et al., "Chrysalises as natural production units for recombinant subunit vaccines," *Journal of Biotechnology: X* 6(100019):1-7, 2020.

Shorey et al., "Mass-Rearing of the Larvae of Nine Noctuid Species on a Simple Artificial Medium," *Journal of Economic Entomology* 58(3):522-524, Jun. 1965.

Horrocks et al., "The silkmoth cocoon as humidity trap and waterproof barrier," *Comparative Biology and Physiology A*(164): 645-652, 2013.

Koizumi et al., "Potato *Phthorimaea operculella* ZE Zeller," *Research Bulletin of the Plant Protection Service Japan* 4:66-69, 1966.

Usami et al., "Comparison of recombinant protein expression in a baculovirus system in insect cells (Sf9) and wilkworm," *J. Biochem.* 149(2):219-227, 2011.

\* cited by examiner

| Bombyx mori | Trichoplusia ni |
|---|---|
|  |  |

Figure 18

[Bar chart: mg of porcine circovirus Cap A protein/L (cell culture or chrysalises extract), y-axis 0–1000]

- Conventional Bac. in Sf9 cells
- TopBac® in Sf9 cells
- TopBac® in pupae

Figure 19.

Pupae infection $5\times10^2 - 10^4$ PFU → Virus extraction → Centrifugation → Filtration → Freezing or lyophylization → Virus titration in larvae

Figure 20.

Frozen infected pupae → Infected pupae disruption by a homogenizer → Sonication → Centrifugation → Filtration through diatomaceous earth path → Tangential flow filtration → Chromatography purification

EXPRESSION OF RECOMBINANT PROTEINS IN *TRICHOPLUSIA NI* PUPAE

FIELD OF THE INVENTION

The present invention may be included in the field of biotechnology and it covers means and methods to increase the efficiency of recombinant protein expression, in particular for the industrial production of recombinant proteins in insect pupae, particularly in *Trichoplusia ni* (*T. ni*) pupae, including its optimization. Moreover, the present invention is also directed to the pupae itself comprising a baculovirus, pupae infected, transformed, transduced or transfected with baculoviruses or bacmids.

STATE OF THE ART

The baculovirus expression vector system (BEVS) is a well-established method for the production of recombinant proteins, for example proteins to be used as vaccines, therapeutic molecules or diagnostic reagents. With its potential for over-expression and rapid speed of development, the BEVS is one of the most attractive choices for producing recombinant proteins for any purpose. The most employed baculovirus vector used in industry for recombinant protein expression is based on *Autographa californica* multinuclear polyhedrosis virus (AcMNPV) with *Spodoptera frugiperda* 9 (Sf9) or 21 (Sf21) insect cells as suitable expression hosts (Nettleship, J. E., Assenberg, R., Diprose, J. M., Rahman-Hug, N., Owens, R. J. Recent advances in the production of proteins in insect and mammalian cells for structural biology. *J. Struct. Biol.* 2010, 172, 55-65), as well as *Trichoplusia ni* (*T. ni*) insect larvae as living biofactories (Gomez-Casado F, Gomez-Sebastian S, Núñez M C, Lasa-Covarrubias R, Martínez-Pulgarin S, Escribano J M. Insect larvae biofactories as a platform for influenza vaccine production. *Protein Expr Purif.* 79: 35-43. 2011). Since the BEVS was developed in the 80's (Smith, G. E., M. D. Summers, and M. J. Fraser. 1983. Production of human beta interferon in insect cells infected with a baculovirus expression vector. *Mol. Cell. Biol.* 3: 2156-21 65), hundreds of recombinant proteins, ranging from cytosolic enzymes to membrane-bound proteins, have been successfully produced in baculovirus-infected insect cells.

Recently, new baculovirus vectors have been described. For instance, WO 2012/168493 and WO 2012168492 describe recombinant DNA elements for the expression of recombinant proteins in insects and insect cells.

Worldwide, about 70,000 tons of silk are produced annually in a process that converts a low-value substrate, the leaves of the mulberry tree, to a high-value protein-based product: silk. Insects are highly efficacious protein producers because of their accelerated metabolism.

Lepidoptera such as *Bombyx mori* (*B. mori*, silkworm) or *T. ni* (cabbage looper), are two of the most used insects in biotechnology. They grow in size about 5000 times in less than 2 weeks and produce more than a kilometer of silk per *B. mori* insect. While a cell from a silk gland may produce about 80 µg protein/cell/day, the best mammalian cell culture systems produces only about 50 pg protein/cell/day.

Accordingly, insects as living biofactories constitute a promising alternative to insect cells, conventional fermentation technologies and also to plant-derived proteins because of the production versatility, scalability, automation possibilities, efficiency and speed of development. For example, insects as living biofactories avoid the necessity of bioreactors for the expression of proteins in, e.g., insect cells. Bioreactors are a technological and economical barrier to produce new and existing recombinant proteins, since they are inefficient, expensive, technologically complex (it takes several years to be built, are hard to validate, need highly qualified personal to their manipulation, they are prone to contaminations and are not reliable). In addition, they face the problem of limited scalability.

Larvae of *B. mori* have been widely used as living biofactories for the expression of recombinant proteins using the baculovirus expression vector system (Wang, D N; Liu, J W; Yang, G Z; Zhang, W J; Wu, X F. 2002. Cloning of anti-LPS factor cDNA from *Tachypleus tridentatus*, expression in *Bombyx mori* larvae and its biological activity in vitro. *Molecular Biotechnology*, 21(1). 1-7; Wu, X F; Kamei, K; Sato, H; Sato, S; Takano, R; Ichida, M; Mori, H; Hara, S. 2001. High-level expression of human acidic fibroblast growth factor and basic fibroblast growth factor in silkworm (*Bombyx mori* L.) using recombinant baculovirus. *Protein Expression And Purification*, 21(1), 192-200; Kulakosky, P C; Hughes, P R; Wood, H A. 1998. N-linked glycosylation of a baculovirus-expressed recombinant glycoprotein in insect larvae and tissue culture cells. *Glycobiology*, 8(7), 741-745; Suzuki, T; Kanaya, T; Okazaki, H; Ogawa, K; Usami, A; Watanabe, H; KadonoOkuda, K; Yamakawa, M; Sato, H; Mori, H; Takahashi, S; Oda, K. 1997. Efficient protein production using a *Bombyx mori* nuclear polyhedrosis virus lacking the cysteine proteinase gene. *Journal Of General Virology*, 78, 3073-3080; Sumathy, S; Palhan, V B; Gopinathan, K P. 1996. Expression of human growth hormone in silkworm larvae through recombinant *Bombyx mori* nuclear polyhedrosis virus. *Protein Expression And Purification*, 7(3), 262-268; U. Reis, B. Blum, B. U. von Specht, H. Domdey, J. Collins, Antibody production in silkworm cells and silkworm larvae infected with a dual recombinant *Bombyx mori* nuclear polyhedrosis virus, *Biotechnology* (NY) 10 (1992) 910-912).

Larvae of *T. ni* have also been used for the expression of recombinant proteins (Perez-Martin, E., Gomez-Sebastian, S., Argilaguet, J. M., Sibila, M., Fort, M., Nofrarias, M., Kurtz, S., Escribano, J. M., Segales, J., Rodriguez, F., 2010. Immunity conferred by an experimental vaccine based on the recombinant PCV2 Cap protein expressed in *Trichoplusia ni*-larvae. *Vaccine* 28 (11), 2340-2349); Gomez-Casado E, Gomez-Sebastian S, Náñez M C, Lasa-Covarrubias R, Martínez-Pulgarin S, Escribano J M. Insect larvae biofactories as a platform for influenza vaccine production, *Protein Expr. Purif* 2011, 79: 35-43; Medin, J A; Hunt, L; Gathy, K; Evans, R K; Coleman, M S. 1990, Efficient, low-cost protein factories—expression of human adenosine-deaminase in baculovirus-infected insect larvae. *Proceedings of the National Academy of Sciences of the United States of America*, 87(7), 2760-2764; Shafer, A L; Katz, J B; Eernisse, K A. 1998. Development and validation of a competitive enzyme-linked immunosorbent assay for detection of type A influenza antibodies in avian sera. *Avian Diseases*, 42(1), 28-34; Cha, H J; Pham, M Q; Rao, G; Bentley, W E. 1997. Expression of green fluorescent protein in insect larvae and its application for heterologous protein production. *Biotechnology and Bioengineering*, 56(3), 239-247; Burden, J P; Hails, R S; Windass, J D; Suner, M M; Cory, J S. 2000. Infectivity, speed of kill, and productivity of a baculovirus expressing the itch mite toxin txp-1 in second and fourth instar larvae of *Trichoplusia ni*. *Journal of Invertebrate Pathology*, 75(3), 226-236; Perez-Filgueira, D. M.; Resino-Talavan, P.; Cubillos, C.; Angulo, L; Barderas, M. G.; Barcena, J.; Escribano, J. M., 2007. Development of a low-cost, insect larvae-derived recombinant subunit vaccine against RHDV. *Virology*, 364(2), 422-430; Perez-Filgueira, D. A.; Gonzalez-Camacho, F.; Gallardo, C.; Resino-Talavan, P.; Blanco, E.; Gomez-Casado, E.; Alonso, C.; Escribano, J. M., 2006. Optimization and validation of recombinant serological tests for African swine fever diagnosis based on detection of the p30 protein produced in *Trichoplusia ni* larvae. *Journal of Clinical Microbiology*, 44(9), 3114-3121; Hellers, M; Gunne, H; Steiner, H. 1991. Expression and posttranslational processing of preprocecropin-a using a baculovirus vector. *European Journal of Biochemistry*, 199 (2), 435-439).

In silkworm, comparative studies demonstrated that, for most proteins, the highest expression yields were obtained in larvae instead pupae (Akihiro Usami et al (Akihiro Usami, Seiji Ishiyama, Chiaki Enomoto, Hironobu Okazaki, Keiko Higuchi, Mashahiro Ikeda, Takeshi Yamamoto, Mutsumi Sugai, Yukiko Ishikawa, Yumiko Hosaka, Teruyuki Koyama, Yoneko Tobita, Syoko Ebihara, Toshiko Mochizuki, Yoshimi Asano and Hidekazu Nagaya, Comparison of recombinant protein expression in a baculovirus system in insect cells (Sf9) and silkworm, *J. Biochem.* 2011; 149(2): 219-227; Chazarra S, Aznar-Cervantes S, Sánchez-del-Campo L, Cabezas-Herrera J, Xiaofeng W, Cenis J L, Rodríguez-López J N, Purification and kinetic properties of human recombinant dihydrofolate reductase produced in *Bombyx mori* chrysalides, *Appl Biochem Biotechnol*. 2010 November; 162(7):1834-46). Also, a susceptibility decrease of pupae to baculovirus infection in Silkworm related with the age of pupae has been described (*Journal of General Virology* (1992), 73, 3195-320). In addition, in larvae, the infection of the baculovirus is generally performed orally, instead by inoculation (injection) for the scale up production. Pupae cannot be orally infected, so they have to be injected manually, which is tedious and time consuming. In addition, silkworm pupae are covered by a thick cocoon which has to be (manually) removed before the inoculation of the virus takes place, which is generally a tedious process.

Together with the general lower protein expression yield in silkworm pupa and the difficulties in its manipulation, have led to a general preference for the use of larvae for the production of recombinant proteins.

Similar disadvantages can be found in other systems, such as *Hyalophora cecropia* pupae. The expression of certain proteins in *H. cecropia* pupae is lower than in *T. ni* larvae (Hellers, M. and Steiner, H.; Insect Biochem. Molec. Biol., Vol 22, Bo. 1, pp. 35-39, 1992). In addition, *Hyalophora cecropia* moths are difficult to rear, are strictly univoltine (they have one generation per year), they have very low quantities of eggs per cycle and they have a high density cocoon (the thick cocoon has to be (manually) removed before the inoculation of the virus takes place, which is generally a tedious process). All these disadvantages make *Hyalophora cecropia* pupae a poor system for the expression of recombinant proteins, in particular a poor efficient, scalable and automatized system for the expression of recombinant proteins.

There is a need of more efficient and easy to automatize (scale up) systems for the expression of recombinant proteins in insects using the BEVS, particularly for the industrial expression of recombinant proteins in insects using the BEVS.

After intensive research, the inventors of the present invention have found a solution to the above problem, namely a protein expression system in pupae belonging to the Lepidoptera order, more preferably belonging to the species *Trichoplusia ni*, which is more efficient that the expression in larvae and moreover allows for an almost complete automation (scale up), which increases the efficiency and reduces costs associated to recombinant protein expression, in particular at industrial scale.

The present invention is thus directed to the use of pupae (chrysalises), preferably belonging to the Lepidoptera order, more preferably belonging to the species *Trichoplusia ni*, in combination with baculovirus vectors derived from *Autographa californica* multicapsid nucleopolyhedrovirus (AcMNPV), to produce recombinant proteins to be used in diagnostic, vaccines and therapeutic treatments. The use of pupae (chrysalises) from the species of *Trichoplusia ni* for recombinant protein expression, in particular the industrial use of pupae (chrysalises) from the species of *Trichoplusia ni* for recombinant protein expression has not yet been reported.

SUMMARY OF THE INVENTION

The present invention provides a pupa comprising a recombinant baculovirus and/or a transfer vector/bacmid derived from *Autographa californica* multicapsid nucleopolyhedrovirus (AcMNPV).

In addition, the present invention provides a pupa comprising a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein.

The invention also relates to the use of the pupa of the invention for the expression of recombinant proteins.

Further, the present invention provides a method for producing at least one recombinant protein comprising the steps of:
(a) Providing a pupa;
(b) Inoculating the pupa of step (a) with a recombinant baculovirus derived from *Autographa californica* multicapsid nucleopolyhedrovirus (AcMNPV);
(c) Incubating the inoculated pupa of step (b) for a period of time sufficient for the at least one recombinant protein to be expressed;
(d) Obtaining the pupae comprising the at least one recombinant protein;
(e) Optionally, harvesting the at least one recombinant protein; and
(f) Optionally, purifying the at least one recombinant protein.

In addition, provided herein is a method that can be automated to reduce manipulation for producing a silk-free pupa belonging to the order Lepidoptera comprising the steps of:
(a) Providing a pupa contained in a cocoon;
(b) Treating the pupa contained in a cocoon, preferably by a specially designed device, with a solution of a salt of hypochlorous acid, preferably sodium hypochlorite; and
(c) Obtaining a silk-free (and, optionally, essentially externally disinfected) pupa.

A method for producing a recombinant baculovirus comprising the steps of:
(a) Providing a pupa;
(b) Transfecting the pupa of step (a) with a transfer vector/bacmid suitable for producing a recombinant baculovirus derived from *Autographa californica* multicapsid nucleopolyhedrovirus (AcMNPV);

(c) Incubating the inoculated pupa of step (b) for a period of time sufficient for the recombinant baculovirus is produced;

(d) Obtaining the pupae comprising the recombinant baculovirus;

(e) Optionally, harvesting the recombinant baculovirus; and (f) Optionally, purifying the recombinant baculovirus, The present invention also relates to a device comprising a precision pump, a mobile mechanic arm and a (removable) needle/s suitable for injecting a fluid into a pupa belonging to the order Lepidoptera, preferably to the genera *Trichoplusia*, *Rachiplusia*, *Spodoptera*, *Heliothis*, *Manduca*, *Helicoverpa*, *Ascalapha* or *Samia*, more preferably to the genus *Trichoplusia*, *Rachiplusia*, *Spodoptera*, *Heliothis* or *Helicoverpa*, even more preferably to the species *Trichoplusia ni*, *Rachiplusia nu*, *Spodoptera frugiperda*, *Heliothis virescens*, *Helicoverpa armigera*, *Helicoverpa Zea*, *Manduca sexta*, *Ascalapha odorata* or *Samia cynthia*.

BRIEF DESCRIPTION OF THE FIGURES

FIG. 18: Comparison of Porcine circovirus Cap protein expression yields in insect cells by using a conventional baculovirus and a baculovirus modified by TopBac in insect cells and in insect pupae.

FIG. 19: Schematic example of procedure to obtain a virus inoculum from infected pupae.

FIG. 20: Schematic example of downstream processing procedure to obtain a purified recombinant protein from infected pupae.

DETAILED DESCRIPTION OF THE INVENTION

Definitions

Figure 1:
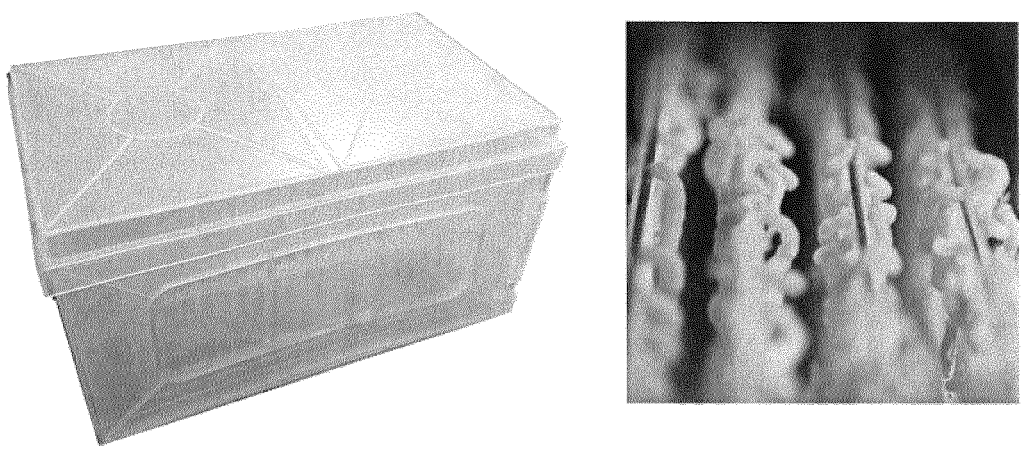
FIG. 1: Massive single-use *T. ni* insect rearing module. Fifth instar stage larvae growing in the insect rearing module.

As used herein, "pupa" refers to the life stage of some insects undergoing transformation. The pupal stage is found in insects that undergo a complete metamorphosis (holometabolous insects). These insects go through four life stages: embryo, larva, pupa and imago. The pupa of butterflies is also called chrysalis. Insects may protect the pupa covering them with a cocoon, which is a casing spun of silk which protects the pupa of many insects.

As used herein, "baculovirus" refers to a family of infectious viruses for invertebrates, mainly infecting insects and arthropods. A "recombinant baculovirus" has further introduced recombinant DNA through, for example, homologous recombination or transposition. The recombinant baculovirus may originate from *Autographa californica* multicapsid nucleopolyhedrovirus (AcMNPV).

As used herein, an "expression cassette" comprises recombinant DNA elements that are involved in the expression of a certain gene, such as the gene itself and/or elements that control the expression of this gene (e.g. the promoter). For example, an expression cassette useful in the present invention comprises the following recombinant DNA elements:
1. a nucleic acid sequence that allows expression of a recombinant protein, such as the recombinant proteins described below in the present specification, and preferably nucleic acid sequences controlling its expression (at least a promoter); and
2. a nucleic acid sequence that allows expression of baculovirus transcriptional regulators, such as IE-1 and IE-0, above the normal, i.e. endogenous, levels of said regulators that are obtained during baculovirus infection of an insect cell or an insect.

In some embodiments, the expression cassette further comprises an enhancer homologous region (hr), such as hr1, operably linked to the promoter of said sequence encoding the recombinant protein. The recombinant DNA elements forming part of the expression cassette of the invention may be present in a single nucleic acid molecule. The recombinant DNA elements forming part of the expression cassette may be present in distinct nucleic acid molecules. Preferably, the distinct nucleic acid molecules are present within the same cell.

As used herein, "recombinant DNA" refers to a form of artificial DNA that is engineered through the combination or insertion of one or more DNA strands, thereby combining DNA that would normally not occur together.

As used herein, "recombinant DNA element" refers to a functional element within recombinant DNA, such as a promoter, enhancer or a gene.

As used herein, "transcriptional regulator" refers to a regulatory protein that has the ability to modulate the transcription of specific genes by, for example, binding to enhancer or repressor regions and/or recruiting further proteins that are involved in transcription. IE-1 and its splice variant IE-0 are transcriptional regulators that are endogenously expressed during baculovirus infection. The expression level of the proteins IE-1, IE-0 and/or fragments thereof may be determined at both the mRNA and at the protein level with methods conventionally known to the person skilled in the art, such as quantitative PCR and Western Blot analysis.

According to the present invention, IE-1, IE-0 and/or fragments thereof may be recombinantly expressed to increase the total level of these proteins above endogenous levels during baculovirus infection. This can be achieved through, for example, introducing further copies of the endogenous gene or manipulating the expression of the promoter of the endogenous gene. Further copies of the endogenous genes can be introduced as transgenes under the control of a suitable promoter such as polh or pB2$_9$.

IE-1, IE-0 and fragments thereof may be encoded by the nucleic acids of SEQ ID NO: 1 (also referred to as Ac-ie-01) to SEQ ID NO: 5. SEQ ID NO: 1 is the Ac-ie-01 cDNA that encodes both IE-1 and IE-0, SEQ ID NO: 2 is the coding sequence (CDS) of IE-1 and SEQ ID NO: 3 is the CDS of IE-0. SEQ ID NO: 4 and 5 are the CDSs of the N-terminal domains of IE-1 and IE-0 respectively that retain the catalytic transcriptional regulator activity. The proteins that are encoded by SEQ ID NOs: 2-5 are represented by SEQ ID NOs: 6-9 respectively.

Nucleic and amino acid sequences referred to in the present invention shall be distinguished from other nucleic and amino acid sequences by their degree of sequence identity or similarity respectively as determined using EMBOSS Needle with the default parameters (http://www.ebi.ac.uk/Tools/psa/emboss_needle/). Methods for the generation of such variants include random or site directed mutagenesis, site-saturation mutagenesis, PCR-based fragment assembly, DNA shuffling, homologous recombination in vitro or in vivo, and methods of gene-synthesis.

As used herein, "variants" are nucleic or amino acids whose nucleic or amino acid sequence differs in one or more positions from the parental nucleic or amino acid sequence, whereby differences might be additions, deletions and/or substitutions of nucleic acids or amino acid residues.

As used herein, "homologous regions", (hr), are comprised of repeated units of about 70-bp with an imperfect 30-bp palindrome near their center. For instance, homologous regions are repeated at eight locations in the AcMNPV genome with 2 to 8 repeats at each side. Homologous regions have been implicated as both transcriptional enhancers and origins of baculovirus DNA replication.

As used herein, "enhancer region" refers to a control sequence, whose binding by transcriptional regulators increases the level of transcription of associated genes.

As used herein, "recombinant protein" refers to a protein that originates from recombinant DNA. Such proteins can be used for the benefit of humans and animals and may have industrial, commercial or therapeutic application.

As used herein, "being operably linked" refers to two nucleic acid sequences that are connected in a way that one influences the other in terms of, for example, transcriptional regulation.

As used herein, "promoter" refers to a DNA sequence to which RNA polymerase can bind to initiate transcription. The sequence may further contain binding sites for various proteins that regulate transcription, such as transcription factors. The promoter sequence may be composed of different promoter fragments (either different or the same fragments) that are localized closely in the DNA sequence and may be separated by linkers or spacer. Such promoters are referred to as chimeric promoters.

As used herein, a "transfer vector" is a vector (namely a DNA molecule used as a vehicle to carry genetic material) that permits the insertion of genetic information into a baculovirus genome.

As used herein, a "bacmid" refers to a plasmid construct which contains the DNA sequence sufficient for generating a baculovirus when transfected into a cell or insect.

As used herein, a "cloning vector" refers to any vector that is suitable for cloning, which generally involves the presence of restriction sites, an origin of replication for bacterial propagation and a selectable marker.

The cloning vector which may be used in the context of the present invention preferably contains in addition to (i) the sequence for expression above endogenous levels of the proteins IE-0, IE-1 and/or fragments thereof, (ii) a recombinant homologous region (hr) linked to (iii) a suitable promoter for driving the expression of a recombinant protein. For example, the cloning vector may comprise a nucleic acid sequence encoding a recombinant protein (also referred to as a "donor vector", namely a cloning vector comprising an expression cassette). Alternatively, the cloning vector lacks such sequence.

As used herein, a "vaccine" may be defined as a biological preparation, preferably comprising a recombinant protein that provides active acquired immunity to a particular disease.

As used herein, the term "about" means the indicated value ±1% of its value, or the term "about" means the indicated value ±2% of its value, or the term "about" means the indicated value ±5% of its value, the term "about" means the indicated value ±10% of its value, or the term "about" means the indicated value ±20% of its value, or the term "about" means the indicated value ±30% of its value; preferably the term "about" means exactly the indicated value (±0%).

DETAILED DESCRIPTION

The present invention provides a pupa comprising a recombinant baculovirus and/or a transfer vector/bacmid. The present invention surprisingly shows that introduction into insect pupae recombinant baculoviruses, and particularly of sequences that cause the expression of baculovirus transcriptional regulators above endogenous levels and optionally the introduction of an enhancer homologous region (hr) sequence, a promoter or a combination of promoters, is able to increase the production of a recombinant protein to unprecedented levels. This indicates the usefulness of this system for the expression of recombinant proteins in vivo, in particular for the industrial production of recombinant proteins in vivo.

Pupa of the Present Invention

The present invention provides a pupa comprising a recombinant baculovirus and/or a transfer vector and/or bacmid. The recombinant baculovirus and/or transfer vector and/or bacmid is preferably derived from *Autographa californica* multicapsid nucleopolyhedrovirus (AcMNPV). Preferably, the pupa belongs to the order Lepidoptera, preferably to the genus *Trichoplusia, Rachiplusia, Spodoptera, Heliothis, Manduca, Helicoverpa, Ascalapha* or *Samia*, preferably to the genus *Trichoplusia, Rachiplusia, Spodoptera, Heliothis* or *Helicoverpa*, more preferably to the species *Trichoplusia ni, Rachiplusiu nu, Spodoptera frugiperda, Heliothis virescens, Helicoverpa armigera, Helicoverpa Zea, Manduca sexta, Ascalapha odorata* or *Samia Cynthia*. Even more preferably, the pupa belongs to the species *Trichoplusia ni*. In a preferred embodiment, the pupa of the present invention does not belong to the species *Bombyx mori*. In a preferred embodiment, the pupa of the present invention does not belong to the species *Hyalophora cecropia*.

In a preferred embodiment, the pupa of the invention is a pupa belonging to the genera *Trichoplusia*, preferably to the species *Trichoplusia ni*, which comprises a recombinant baculovirus and/or a transfer vector/bacmid derived from *Autographa californica* multicapsid nucleopolyhedrovirus (AcMNPV).

The pupae of the invention, and in particular the pupae of *T. ni*, offer several advantages for the expression of recombinant proteins, in particular in automatized and scalable processes. For example, a moth couple of *T. ni* may have around 1.000 eggs per cycle. In addition, the cocoon produced by *T. ni* pupae is not as thick as the cocoon which covers the pupae of other species (such as, for example, *Bombyx mori* or *Hyalophora cecropia*), which makes the pupae of *T. ni* especially suited for their use in automatized and scalable production processes (industrial production of recombinant proteins). Accordingly, pupae of *T. ni* infected with a recombinant baculovirus and/or a transfer vector and/or a bacmid preferably derived from *Autographa californica* multicapsid nucleopolyhedrovirus (AcMNPV) provides for an efficient, scalable and easily automatized system for recombinant protein production. Further advantages of this system are its high productivity (up to 20 times more productive than bioreactors), the fact that it is technically simple, easy to implement and validate, its reduced costs (>90% of reduction in fixed investments with respect to the use of bioreactors), the lower cost of goods, short development times (baculovirus system), its high efficiency with proteins difficult to produce, and the high quality and safety of the produced products.

The inventors of the present application surprisingly found that the expression of recombinant proteins in pupae, in particular in pupae belonging to the order Lepidoptera, preferably to the genus *Trichoplusia, Rachiplusia, Spodoptera, Heliothis, Manduca, Helicoverpa, Ascalapha* or *Samia*, preferably to the genus *Trichoplusia, Rachiplusia, Spodoptera, Heliothis* or *Helicoverpa*, more preferably to the species *Trichoplusia ni, Rachiplusia nu, Spodoptera frugiperda, Heliothis virescens, Helicoverpa armigera, Helicoverpa Zea, Manduca sexta, Ascalapha odorata* or *Samia Cynthia*, is comparable to and even higher than the expression in larvae.

The patent application published as WO 2012/168492 discloses recombinant baculovirus and transfer vectors and bacmids that may be comprised in the pupa of the present invention.

The recombinant baculovirus and/or transfer vector and/or bacmid comprised in the pupa according to the present invention may preferably comprise a recombinant DNA. For example, the recombinant baculovirus and/or transfer vector and/or bacmid comprised in the pupa according to the present invention comprises a nucleic acid sequence encoding a recombinant protein, wherein the recombinant protein is preferably selected from the group consisting of subunit monomeric vaccine, subunit multimeric vaccine, virus like particle, therapeutic protein, antibody, enzyme, cytokine, blood clotting factor, anticoagulant, receptor, hormone, diagnostic protein reagents and the green fluorescent protein (GFP), and/or wherein the recombinant protein is preferably not a protein which is endogenously produced by pupae, as it will be described below. For example, the recombinant baculovirus and/or transfer vector and/or bacmid comprised in the pupa according to the present invention comprises a nucleic acid sequence that allows for the expression above endogenous levels of the proteins IE-1, IE-0 and/or fragments thereof functioning as transcriptional regulators above endogenous levels obtained during baculovirus infection (for example, the expression above endogenous levels may be obtained by the presence, in the recombinant baculovirus, of an additional copy of the nucleic acid sequence that allows for the expression of the proteins IE-1, IE-0 and/or fragments thereof). Preferably, the recombinant baculovirus and/or transfer vector and/or bacmid comprised in the pupa according to the present invention further comprises a recombinant homologous region (hr) operably linked to any promoter suitable for driving the expression of a recombinant protein.

The transfer vector which may be comprised in the pupa of the present invention preferably contains in addition to (i) the sequence for expression above endogenous levels of the proteins IE-0, IE-1 and/or fragments thereof, (ii) a recombinant homologous region (hr) linked to (iii) a suitable promoter for driving the expression of a recombinant, protein. In one preferred aspect, the transfer vector comprises a nucleic acid sequence encoding said recombinant protein, whereas in another preferred embodiment the transfer vector lacks such sequence. In a preferred embodiment, the transfer vector is a bacmid.

The transfer vector and/or bacmid may be derived from any of the commercially available baculovirus expression systems "Bac-to-Bac®" (Invitrogen™), "BacPAK™" (Clontech™), "FlashBAC™" (Oxford Expression Technologies™), "BactiVance™" (GenScript™), "Bac-N-Blue DNA™" (Invitrogen™), "BaculoDirect™" (Invitrogen™), "BacVector®" 1000, 2000, 3000 (Novagen®). "Diamond Bac™" (Sigma-Aldrich®) or "BaculoGold™" (BD Biosciences™).

The pupa of the present invention (which preferably belongs to the order Lepidoptera, preferably to the genus *Trichoplusia, Rachiplusia, Spodoptera, Heliothis, Manduca, Helicoverpa, Ascalapha* or *Samia*, preferably to the genus *Trichoplusia, Rachiplusia, Spodoptera, Heliothis* or *Helicoverpa*, more preferably to the species *Trichoplusia ni, Rachiplusia nu, Spodoptera frugiperda, Heliothis virescens, Helicoverpa armigera, Helicoverpa Zea, Manduca sexta, Ascalapha odorata* or *Samia cynthia*, or any other Lepidoptera susceptible to AcMNPV infection, even more preferably to the genus *Trichoplusia* and to the species *Trichoplusia ni*) may comprise a nucleic acid sequence that allows for the expression above endogenous levels of the proteins IE-1, IE-0 and/or fragments thereof functioning as transcriptional regulators above endogenous levels obtained during baculovirus infection. The above described recombinant DNA elements are preferably introduced into the pupa by a recombinant baculovirus.

The nucleic acid sequence that allows for the expression of the proteins IE-1, IE-0 and/or fragments thereof functioning as transcriptional regulators above endogenous levels obtained during baculovirus infection according to the present invention is preferably selected from the group consisting of:

(a) a nucleic acid containing the nucleotide sequence indicated in any of SEQ ID NOs: 1-5;

(b) a nucleic acid sequence having a sequence identity of at least 70%, preferably at least 75%, more preferably at least 80%, more preferably at least 85%, more preferably at least 90% and most preferably at least 95% with the nucleotide sequence indicated in any of SEQ ID NOs: 1-5 and encoding a protein able to function as a transcriptional regulator in a recombinant baculovirus;

(c) a nucleic acid sequence encoding an amino acid containing the amino acid sequence indicated in any of SEQ ID NOs: 6-9; and (d) a nucleic acid sequence encoding an amino acid sequence having a sequence similarity of at least 70%, preferably at least 75%, more preferably at least 80%, more preferably at least 85%, more preferably at least 90% and most preferably at least 95% with the amino acid sequence indicated in any of SEQ ID NOs: 6-9 and able to function as a transcriptional regulator in a recombinant baculovirus.

The sequence of the variants of SEQ ID NOs: 1-5 is at least 70%, preferably at least 75%, more preferably at least 80%, more preferably at least 85%, more preferably at least 90% and most preferably at least 95% identical to the sequences of SEQ ID NOs: 1-5.

The sequence of the variants of SEQ ID NOs: 6-9 is at least 70%, preferably at least 75%, more preferably at least 80%, more preferably at least 85%, more preferably at least 90% and most preferably at least 95% similar to the sequences of SEQ ID NOs: 6-9.

The pupa of the present invention may further comprise a nucleic acid sequence and/or recombinant baculovirus and/or a transfer vector and/or bacmid which further comprises a recombinant homologous region (hr) operably linked to any promoter that is suitable for driving the expression of a recombinant protein.

The recombinant homologous region (hr) is preferably the sequence indicated in SEQ ID NO: 21 (hr1).

The promoter that drives the expression of said recombinant protein is preferably selected from the group of nucleic acids comprising:

(a) a nucleic acid containing the nucleotide sequence indicated in any of SEQ ID NOs: 10-14, preferably indicated in any of SEQ ID NOs: 11-13; and (b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NOs: 10-14, preferably indicated in any of SEQ ID NOs: 11-13.

In a preferred embodiment, the nucleic acid sequence that comprises combinations of recombinant promoters, sequences encoding transcriptional regulators and enhancer regions (the nucleic acid sequences that are comprised in the pupa of the present invention) are selected from the group consisting of SEQ ID NOs: 15-20.

The recombinant promoters, sequences encoding transcriptional regulators and enhancer regions of the present invention do not need to form part of a single molecule, instead these sequences may form part of distinct molecules as long as they are operably linked, i.e. contained within the same cells within the pupa.

The pupa of the present invention and/or the recombinant baculovirus and/or transfer vector and/or bacmid may further comprise a nucleic acid sequence encoding a recombinant protein. This nucleic acid sequence is preferably operably linked to the nucleic acid sequence that allows for the expression above endogenous levels of the proteins IE-1, IE-0 and/or fragments thereof, and optionally to a homologous region (hr), these sequences having being described above.

Preferably, the recombinant protein is selected from the group consisting of subunit monomeric vaccine, subunit multimeric vaccine, virus like particle, therapeutic protein, antibody, enzyme, cytokine, blood clotting factor, anticoagulant, receptor, hormone, diagnostic protein reagents and green fluorescent protein (GFP).

In a preferred embodiment, the recombinant protein is a virus-like particle protein, which is preferably selected from the group consisting of:

(a) Porcine circovirus capsid protein, preferably from porcine circovirus type 2 (e.g., SEQ ID NO.: 26),
(b) Foot and mouth disease virus VP1, VP3 or VP0 protein,
(c) Canine parvovirus VP1 and VP2 proteins,
(d) Porcine parvovirus VP1 and VP2 proteins,
(e) Human norovirus (genogroup I or II) capsid protein,
(f) Calicivirus capsid protein,
(g) Human papillomavirus L1 protein, preferably from human papillonavirus 16,
(h) Hepatitis E protein E2,
(i) Infectious bursal disease virus VP1, VP2 and VP3 proteins,
(j) Astrovirus ORF2-encoded proteins,
(k) Influenza virus HA (e.g., SEQ ID NO.: 30), NA and M1 proteins,
(l) Hepatitis B core and surface antigens,
(m) Rabbit calicivirus VP60 protein, preferably from rabbit haemorrhagic disease viruses RHDVb and RHDVG1 (e.g., SEQ ID NOs.: 32 and 33).
(n) Human parvovirus VP1 and VP2 proteins For instance, the recombinant protein may be:

Porcine circovirus capsid protein, preferably from porcine circovirus type 2, which is, for example, represented by the amino acid sequence of SEQ ID NO: 26 or encoded by the nucleic acid sequence of SEQ ID NO: 25.

Foot and mouth disease virus (FMDV) VP1, VP3 and VP0 protein, the sequence of which is indicated or can be derived, for example, from the following sequences:
  FMDV serotype O complete genome: GenBank JX570650.1
  FMDV serotype A complete genome: GenBank HQ832592.1
  FMDV serotype C complete genome: GenBank AY593810.1
  FMDV serotype SAT 1 complete genome: GenBank AY593846.1
  FMDV serotype SAT 2 complete genome: GenBank JX014256.1
  FMDV serotype ASIA 1 complete genome: GenBank HQ631363.1.

Canine parvovirus VP1 and VP2 protein, the sequence of which is indicated or can be derived, for example, from the following sequences:
  Canine parvovirus VP1 gene for capsid protein VP1, partial cds, strain: 1887/173. GenBank: AB437434.1.
  Canine parvovirus VP1 gene for capsid protein VP1, partial cds, strain: 1887/M/2. GenBank: AB437433.1
  Canine parvovirus VP2 gene, complete cds, strain: HNI-2-13. GenBank: AB120724.1.
  Canine parvovirus VP2 gene, complete cds, strain: HNI-3-4. GenBank: AB120725.1.
  Canine parvovirus VP2 gene, complete cds, strain: HNI 1. GenBank: AB120726.1.
  Canine parvovirus VP2 gene, complete cds, strain: HNI-4-1. GenBank: AB120727.1.
  Canine parvovirus VP2 gene, complete cds, strain: HNI-1-18. GenBank: AB120728.1.
  Canine parvovirus VP2 protein (VP2) gene, complete cds. GenBank: DQ354068.1.
  Canine parvovirus VP2 gene, complete cds, strain: HCM-6. GenBank: AB120720.1.
  Canine parvovirus isolate Taichung VP2 gene, complete eds. GenBank: AY869724.1.
  Canine parvovirus VP2 gene, complete eds, strain: HCM-8. GenBank: ABI20721.1.
  Canine parvovirus type 1 proteins VP1 and VP2: GenBank. AB518883.1
  Canine parvovirus type 2a VP1 and VP2. GenBank: M24003.1
  Canine parvovirus type 2b VP2: GenBank FJ005265.1
  Canine parvovirus Type 2C VP2: GenBank FJ005248.1

Porcine parvovirus VP1 and VP2 protein, the sequence of which is indicated or can be derived, for example, from the following sequences:
  Porcine parvovirus strain 693a. GenBank: JN400519.1
  Porcine parvovirus strain 8a. GenBank: N400517.1

Human parvovirus VP1 and VP2 protein, the sequence of which is indicated or can be derived, for example, from the following sequences:

Human parvovirus B19 VP1 complete cds. GenBank: AF264149.1

Human parvovirus B19 isolate Vn115 NS1 (NS1), 7.5 kDa protein (NS1), VP1 (VP1), 9.5 kDa protein (VP1), and VP2 (VP2) genes, complete cds. GenBank: DQ357065.1
- B19 virus isolate FoBe VP1 (VP1) and VP2 (VP2) genes, complete cds. GenBank: AY768535.1
- B19 virus isolate Br543 NS1 (NS1), VP1 (VP1), and VP2 (VP2) genes, complete cds. GenBank: AY647977.1
- Human parvovirus 4 isolate VES065CSF NS1, VP1, and VP2 genes, complete cds. GenBank: HQ593532.1
- Human parvovirus 4 isolate VES085CSF NS1 gene, partial cds; and VP1 and VP2 genes, complete cds. GenBank: HQ593531.1
- Human parvovirus B19 strain BB-2 NS1, VP1, and VP2 genes, complete cds. GenBank: KF724387.1

Human norovirus (genogroup I or II) capsid protein, the sequence of which is indicated or can be derived, for example, from the following sequences:
- Norwalk virus: GenBank M87661, NP056821
- Southampton virus: GenBank L07418
- Mexico virus: GenBank U22498
- Seto virus: GenBank AB031013
- Chiba virus: GenBank AB042808
- Lordsdale virus: GenBank X86557
- Snow Mountain virus: GenBank U70059
- Hawaii virus: GenBank U07611

Rabbit haemorrhagic disease virus VP60 protein, the sequence of which is indicated or can be derived, for example, from the following sequence:
- RHDV AST/89 complete genome: GenBank: Z49271.2
- RHDV N11 complete genome: GenBank: KM878681.1
- RHDV CBVal16 complete genome; GenBank: KM979445.1
- SEQ ID NO.: 32
- SEQ ID NO.: 33

Human papillomavirus L1 protein, the sequence of which is indicated or can be derived, for example, from the following sequences:
- HPV 6: GenBank: JN1252323.1
- HPV 11: GenBank: JQ773411.1
- HPV 16: GenBank DQ155283.1
- HPV 18: GenBank FJ528600.1

Hepatitis E virus E2 protein, the sequence of which is indicated or can be derived, for example, from the following sequences:
- Hepatitis E virus, complete genome NCBI Reference Sequence: NC_001434.1
- Swine hepatitis E virus isolate ITFAE11 capsid protein gene. GenBank: JN861806.1

Infectious bursal disease virus VP1, VP2 and VP3 proteins, the sequence of which is indicated or can be derived, for example, from the following sequences:
- Infectious bursal disease virus VP1 (VP1) gene, complete cds. GenBank: AY099457.1
- Infectious bursal disease virus isolate PT VP1 gene, complete cds. GenBank: DQ679814.1
- Infectious bursal disease virus isolate OE/G2 VP1 gene, complete cds. GenBank: DQ679813.1
- Infectious bursal disease virus isolate OA/G1 VP1 gene, complete cds, GenBank: DQ679812.1
- Infectious bursal disease virus isolate HOL VP1 gene, complete cds, GenBank: DQ679811.1
- Infectious bursal disease virus strain 112004 VP1 gene, complete cds. GenBank: DQ118374.1
- Infectious bursal disease virus isolate CA-K785 VP1 gene, complete cds. GenBank: JF907705.1
- Infectious bursal disease virus isolate D495 VP1 gene, complete cds. GenBank: JF907704.1
- Infectious bursal disease virus strain A-BH83 VP1 mRNA, complete cds. GenBank: EU544149.1
- Infectious bursal disease virus strain Cro-Pa/98 VP1 gene, complete cds. GenBank: EU184690.1
- Infectious bursal disease virus VP2 mRNA, complete cds. GenBank: AY321509.1
- Infectious bursal disease virus VP2, VP3, VP4 genes, complete cds. GenBank: M97346.1
- Infectious bursal disease virus VP2 gene, complete cds. GenBank: A1508177.1

Calicivirus capsid protein, the sequence of which is indicated or can be derived, for example, from the following sequences:
- Feline calicivirus capsid protein gene, complete cds. GenBank: L09719.1
- Feline calicivirus capsid protein gene, complete cds. GenBank: L09718.1
- Human calicivirus HU/NLV/Wortley/90/UK RNA for capsid protein (ORF2), strain HU/NLV/Wortley/90/UK. GenBank: AJ277618.1
- Human calicivirus HU/NLV/Thistlehall/90/UK RNA for capsid protein (ORF2), strain HU/NLV/Thistlehall/90/UK. GenBank: AJ277621.1
- Human calicivirus HU/NLV/Valetta/95/Malta RNA for capsid protein (ORF2), strain HU/NLV/Valetta/95/Malta. GenBank: AJ277616.1
- Human calicivirus NLV/Stav/95/Nor capsid protein gene, complete cds. GenBank: AF145709.1
- Bovine enteric calicivirus strain Bo/CV500-OH/2002/US capsid protein gene, complete cds. GenBank: AY549155.1
- Human calicivirus NLV/Mora/97/SE capsid protein gene, complete cds. GenBank: AY081134.1
- Human calicivirus NLV/Potsdam 196/2000/DE capsid protein gene, complete cds. GenBank: AF439267.1
- Human calicivirus NLV/1581-01/SWE capsid protein gene, complete cds. GenBank: AY247442.1
- Human calicivirus Hu/NLV/GII/MD134-10/1987/US capsid protein gene, complete cds. GenBank: AY030313.1

Astrovirus ORF2-encoded proteins, the sequence of which is indicated or can be derived, for example, from the following sequences:
- Porcine astrovirus 4 ORF1b gene, partial cds; and ORF2 gene, complete cds. GenBank: JX684071.1
- Astrovirus MLB1 HK05, complete genome. NCBI Reference Sequence: NC_014320.1.
- Astrovirus wild boar/WBAstV-1/2011/HUN, complete genome, NCBI Reference Sequence: NC 016896.1
- Human astrovirus BF34, complete genome. NCBI Reference Sequence: NC_024472.1
- Astrovirus MLB1 strain Hu/ITA/2007/PR326/MLB1 RNA-dependent RNA polymerase (ORF1b) gene, partial cds; and capsid protein (ORF2) gene, complete cds, GenBank: KF417713.1
- Human astrovirus 5 strain Hu/Budapest/HUN5186/2012/HUN nonstructural protein (ORF1a) and nonstructural protein (ORF1b) genes, partial cds; and capsid protein (ORF2) gene, complete cds. GenBank: KF157967.1.

Human astrovirus 1 isolate Shanghai capsid protein (ORF2) gene, complete cds. GenBank: FJ792842.1

Human astrovirus type 8 orf2 gene for capsid protein. GenBank: 266541.1

Influenza virus HA, NA and M1 proteins, the sequence of which is indicated or can be derived, for example, from the following sequences:

SEQ ID NO.: 30

Influenza A virus (A/duck/Chiba/25-51-14/2013(H7N1)) HA gene for hemagglutinin, complete cds. GenBank: AB813060.1

Synthetic construct hemagglutinin (HA) mRNA, complete cds. GenBank: DQ868374.1

Influenza virus A (A/swine/Shandong/2/03(H5N1)) hemagglutinin (HA) gene, complete cds. GenBank: AY646424.1 cDNA encoding HA of influenza type A. GenBank: E01133.1

Influenza A virus (A/swine/Korea/S452/2004(H9N2)) NA gene, complete cds. GenBank: AY790307.1

Influenza A virus (A/Thailand/2(SP-33)/2004(H5N1)) neuraminidase (NA) gene, complete cds. GenBank: AY555152.3

Influenza A virus (A/swine/Binh Doung/02_16/2010 (H1N2)) NA gene for neuraminidase, complete cds. GenBank: AB628082.1

Influenza A virus (A/chicken/Jalgaon/8824/2006 (H5N1)) neuraminidase (NA) gene, complete cds. GenBank: DQ887063.1

Influenza A virus SC35M M2 and M1 genes, complete cds. GenBank: DQ266100.1

Influenza virus type/Leningrad/134/47/57 (H2N2) M1 and M2 RNA, complete cds's. GenBank: M81582.1

Influenza A virus SC35M M2 and M1 genes, complete cds. GenBank: DQ266100.1

Influenza A virus (A/Tochigi/2/2010(H1N1)) M2, M1 genes for matrix protein 2, matrix protein 1, complete cds. GenBank: AB704481.1

Hepatitis B core and surface antigens, the sequence of which is indicated or can be derived, for example, from the following sequences:

Hepatitis B virus strain HBV248 precore protein and core protein genes, complete cds. GenBank: KP857118.1

Hepatitis B virus strain HBV401 precore protein and core protein genes, complete cds. GenBank: KP857113.1

Hepatitis B virus strain HBV403 precore protein and core protein genes, complete cds. GenBank: KP857068.1

Hepatitis B virus S gene for hepatitis B surface antigen, partial cds, isolate: B0503327(PTK). GenBank: AB466596.1

Preferably, the recombinant protein is not a protein which is endogenously produced by pupae. For example, the recombinant protein is not a protein which is endogenously produced by pupae such as pupae of the species *Hyalophora cecropia*. For example, the recombinant protein is not cecropin A or attacin.

Figure 3:
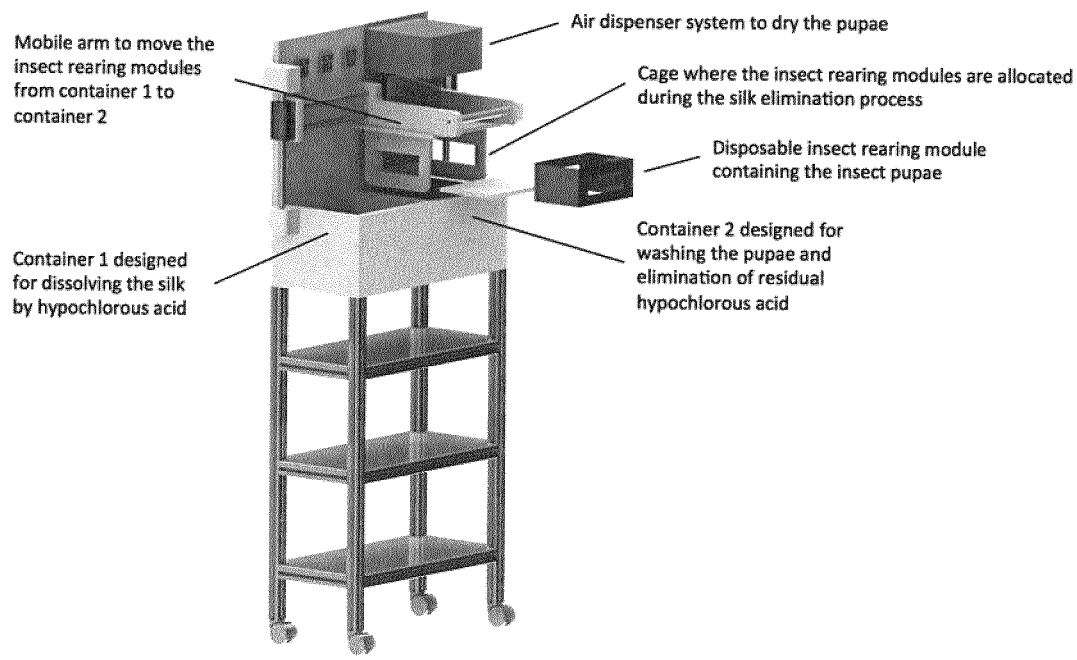
FIG. 3: Semi-automatic device for silk removal from the *T. ni* cocoons. Schematic representation of the machine containing two containers and a mechanic arm in which the single-use rearing module is allocated. The first container contains hypochlorous acid and a system to project the liquid through the rearing modules containing the cocoons (it helps to dissolve more efficiently the silk surrounding the pupa). The second container is to wash the pupae, and it sprays water over the chrysalises. On the top of this container there is a system that dispenses air to dry the pupae. At the end of the process, the pupae are free of silk and ready to be used in infection or to be stored refrigerated until use.

The pupa of the present invention may be a silk-free pupa, or may be inside a silk cocoon. If the pupa is not a silk-free pupa, the skilled person is aware of methods of removing the cocoon silk. For instance, the cocoon silk may be dissolved, preferably with a solution of a salt, preferably a salt of hypochlorous acid (HClO), preferably sodium hypochlorite (NaClO) (also referred to in the present description as "dissolving solution"). This procedure may be automated by a specifically designed device, as shown in FIG. 3.

Use of the Pupa of the Present Invention for the Expression of Recombinant Proteins The pupa of the present invention, in any of its variants, may be used for the expression of recombinant proteins. Accordingly, the present invention provides the use of the pupa of the present invention for the expression of recombinant proteins, preferably the recombinant proteins detailed above in this specification.

Methods for Producing Recombinant Proteins of the Present Invention

The present invention also provides methods for producing recombinant proteins (which, as already described above, are preferably not proteins which are endogenously produced by pupae). For instance, a method for providing at least one recombinant protein according to the present invention comprises, or, alternatively, consists of, the following steps:

(a) Providing a pupa;
(b) Inoculating the pupa of step (a) with a recombinant baculovirus derived from *Autographa californica* multicapsid nucleopolyhedrovirus (AcMNPV);
(c) Incubating the inoculated pupa of step (b) for a period of time sufficient for the at least one recombinant protein to be expressed;
(d) Obtaining the pupae comprising the at least one recombinant protein;
(e) Optionally, harvesting the at least one recombinant protein; and
(f) Optionally, purifying the at least one recombinant protein.

The pupa of step (a) of the above method may preferably be the pupa according to the present invention, as described in detail above. The pupa of step (a) preferably belongs to the order Lepidoptera. Preferably, the pupa belongs to the order Lepidoptera, preferably to the genus *Trichoplusia, Rachiplusia, Spodoptera, Heliothis, Manduca, Helicoverpa, Ascalapha* or *Samia*, preferably to the genus *Trichoplusia, Rachiplusia, Spodoptera, Heliothis* or *Helicoverpa*, more preferably to the species *Trichoplusia ni, Rachiplusia nu, Spodoptera frugiperda, Heliothis virescens, Helicoverpa armigera, Helicoverpa Zea, Manduca sexta, Ascalapha odorata* or *Samia cynthia*, even more preferably to the species *Trichoplusia ni*. As already described above, the pupa may comprise a nucleic acid sequence that allows for the expression of a recombinant protein. As already described above, the pupa may comprise a nucleic acid sequence that allows for the expression above endogenous levels of the proteins IE-1, IE-0 and/or fragments thereof functioning as transcriptional regulators above endogenous levels obtained during baculovirus infection (see above, "Pupa of the present invention").

The pupa of step (a) above may evolve from an egg. For example, the pupa of step a) above may evolve from egg to pupa for 15-18 days, e.g., in specially designed single-use or reusable rearing boxes. The pupa of step a) may also be provided already in the form of a pupa.

If the pupa of step (a) above is inside a cocoon, the method for producing recombinant proteins of the present invention may further comprise a step of removing the cocoon silk from the pupa. For instance, the cocoon silk may be dissolved, preferably with a solution of a salt which preferably comprises hypochlorous acid (HClO), preferably sodium hypochlorite (NaClO), for example at concentrations of 0.1% to 5% W/V, such as 0.1%, 0.2%, 0.5%, 1%, 3% or 5% W/V. For example, the pupae may be immersed or sprayed with a solution of sodium hypochlorite at a concentration of from 0.1% to 5% W/V. The dissolution of the cocoon silk may take from several seconds to several minutes. The elimination of the cocoon silk from the pupa of step (a), when the pupa is inside a cocoon, is preferably performed in a semi-automated or automated form (robotized silk elimination). In this regard, the fact that the cocoon of some species such as *Hyalophora cecropia* or *Bombyx mori* is a thick cocoon is a disadvantage over other genera or species (such as genera *Trichoplusia*, in particular the species *Trichoplusia ni*). Pupae of the genera *Trichoplusia*, in particular the species *Trichoplusia ni*, have a cocoon which is less dense in silk, and can be easily dissolved. This represents an advantage, since the whole process can be performed in an automatized or semi-automatized form, increasing the efficiency and reducing the overall costs.

The cocoon may be removed in a semi-automated machine which may comprise a recipient with the dissolving solution to be applied to the cocoon, preferably with pressurized air turbulences, to reduce the time needed for dissolving the silk cocoon. The silk-free pupae may then be washed in a washing container to remove traces of the dissolving solution, and then dried with air.

Accordingly, silk-free pupae are preferred, since then, step (b) is easier to perform. Accordingly, pupae with very dense cocoon are less preferred. For example, pupae of *Bombyx mori* have a very dense, thick and compact cocoon, which cannot be easily removed by dissolution with a salt solution for a few minutes, as described above. The same is true for the pupae of *Hyalophora cecropia*. The cocoon of *Bombyx mori* and/or *Hyalophora cecropia* pupae should be manually removed.

On the contrary, pupae of other species such as *T. ni* comprise a cocoon which is less dense in silk, and can be easily dissolved as described above. These pupae are thus preferred for the method of producing recombinant proteins of the present invention, since their cocoon can be removed by automatic or semiautomatic procedures, facilitating scale-up for obtaining pupae ready to be injected with a recombinant baculovirus (step (b)).

After removing the cocoon silk, the pupae are preferably washed with water, in order to remove traces of the salt solution (e.g., sodium hypochlorite). Silk-free pupae may be subsequently dried and stored at a low temperature (e.g., 4° C.) before step (b) is carried out. For instance, silk-free pupae may be storage up to 1 month at low temperature (e.g., 4° C.) before step (b) is carried out.

Accordingly, the present invention also provides a method for producing a silk-free pupa (preferably a silk-free pupa belonging to the genus Lepidoptera, preferably the pupa of the present invention), comprising the steps of:
  (a) Providing a pupa (preferably the pupa of the present invention as described above) contained in a cocoon;
  (b) Treating the pupa contained in a cocoon with a solution of a salt, preferably a solution of a salt of hypochlorous acid, preferably sodium hypochlorite, as described in detail above; and
  (c) Obtaining a silk-free (and preferably essentially disinfected) pupa.

The present invention thus also provides the pupa of the present invention which is essentially silk-free (namely, without a cocoon). In a preferred embodiment, the essentially silk-free pupa of the present invention does not belong to the species *Bombyx mori*. In a preferred embodiment, the essentially silk-free pupa of the present invention does not belong to the species *Hyalophora cecropia*. In a preferred embodiment, the essentially silk-free pupa of the present invention belongs to the genus *Trichoplusia*, *Rachiplusia*, *Spodoptera*, *Heliothis*, *Manduca*, *Helicoverpa*, *Ascalapha* or *Samia*, preferably to the genus *Trichoplusia*, *Rachiplusia*, *Spodoptera*, *Heliothis* or *Helicoverpa*. In a preferred embodiment, the essentially silk-free pupa of the present invention belongs to the species *Trichoplusia ni*, *Rachiplusia nu*, *Spodoptera frugiperda*, *Heliothis virescens*, *Helicoverpa armigera*, *Helicoverpa Zea*, *Manduca sexta*, *Ascalapha odorata* or *Samia cynthia*, even more preferably to the species *Trichoplusia ni*.

Step (b) of the method of the present invention is directed to the inoculation of the pupa of step (a) with a recombinant baculovirus derived from *Autographa californica* multicapsid nucleopolyhedrovirus (AcMNPV). Recombinant baculovirus which may be comprised in the pupa of the present invention have been described in detail above, and an exemplary schema is also shown in FIG. 4B. Accordingly, preferably, in step (b), the pupa of the present invention is inoculated with a recombinant baculovirus, in order to provide a pupa according to the present invention, comprising a recombinant baculovirus, as described above. The patent application published as WO2012/168492 discloses recombinant baculovirus that may be inoculated to the pupa according to the present invention in step (b) of the method for producing recombinant proteins of the present invention. The recombinant baculovirus comprises a nucleic acid sequence encoding a recombinant protein, preferably a recombinant protein selected from the group as defined above in this specification (expression cassette).

Silk-free pupae are preferred, since then the inoculation with the recombinant baculovirus is easier, and can be performed automatic or semiautomatic, facilitating the scale-up and reproducibility of the method.

The inoculation of the recombinant baculovirus according to step (b) may be performed by techniques known in the art to the skilled person. As defined herein, "inoculation" refers to the introduction of a substance into the body, in this case, the introduction of recombinant baculovirus into pupae. The inoculation may also be referred to as "injection". Since the larvae are inoculated with a baculovirus, this process may also be referred to in the present description as "infection of the larvae with a baculovirus".

Preferably, the inoculation is performed by injecting the pupa a specific amount of a solution comprising at least one baculovirus. The injection is preferably performed with a needle, which perforates the pupa and dispenses a specific amount of a solution comprising the baculovirus inside the body of the pupa. This step can also be automated; pupae may lay, e.g., in a matrix or array of alveolus, and an inoculation device or robot (described below) may automatically dispense the baculovirus inside the pupae. For instance, the pupa may lay in a matrix of alveolus (or array), the matrix including a top with a hole in the centre, so that the inoculation device or robot (comprising a needle, e.g., on a robotic arm) automatically positions the needle on the alveolus, and the needle access the pupa through the hole of the top. The needle penetrates the pupa's body, e.g., about 1-5 millimetres, preferably about 3 mm (this can also be automated) and dispenses the solution comprising the baculovirus inside the pupa. The device or robot may comprise a precision pump able to dispense an exact amount of baculovirus (e.g., about 0.5-10 microliter amounts of a solution comprising the baculovirus, preferably about 5 µl) into the pupae. The robot may comprise an arm comprising one or more needles able to inject the baculovirus into the pupae at precise positions. Once this has been performed, the robot leaves the alveolus, and, thanks to the top of the matrix where the pupae lay, the pupa is easily left on the matrix alveolus, and it is not removed from it when the robot arm removes the needle from the pupa, since the hole on the top of the matrix is smaller than the pupa, so that only the needle can go through it, so the needle is removed from the pupa and from the alveolus matrix leaving the pupa in it. With this preferable disposition, the inoculation process is automatic, rapid, efficient and highly reproducible (every pupa receives the same amount of solution comprising the baculovirus, with the same procedure). The robot may have several inoculation needles (namely, needles able to inoculate or inject the baculovirus into the pupae at precise positions) which may be removable, and may inoculate baculovirus into the pupae at a speed of between about 3.000 and about 10.000 pupae per hour.

For example, an amount of more than about 50 plaque-forming units (PFUs) of baculovirus is inoculated into each pupa. For example, about 50, about 100, about 500, about 1,000, about 5.000, about 10,000, about 15,000, about 20,000, about 25,000, about 30,000, about 40,000, about 50,000, about 60,000, about 75,000 or more PFUs (even about 1,000,000) are inoculated into each pupa. For example, as already mentioned above, the baculovirus are comprised in a solution, so a certain amount of a solution comprising baculovirus is injected into the pupae. For example, the solution may be cell culture media comprising baculovirus. For example, the solution may be a buffered solution comprising baculovirus, such as a solution of PBS 1× pH 7.4, 1 mM PMSF (proteases inhibitor) and 5 mM DTT comprising baculovirus. For example, the pupae can be inoculated with an amount of about 0.5-10 µl of a solution comprising a baculovirus, such as about 0.5 µl, such as about 1-10 µl, such as about 1, about 2, about 3, about 5, about 7 or about 10 µl. For example, each pupa receives 0.5-10 µl of a solution comprising between 50 to 1,000,000 PFUs.

Thanks to the automation of the inoculation, the robot may inoculate about 3,000 pupae per hour or more, such as between about 3.000 and about 10.000 pupae per hour. The robot is suitable to deliver a fluid into pupae provided in a matrix or array.

Step (c) of the method of the present invention comprises incubating the inoculated pupa of step (b) for a period of time sufficient for the at least one recombinant protein to be expressed. This incubation step may be preferably performed for a period of time of at least about 72 h, such as about 72 h, about 96 h, about 100 h, about 125 h, about 150 h, about 168 h or more (post-inoculation). Preferably, the incubation time is about 96-168 h post-inoculation or about 72-168 h post-inoculation. The inoculation step may be preferably performed at a temperature of about at 22-28° C., preferably in an incubator without any need for light or humidity control.

The inoculated pupae (preferably laying in the alveolus of the matrix) may be left on the alveolus of the matrix for the above period of time (incubation). In another embodiment, the pupae are removed from the matrix and placed anywhere else for the incubation time, such as bags or any recipient that allows transpiration (the incubation should be preferably performed in a container where there is an exchange of gases, not in a completely closed container).

The skilled person would calculate the required incubation time and incubation conditions for each pupae and each recombinant protein on the basis of previous experiments, depending on the protein to be expressed.

Step (d) of the method of the present invention comprises obtaining the pupae comprising the at least one recombinant protein which has been expressed during the incubation step (c). The pupae comprising the at least one recombinant protein may be collected from the matrix/array (or incubation place). These pupae comprising the at least one recombinant protein may be stored (frozen or lyophilized) for subsequent processing. For example, the pupae comprising the at least one recombinant protein may be packed in a package (preferably under vacuum). The package comprising the pupae may be stored, transported and/or further processed.

The present invention also provides a package comprising the pupae of the present invention, wherein preferably, the pupae comprise at least one recombinant protein. Preferably, the pupae are packaged under vacuum, and the package of the present invention thus comprises vacuum pupae, which are e.g., frozen or lyophilized, to avoid oxidation. This allows for an easier manipulation and longer storage periods.

The pupae obtained according to step (d) of the above method may also be frozen and stored for further processing. For instance, the pupae may be frozen immediately after collecting them at about −20° C., or at about −80° C., until they are further processed. For example, the pupae comprising the at least one recombinant protein may be frozen at a temperature of, for example, between about −20° C. and −70° C., until the recombinant protein is extracted. The pupae comprising the recombinant protein may be stored frozen for long period of times, such as, for example, for more than 1 year.

(Optional) step (e) of the method of the present invention comprises, optionally, harvesting the at least one recombinant protein. The skilled person is aware of methods and protocols for harvesting the at least one recombinant protein comprised in the pupae obtained in step (d). Of course, these methods and/or protocols may depend on the nature of the recombinant protein that has been expressed.

For example, the protein may be extracted by homogenising the pupae (e.g., in a homogenizer machine or homogenizer mixer, such as a blender homogenizer or a rotor-stator homogenizer, for at least several seconds/minutes), preferably in the presence of a neutral pH buffer, which buffer preferably comprises anti-oxidants (reducing agents), protease inhibitors and appropriate detergents. For example, the buffer comprises about 1-25 mM of a reducing agent and about 0.01%-2% (volume/volume) of a detergent product. Preferably, the buffer further comprises a mixture of protease inhibitors.

After homogenisation the extracts may be sonicated and/or centrifuged (e.g., 15,000-20,000 G) to eliminate the insect debris and filtrated.

For example, the extraction means (methods and protocols for harvesting the at least one recombinant protein comprised in the pupae) comprise physically disrupting the pupae, centrifugations, tangential flow filtration steps, sonication, chromatographic methods and/or sterilizing filtrations.

In a preferred embodiment, the viscosity of the homogenate may be reduced through its incubation (filtration) with a diatomaceous earth (e.g., Celite). A protein precipitation step could be included.

The extract may be clarified through tangential flow filtration, using a filter that the skilled person is available to select depending on the nature of the recombinant protein. The buffer may be changed by a diafiltration process (e.g., in the same tangential filtration device).

(Optional) step (f) of the method of the present invention comprises, optionally, purifying the at least one recombinant protein. The skilled person is aware of protein purification techniques. For instance the purification may be achieved by chromatography purification, filtration or ultracentrifugation.

Figure 17:
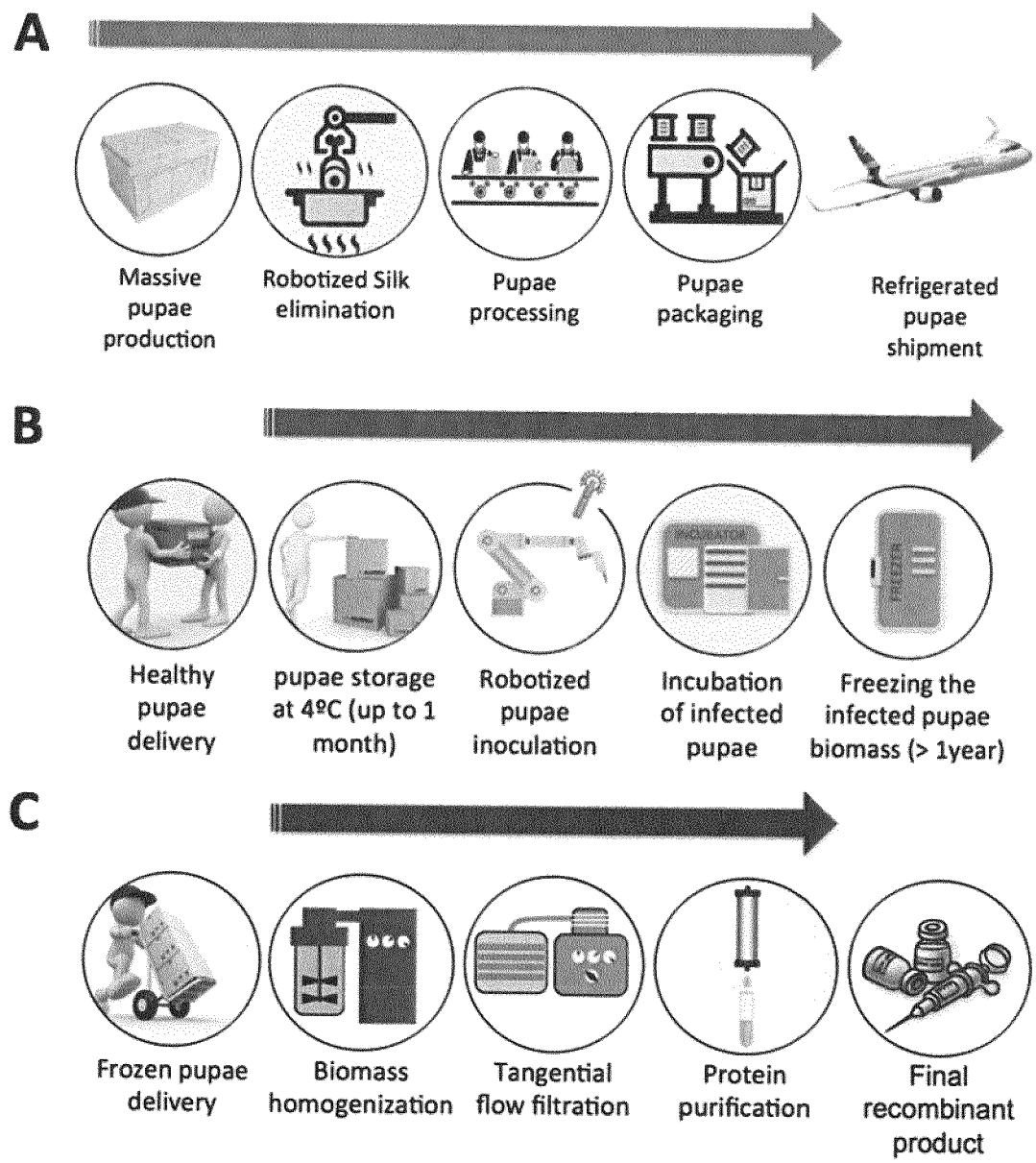
FIG. 17: Schematic example of upstream and downstream processing procedure to obtain a purified recombinant protein from infected pupae in three steps. A) Production of T. ni chrysalises, their manipulation and optionally shipping to the final destination (e.g., pharmaceutical company) for recombinant protein production. B) Pupae storage, robotic inoculation with recombinant baculovirus using the device of the present invention, incubation and frozen insect biomass, which can be stored for months before processing in situ, or which can be easily shipped to other locations for proceeding with the downstream processing. C) Downstream processing by conventional means of frozen biomass, including homogenization, tangential flow filtration and protein purification.

The purified recombinant protein may thus be obtained. A schema of one embodiment of this method is shown in FIG. 17.

The recombinant protein obtainable by the method of the present invention has a high purity degree, and may be used in vaccines, diagnosis, cosmetics or in therapy.

Method for Producing a Recombinant Baculovirus of the Present Invention

The present invention further provides a method for producing a recombinant baculovirus comprising the steps of:
- (a) Providing a pupa,
- (b) Transfecting the pupa of step (a) with a bacmid vector suitable for producing a recombinant baculovirus derived from *Autographa californica* multicapsid nucleopolyhedrovirus (AcMNPV);
- (c) Incubating the inoculated pupa of step (b) for a period of time sufficient for the recombinant baculovirus is produced;
- (d) Obtaining the pupae comprising the recombinant baculovirus;
- (e) Optionally, harvesting the recombinant baculovirus; and
- (f) Optionally, purifying the recombinant baculovirus.

Preferably, the pupa provided in step (a) is a silk-free pupa as defined above. The pupa preferably belongs to the genus *Trichoplusia, Rachiplusia, Spodoptera, Heliothis, Manduca, Helicoverpa, Ascalapha* or *Samia*, preferably to the genus *Trichoplusia, Rachiplusia, Spodoptera, Heliothis* or *Helicoverpa*, more preferably to the species *Trichoplusia ni, Rachiplusia nu, Spodoptera frugiperda, Heliothis virescens, Helicoverpa armigera, Helicoverpa Zea, Manduca sexta, Ascalapha odorata* or *Samia cynthia*, even more preferably to the species *Trichoplusia ni*.

In step (b), the pupa of step (a) is transfected with a bacmid vector suitable for producing a recombinant baculovirus derived from *Autographa californica* multicapsid nucleopolyhedrovirus (AcMNPV).

This step (b) may also be referred to as "inoculation step", since it can be performed in a similar way as step (b) of the method for producing a recombinant protein described above (but instead of inoculating a baculovirus, a bacmid vector is inoculated), namely in an automatic or semiautomatic way, using the device of the present invention (also described below). The device may inoculate into the pupa (which is preferably placed in the alveolus of a matrix, comprising a tap with holes) a specific amount of a solution comprising the transfer vector and/or bacmid to be inoculated to the pupa, by means of injection with a needle, as described above.

The bacmid vector may be generated by procedures known to the skilled person, for example by generating sequentially a cloning vector, a donor vector, a transfer vector and, finally, a bacmid vector. For example, the generation of a bacmid vector is described in the patent application published as WO 2014/086981.

In a preferred embodiment, this transfer vector and/or bacmid comprises or alternatively, consists of, a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein. These nucleic acid sequences have been already described above. For instance, the nucleic the nucleic acid sequence that allows for the expression of the proteins IE-1, IE-0 and/or fragments thereof is preferably selected from the group consisting of:
- (a) a nucleic acid containing the nucleotide sequence indicated in any of SEQ ID NO: 1-5;
- (b) a nucleic acid sequence having a sequence identity of at least 70%, preferably at least 75%, more preferably at least 80%, more preferably at least 85%, more preferably at least 90% and most preferably at least 95% with the nucleotide sequence indicated in any of SEQ ID NO: 1-5 and encoding a protein able to function as a transcriptional regulator in a recombinant baculovirus;
- (c) a nucleic acid sequence encoding an amino acid containing the amino acid sequence indicated in any of SEQ ID NO: 6-9; and
- (d) a nucleic acid sequence encoding an amino acid sequence having a sequence similarity of at least 70%, preferably at least 75%, more preferably at least 80%, more preferably at least 85%, more preferably at least 90% and most preferably at least 95% with the amino acid sequence indicated in any of SEQ ID NO: 6-9 and able to function as a transcriptional regulator in a recombinant baculovirus.

In addition, the promoter that drives the expression of said recombinant protein is preferably selected from the group of nucleic acids comprising:
- (a) a nucleic acid containing the nucleotide sequence indicated in any of SEQ ID NO: 10-14, preferably indicated in any of SEQ ID NOs: 11-13; and
- (b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NO: 10-14, preferably indicated in any of SEQ ID NOs: 11-13.

The recombinant homologous region (hr) is preferably the sequence indicated in SEQ ID NO: 21 (hr1). The nucleic acid sequence that comprises combinations of recombinant promoter, sequences encoding transcriptional regulators and enhancer regions are preferably selected from the group comprising SEQ ID NO: 15-20.

Preferably, the vector inoculated to the pupae is a bacmid.

Step (c) refers to the incubation of the inoculated pupa of step (b) for a period of time sufficient for the recombinant baculovirus is produced. For example, this period of time for pupa of *T. ni* may be from about 72 h to about 7 days, depending on the virus dose and temperature. The skilled person is able to calculate the period of time sufficient for the recombinant baculovirus to be produced.

Then, the pupae comprising the recombinant baculovirus is obtained (step (d)). The pupae comprising the recombinant baculovirus may be stored for further processing. For instance, they may be vacuum packaged, to reduce the oxidation process and facilitate their manipulation and increase the safe storage time. For example, the pupae comprising the recombinant baculovirus may be frozen (e.g., at −20° C. to −80° C.) before they are further processed. For example, the pupae comprising the recombinant baculovirus may be lyophilized before they are further processed.

Optionally, the recombinant baculovirus may be harvested and purified (steps (e) and (f)).

Device of the Present Invention

The present invention also provides a device (also referred to in the present invention as robot) comprising a precision pump, a mobile mechanic arm and a (removable) needle suitable for injecting a fluid (preferably a solution comprising baculovirus or bacmid vectors) into a pupa (preferably to the pupa of the present invention, which is preferably a silk-free pupa and which preferably belongs to the order Lepidoptera, preferably to the genus *Trichoplusia, Rachiplusia, Spodoptera, Heliothis, Manduca, Helicoverpa, Ascalapha* or *Samia*, preferably to the genus *Trichoplusia, Rachiplusia, Spodoptera, Heliothis* or *Helicoverpa*, more preferably to the species *Trichoplusia ni, Rachiplusia nu, Spodoptera frugiperda, Heliothis virescens, Helicoverpa armigera, Helicoverpa Zea, Manduca sexta, Ascalapha odorata* or *Samia cynthia*.

As described in detail above, the pupa may preferably be provided in a matrix (or array), namely the pupa lays in the alveolus of a matrix, so that the device can easily locate the pupae in an automatic manner. Preferably, the matrix comprises a taps, with wholes that are smaller than the pupa (namely the pupae cannot pass through the holes).

The device may further comprise a computer program for defining the position of the needle (and/or the position of the mechanic arm) and/or for calculating the distance from the tip (end) of needle to the pupa and/or the distance of penetration of the needle into the pupa and/or the volume of liquid (preferably a solution comprising baculovirus or bacmid vectors) to be inoculated into the pupa. In addition, the device of the present invention may further comprise a computer program for calculating the inoculation time and/or the time between different inoculations into the pupae. The device may further comprise a camera for defining the position of the needle.

In a preferred embodiment, the fluid injected by the device of the present invention comprises a recombinant baculovirus. In another embodiment, the fluid injected by the device of the present invention comprises a bacmid vector suitable for producing a recombinant baculovirus derived from AcMNPV, as described above in this description.

The device of the present invention is suitable for performing step (b) of the method for producing a recombinant protein of the present invention and step (b) of the method of providing a recombinant baculovirus of the present invention.

For example, the device of the present invention is suitable to inject (inoculate) into the pupa an amount of fluid which is in the range of from about 0.5 to about 10.0 µL, such as about 0.5 µl, such as about 1-10 µl, such as about 1, about 2, about 3, about 5, about 7 or about 10 µL.

For example, the needle comprised in the device of the present invention is able to penetrate into the pupa a distance of from about 1 to about 4.5 mm, preferably about 3 mm.

For example, the device of the present invention comprises several removable inoculation needles, and is able to inoculate fluid (preferably a solution comprising baculovirus or bacmid vectors) at speeds of between about 3.000 and 10.000 pupae per hour.

For example, the fluid injected by the device of the present invention comprises baculovirus, preferably in an amount of from 50 to $10^6$ PFUs/dose injected into each pupa. For example, the device of the present invention injects (inoculates) to each pupa an amount of more than about 50, or more than about 100, or more than about 500 plaque-forming units (PFUs) of baculovirus. For example, about 50, about 100, about 300, about 500, about 1,000, about 5,000, about 10,000, about 15,000, about 20,000, about 25,000, about 30,000, about 40,000, about 50,000, about 100,000, about 500,000 or more PFUs are inoculated into each pupa, such as about 1,000,000 PFUs.

The device of the present invention preferably comprises high precision pumps which enable the device to inoculate the desired volume of fluid (preferably a solution comprising baculovirus or bacmid vectors) into the pupae with a high precision.

The device of the present invention is suitable to deliver a fluid into pupae provided in a matrix or array.

Preferably, the device of the present invention further comprises a computer program for calculating the inoculation time and/or the time between inoculations into the pupae, which should be enough time to dispense the liquid containing the baculovirus to each pupa.

Preferably, the device of the present invention further comprises a camera for defining the position of the needle.

The present invention further provides a device for silk removal (silk-removal device). A schematic representation of an example of silk-removal device of the present invention is represented in FIG. 3 (semi-automatic device for silk removal from the *T. ni* cocoons).

The silk-removal device of the present invention (also referred to as "silk-removal machine") comprises at least one container which contains a silk-dissolving solution, as explained above. For example, the container comprises hypochlorous acid. The first container may preferably also comprise a system to project the liquid through the rearing modules containing the cocoons (it helps to dissolve more efficiently the silk surrounding the pupa). The dissolving solution is preferably applied to the cocoon with pressurized air turbulences, to reduce the time needed for dissolving the silk cocoon.

Preferably, the silk-removal device of the present invention further comprises a second container, which is a wash-container and comprises and/or disperses a solution suitable for removing traces of silk and silk-dissolving solution from the pupae, such as water. The solution (preferably water) is preferably sprayed over the chrysalises (pupae). Preferably, on top of this container, there is a system that dispenses air to dry the pupae. Accordingly, after the washing of the pupae, they are preferably dried with air. At the end of the process, the pupae are free of silk and ready to be infected or to stored (refrigerated) until use.

| Summary of sequences | |
|---|---|
| SEQ ID NO: | Name: |
| 1 | Complete Ac-ie-01 cDNA |
| 2 | Protein coding sequence (CDS) of IE-1 |
| 3 | CDS of IE-0 |
| 4 | CDS of the IE-1 N-terminal domain |
| 5 | CDS of the IE-0 N-terminal domain |
| 6 | IE-1 protein |
| 7 | IE-0 protein |
| 8 | IE-1 N-terminal domain protein |
| 9 | IE-0 N-terminal domain protein |
| 10 | polh (promoter) |
| 11 | p10 (promoter) |
| 12 | pB2$_9$p10 (promoter) |
| 13 | p6.9p10 (promoter) |
| 14 | pB2$_9$ (promoter) |
| 15 | polhAc-ie-01/hr1p10 |
| 16 | polhAc-ie-01/hr1pB2$_9$p10 |
| 17 | polhAc-ie-01/hr1p6.9p10 |
| 18 | pB2$_9$Ac-ie-01/hr1p10 |

-continued

Summary of sequences

| SEQ ID NO: | Name: |
|---|---|
| 19 | pB2₉Ac-ie-01/hr1pB2₉p10 |
| 20 | pB2₉Ac-ie-01/hr1p6.9p10 |
| 21 | Homologous region enhancer hr1 |
| 22 | polhAc-ie-01 |
| 23 | polhGFP |
| 24 | hr1pB2₉p10 |
| 25 | ORF2 from porcine circovirus type 2 |
| 26 | Capsid protein (Cap) from porcine circovirus type 2 |
| 27 | polhAc-ie-01/hr1p6.9p10Cap (including the polyadenylation signal from the p10 gene after the Cap gene) |
| 28 | polhCap |
| 29 | polhAc-ie-01/hr1p6.9p10Cap |
| 30 | Hemagglutinin protein without transmembrane domain from an H1 influenza virus, PR8 strain (MelHAHis) |
| 31 | polhAc-ie-01/hr1p6.9p10HA1 (including the polyadenylation signal from the p10 gene after the H1gene) (polhAc-ie-01/hr1p6.9p10MelHA) |
| 32 | VP60 from RHDV AST789 (genogroup G1) |
| 33 | VP60 from RHDV N11 (genogroup RHDVb) |
| 34 | polhAc-ie-01/hr1p6.9p10VP60G1 (including the polyadenylation signal from the p10 gene after the H1gene) |
| 35 | polhAc-ie-01/hr1p6.9p10VP60RHDVb (including the polyadenylation signal from the p10 gene after the H1gene) |
| 36 | VP60 from RHDV AST789 (genogroup G1) (amino acid sequence) |
| 37 | VP60 from RHDV N11 (genogroup RHDVb) (amino acid sequence) |
| 38 | polhAc-ie-01/hr1p6.9p10GFP |

EXAMPLES

Example 1. Production of *T. ni* Pupae

Figure 2:
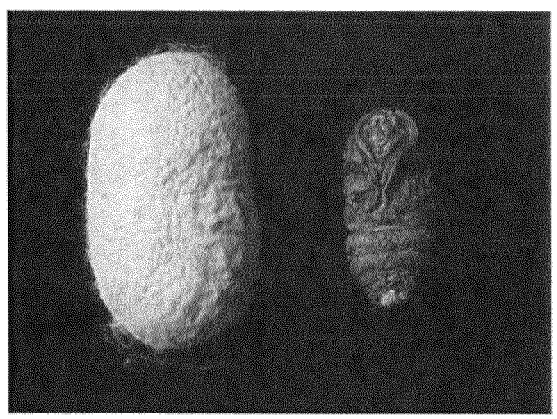
FIG. 2: Comparison of cocoons (left part of the image) and pupae free of silk (right part of the image) formed by *Bombyx mori* and *Trichoplusia ni* Lepidoptera.
Figure 2:
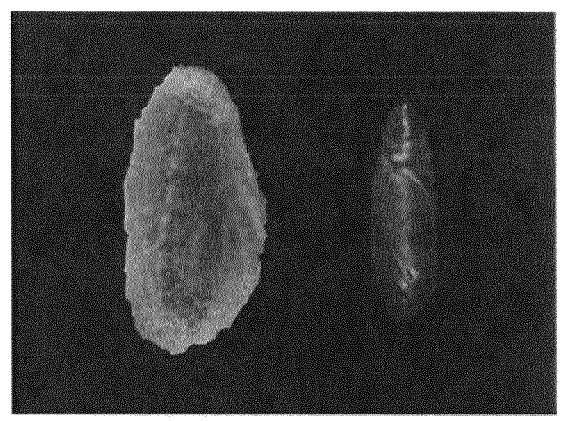

Insect larvae were reared in re-usable or single-use rearing boxes containing several hundreds of larvae that were allowed to evolve for 15-18 days from egg to pupa (FIG. 1). Then, whole rearing boxes or collected pupae were immersed or sprayed with a solution of sodium hypochlorite at concentrations of 0.1% to 5% W/V to dissolve the silk fibers of the cocoons. Silk was dissolved in a few minutes and pupae were then washed with water to remove traces the hypochlorite. Pupae were subsequently dried and stored at 4° C. until baculovirus inoculation. This process is more simple with respect to the same operation with *Bombyx mori* cocoons because of the lower density of silk treats of *T. ni* Lepidoptera, as can be seen in FIG. 2. *Bombyx mori* cocoons require manual intervention to liberate the pupae, while *T. ni* silk is easy to dissolve and remove by automatic or semi-automatic procedures, facilitating scale-up the obtaining of pupae ready to be injected with a recombinant baculovirus for recombinant protein production.

Figure 4:
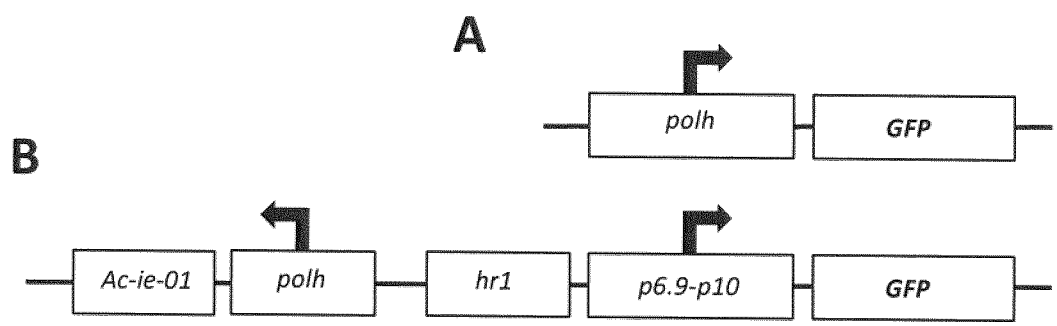
FIG. 4: Baculovirus expression cassettes used to produce the Green fluorescent protein (GFP). A) Conventional baculovirus expression cassette using the polyhedrin promoter (e.g., SEQ ID NO.: 23). B) TB expression cassette comprising the Ac-ie-01 cDNA encoding for the transactivators IE1 and IE0 expressed under the control of the polyhedrin promoter; the enhancer sequence hr1 and the chimeric promoter p6.9-p10 driving the expression of the GFP (e.g., SEQ ID NO.:17 and a nucleic acid sequence encoding GFP, e.g., SEQ ID NO.: 38).
Figure 5:
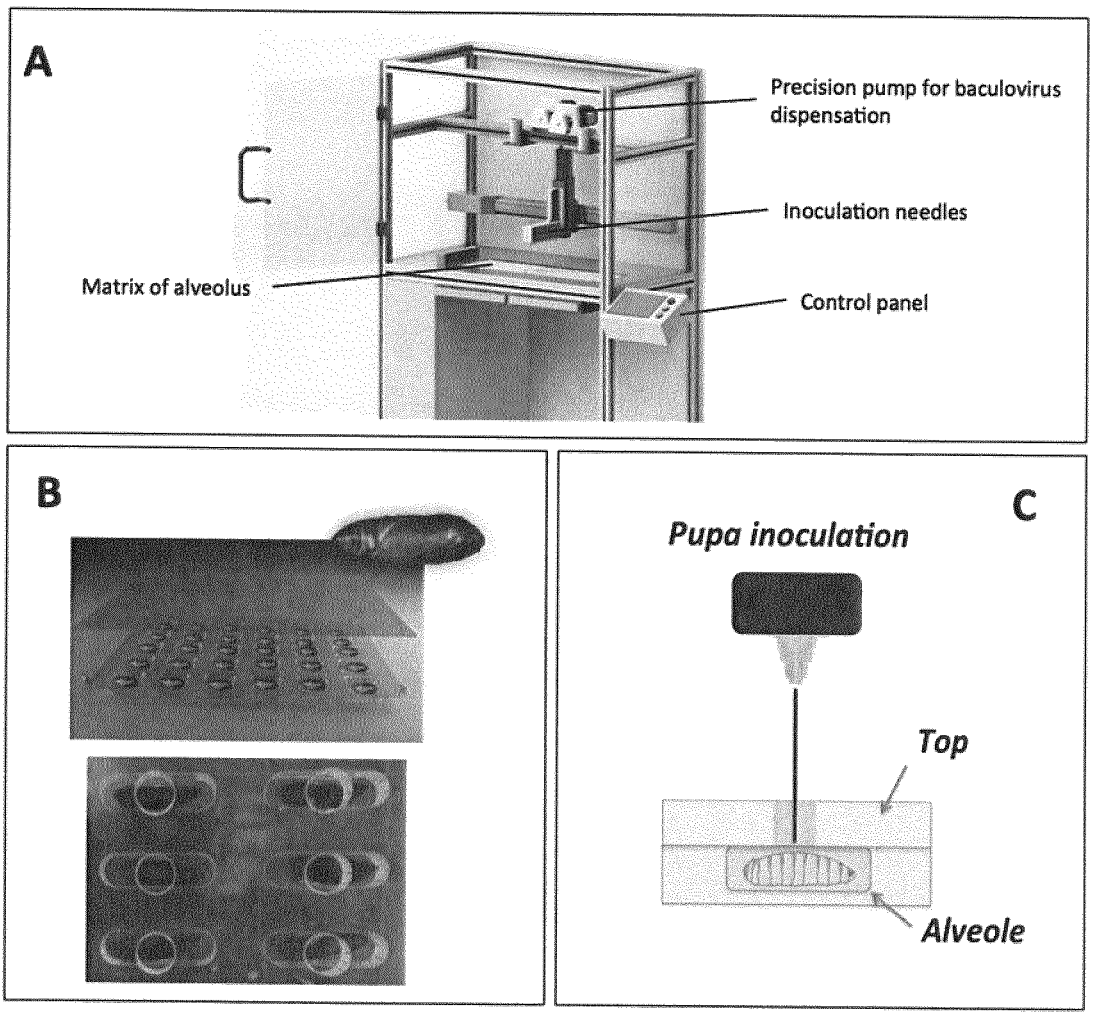
FIG. 5: Automatic inoculation of *T. ni* pupae by a robot injecting the recombinant baculovirus. A) Schematic representation of the inoculation robot. B) Schematic representation of a matrix of alveolus where the insect pupae are allocated. These alveoli containing the pupae have a perforated top and are stackable facilitating the transport of the pupae to the production laboratory and are compatible with the inoculation robot. In the same panel a real photograph image of the alveolus containing the pupae and with the top. C) Schematic representation of the pupae inoculation with a needle connected with the robotic arm.

Example 2. Dual Recombinant Baculoviruses Containing an Enhancer Sequence (hr1) Operatively Linked to a Chimeric Promoter (p6.9 and p10) and the Over-Expressed IE-1 and IE-0 Transactivation Factors are Highly Efficient in Producing Recombinant Proteins in Insect Pupa The recombinant protein expression driven under the control of a chimeric promoter enhanced by the baculovirus homologous repeated sequence hr1 and trans-activated by the over-expressed IE-1 and IE0 factors was compared in insect pupa (*T. ni*) to that obtained by using a conventional baculovirus. The encoding gene for the recombinant Green fluorescent protein (GFP) was cloned in a conventional AcMNPV baculovirus under the control of polyhedrin promoter by conventional means (FIG. 4A). Another AcMNPV baculovirus modified by the cassette containing the above mentioned regulatory elements (TB expression cassette) was also generated containing the GFP encoding gene (FIG. 4B). Pupae were infected with 50,000 PFUs of each baculovirus by an inoculation robot (FIG. 5A), comprising a precision pump able to dispense microliter amounts of the virus inoculum and a robotic arm able to inject the virus in precise positions. Pupae were allocated in a matrix of alveolus with a top with a hole in the center of every alveolus (FIG. 5B). The inoculation needle (removable) accessed to the pupae through the hole and penetrated the pupae several millimeters to inject the baculovirus (FIG. 5C). The recombinant virus contained in 0.5 to 10 microliters (µl) was dispensed into the pupae and during retraction of the needle the pupae were retained in the alveolus due to the top. This inoculation robot showed an inoculation speed of at least 3,000 pupae per hour, at least 6 times more speed than manual inoculation by a skilled person.

Figure 6:
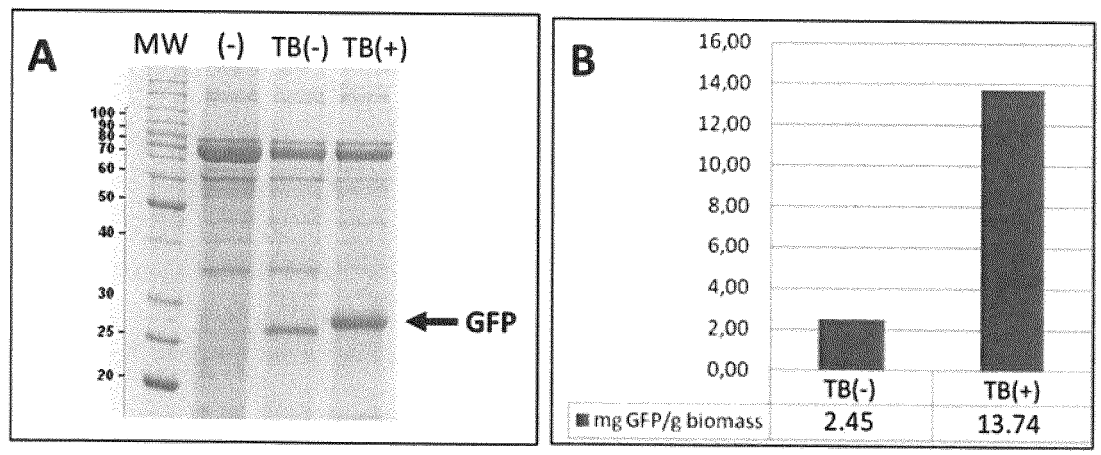
FIG. 6: Comparative analysis of the expression yields of the GFP protein in infected pupae by using a conventional baculovirus TB(-) (polyhedrin promoter, e.g., SEQ ID NO.: 23) or a TB-modified baculovirus TB(+). A) Coomassie blue staining of a SDS-PAGE resolving protein extracts from infected pupae with the TB(-) or TB(+) baculoviruses. (-) corresponds to an extract from an uninfected control pupa. B) Quantification of GFP production yields obtained in pupae infected by every baculovirus analyzed expressed in mg per g of pupae biomass.

After an incubation period after inoculation of 96-168 h, the pupae were collected and protein was extracted in a homogenizer machine in presence of a neutral pH buffer containing anti-oxidants, protease inhibitors and non-ionic detergents (e.g., PBS1× pH 7.4+5 mM Dithiothreitol (DTT) phenylmethylsulfonyl fluoride (PMSF)+0.1% Brij 35±0.5% Sarkosyl. Extracts were centrifuged at 15,000-20,000 g and filtered. Extracts were analyzed by SDS-PAGE electrophoresis and gels were stained with Coomassie blue (FIG. 6A). The production yields (expressed as milligrams per biomass unit) of the GFP protein produced by each baculovirus in the infected pupae were calculated by densitometry using a bovine serum albumin (BSA) curve. This analysis rendered an increase of around 5.6 times of GFP productivity in pupae obtained by the baculovirus genetically modified with the TB cassette with respect to that obtained with the conventional baculovirus (namely a baculovirus comprising, e.g., the polyhedrin promoter without any other regulatory element in the expression cassette) (FIG. 6B).

Figure 7:
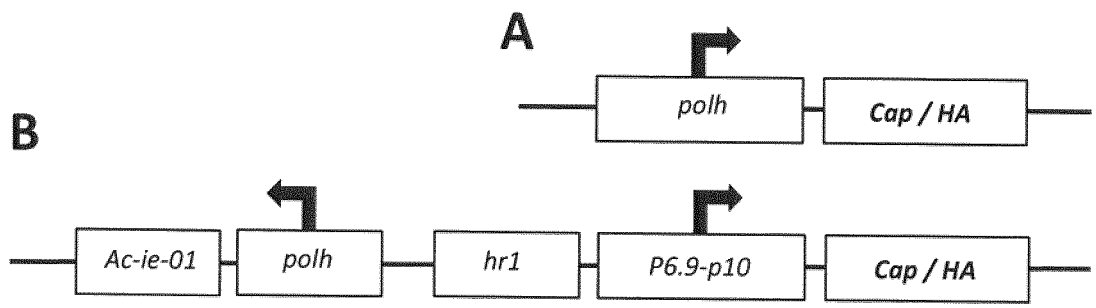
FIG. 7: Baculovirus expression cassettes used to produce the capsid protein from porcine circovirus type 2 (Cap) (e.g., SEQ ID NO.: 26) or the hemagglutinin (HA) from influenza virus (e.g., SEQ ID NO.: 30). A) Conventional baculovirus expression cassette using the polihedrin promoter. B) TB expression cassette comprising the Ac-ie-01 cDNA encoding for the transactivators IE1 and IE0 expressed under the control of the polyhedrin promoter; the enhancer sequence hr1 and the chimeric promoter p6.9-p10 driving the expression of the above mentioned proteins.

Example 3. Expression of Different Proteins by TB-Modified Baculoviruses in *T. ni* Pupae To analyze the benefit of using the TB (TopBac) expression cassette (SEQ ID NO.: 17) for the expression of further proteins, two genes were cloned in the TB cassette and the corresponding recombinant baculoviruses were obtained, as well as conventional baculoviruses expressing the genes under the control of polyhedrin promoter (polh) (FIG. 7). The two genes used for obtaining the recombinant baculoviruses were those encoding for the proteins Cap from Porcine circovirus type 2 derived from the PCV2a GER3 strain (SEQ IS NOs: 25 and 27) and the hemagglutinin from influenza virus (H1) derived from the virus strain A/PR/8/34 (SEQ ID NOs: 30 and 31). The resulting TB(−) (namely a conventional baculovirus that includes the polyhedrin promoter to express the protein in the expression cassette but which was not modified by the TopBac (TB) expression cassette) and TB(+) baculoviruses were compared for their productivity in *T. ni* pupae using the same infection and protein extraction protocols as the ones used and described in Example 2.

Figure 8:
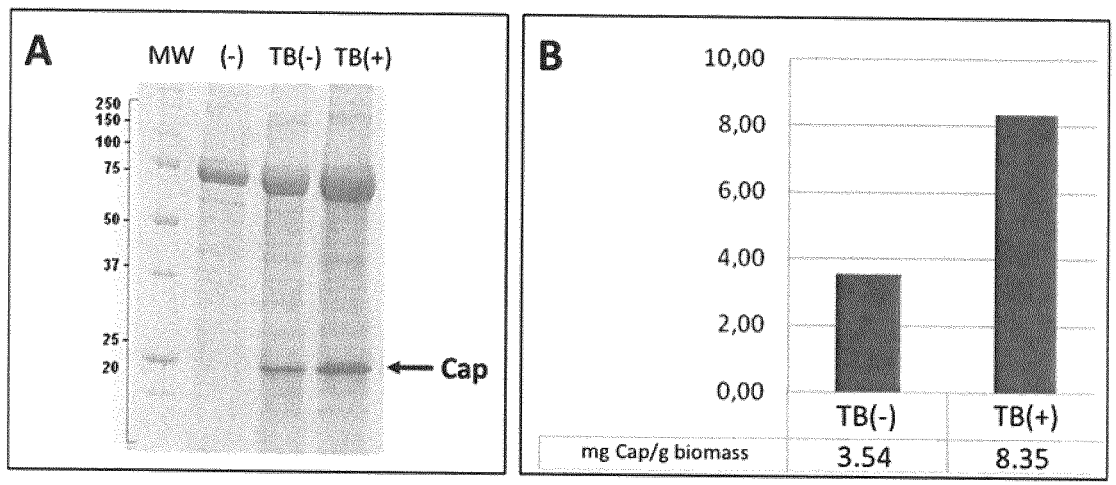
FIG. 8: Comparative analysis of the expression yields of the Cap protein (e.g., SEQ ID NO.: 26) in infected pupae by using a conventional baculovirus TB(-) (polyhedrin promoter, SEQ ID NO.: 10, SEQ ID NO.: 28) or a TB-modified baculovirus TB(+) (e.g., SEQ ID NO.: 27 or 29). A) Coomassie blue staining of a SDS-PAGE resolving protein extracts from infected pupae with the TB(-) or TB(+) baculoviruses. (-) corresponds to an extract from an uninfected control pupa. B) Quantification of Cap production yields obtained in pupae infected by every baculovirus analyzed expressed in mg per g of pupae biomass.
Figure 9:
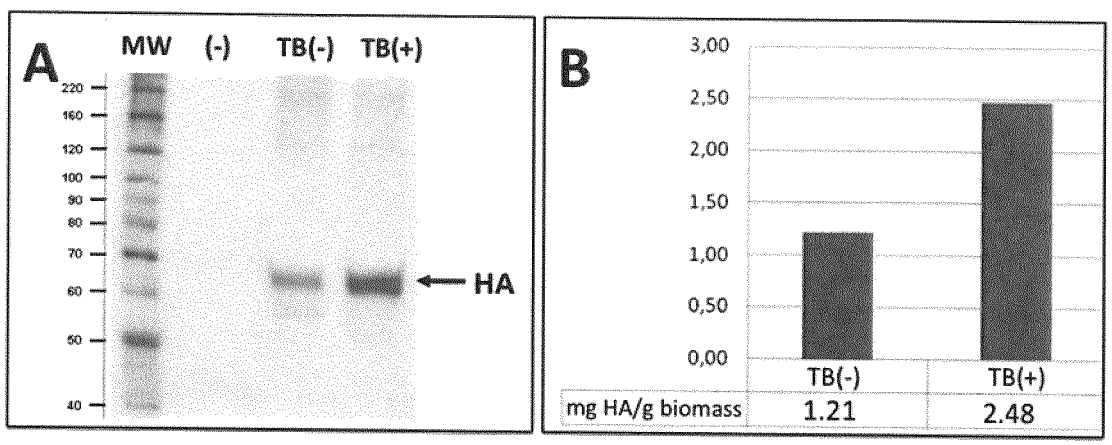
FIG. 9: Comparative analysis of the expression yields of the HA protein (SEQ ID NO.: 30) in infected pupae by using a conventional baculovirus TB(-) (polyhedrin promoter, SEQ ID NO.: 10) or a TB-modified baculovirus TB(+) (e.g., SEQ ID NO.: 31). A) Coomassie blue staining of a SDS-PAGE resolving protein extracts from infected pupae with the TB(-) or TB(+) baculoviruses. (-) corresponds to an extract from an uninfected control pupa. B) Quantification of HA production yields obtained in pupae infected by every baculovirus analyzed expressed in mg per g of pupae biomass.

The comparison of production yields (expressed as milligrams per biomass unit) in infected pupae mediated by conventional (TB(−)) or TB-modified (TB(+)) baculoviruses showed that for both proteins the expression cassette TB increased the production yield. In the case of the porcine circovirus Cap protein, an increase of 2.79 times in protein production when the pupa was infected with a TB-modified baculovirus as compared with pupa infected with conventional baculovirus (FIG. 8). For the HA protein from influenza virus this increase was of 2.04 times (FIG. 9). These results confirmed that the TB cassette significantly increases the production of recombinant proteins in T. ni pupae.

Figure 10:
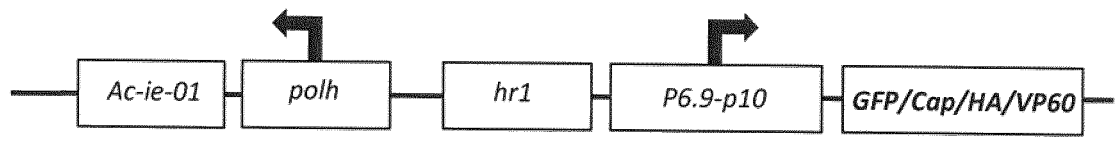
FIG. 10: Baculovirus expression cassette used to produce the GFP, Cap (SEQ ID NO.: 26), HA (SEQ ID NO.: 30) and the VP60 protein from rabbit haemorrhagic disease virus (RHDV, SEQ ID NO.:32 or 33) in *T. ni* larvae and pupae. Schematic representation of the TB expression cassette comprising the Ac-ie-01 cDNA encoding for the transactivators IE1 and IE0 expressed under the control of the polyhedrin promoter; the enhancer sequence hr1 and the chimeric promoter p6.9-p10 driving the expression of the above mentioned proteins.
Figure 11:
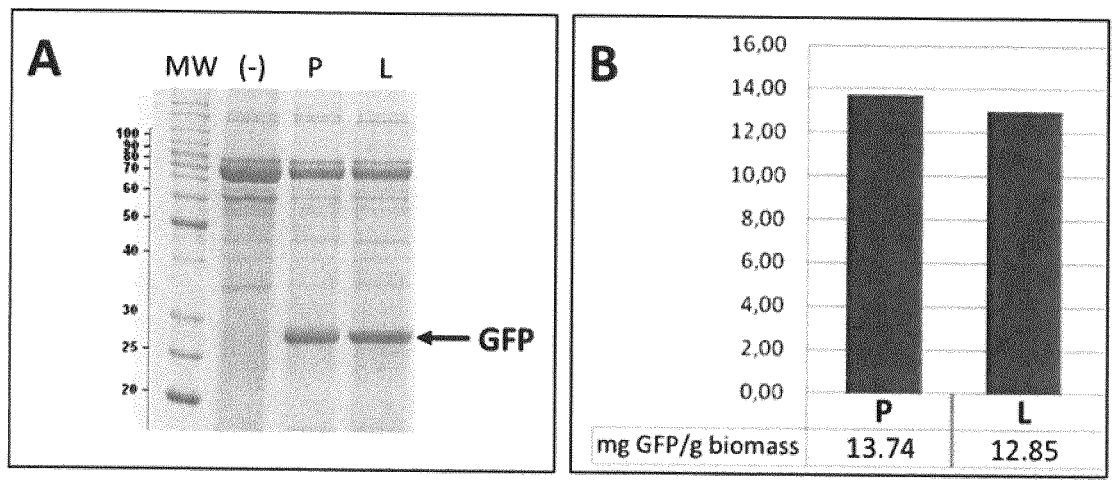
FIG. 11: Comparative analysis of the expression yields of the GFP protein in infected pupae and larvae. A) Coomassie blue staining of a SDS-PAGE resolving protein extracts from infected pupae (P) or infected larvae (L) with the TB(+) baculovirus. (-) corresponds to an extract from an uninfected control pupa. B) Quantification of the GFP production yields obtained in infected pupae or larvae and expressed in mg per g of insect biomass.
Figure 12:
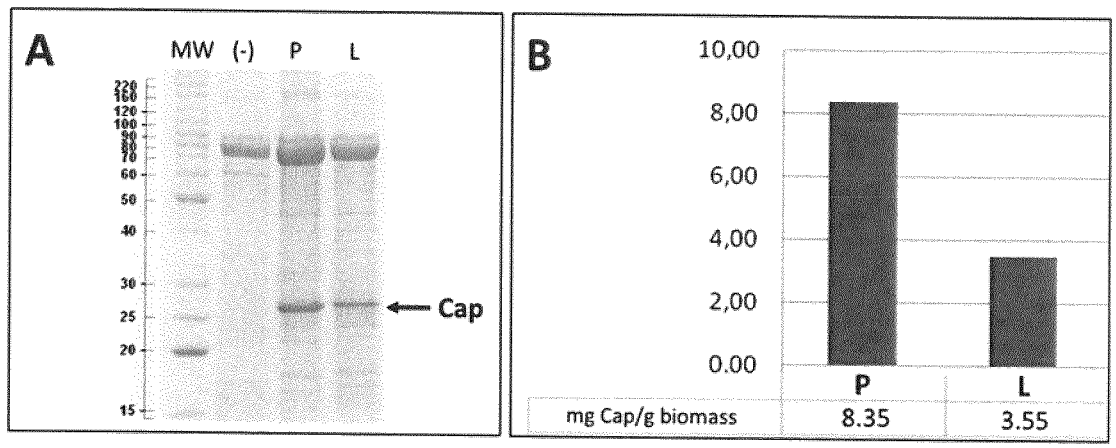
FIG. 12: Comparative analysis of the expression yields of the Cap protein in infected pupae and larvae. A) Coomassie blue staining of a SDS-PAGE resolving protein extracts from infected pupae (P) or infected larvae (L) with the TB(+) baculovirus. (-) corresponds to an extract from a uninfected control pupa. B) Quantification of the Cap production yields obtained in infected pupae or larvae and expressed in mg per g of insect biomass.
Figure 13:
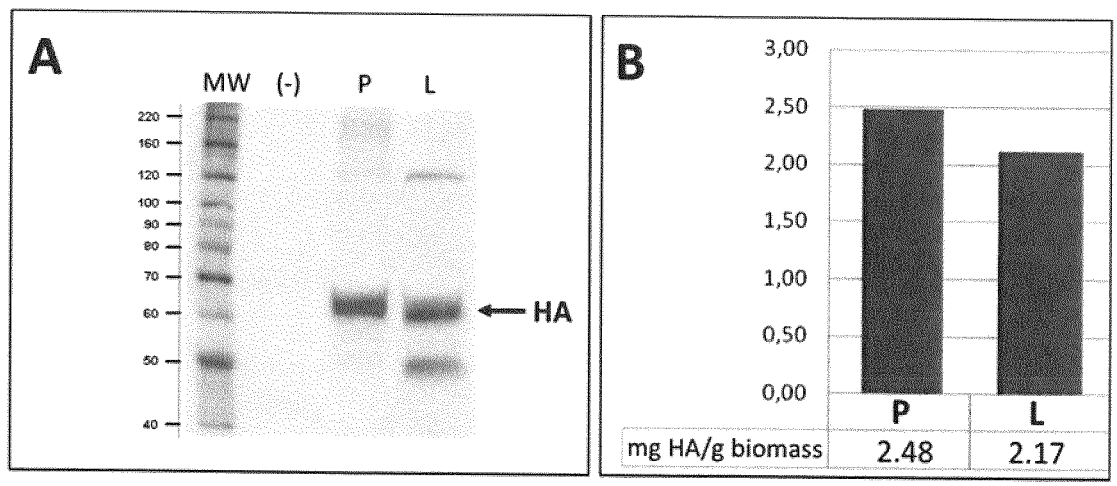
FIG. 13: Comparative analysis of the expression yields of the HA protein in infected pupae and larvae. A) Coomassie blue staining of a SDS-PAGE resolving protein extracts from infected pupae (P) or infected larvae (L) with the TB(+) baculovirus. (-) corresponds to an extract from an uninfected control pupa. B) Quantification of the HA production yields obtained in infected pupae or larvae and expressed in mg per g of insect biomass.

Example 4. Production of Recombinant Proteins in Baculovirus Infected T. ni Pupae is More Efficient than Larvae The comparative expression of five recombinant proteins in TB(+) baculoviruses in T. ni pupae and larvae was carried out. The expressed proteins were the following: GFP (SEQ ID NO.: 23), Cap (SEQ ID NO.: 25), HA (SEQ ID NO.: 30) and the VP60 (capsid protein) from two rabbit hemorrhagic calicivirus strains (RHDV genogroup 1 and RHDVb; SEQ ID NOs: 32 and 33) (FIG. 10). Pupae and larvae were infected with 50,000 PFUs of the corresponding TB(+) baculoviruses. Infected insects (larva and pupa) were collected at 96 h post-infection. Soluble protein extracts were analyzed by SDS-PAGE electrophoresis stained with Coomassie blue (FIGS. 11A, 12A, 13A and 14A). Recombinant proteins were quantified by densitometry using a BSA curve and production yields were expressed as milligrams per biomass unit (FIGS. 11B, 12B, 13B and 14B). In all cases, pupae expressed higher quantities of recombinant protein than larva, with increasing ratios from 1.06 to 3.64.

Example 5. Production of Recombinant Virus-Like Particles (VLPs) in T. ni Pupae

To demonstrate the production of VLPs in infected pupae, protein extracts from infected pupae with the TB(+) baculoviruses expressing the VP60 protein from the two rabbit calicivirus strains analyzed in Example 4 were processed for VLPs purification. The VLPs were extracted from infected pupae at 96 h post-infection by centrifugation in the presence of detergents (2% sarkosyl (Sigma) and 5 mM EDTA (Sigma) in a PBS (0.2 M sodium phosphate, 0.1 M NaCl, pH 6.0) and protease inhibitors (Complete®, Roche) and incubated overnight at 4° C. Then, they were treated with DNAse I (Roche Diagnostics) for 1 h at 37° C. After an additional centrifugation (2,000×g, 5 min), supernatants were subjected to ultracentrifugation (131,453×g; 2.5 h). Sediments were extracted twice in Vertrel (Sigma) and submitted to second ultracentrifugation (131,453×g; 2.5 h). Finally, sediments were resuspended in PBS 1× and stored at 4° C. until analysis.

Figure 14:
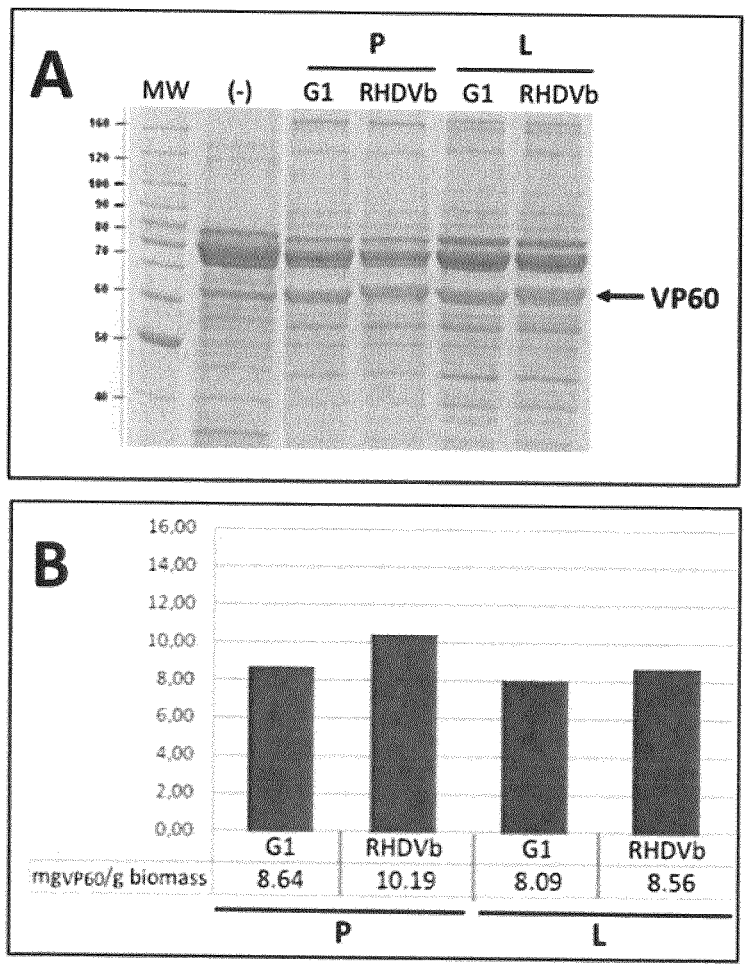
FIG. 14: Comparative analysis of the expression yields of the RHDV capsid VP60 proteins (G1 and RHDVb) in infected pupae and larvae. A) Coomassie blue staining of a SDS-PAGE resolving protein extracts from infected pupae (P) or infected larvae (L) with the TB(+) baculovirus. (−) corresponds to an extract from an uninfected control pupa. B) Quantification of the RHDV capsid proteins production yields obtained in infected pupae or larvae and expressed in mg per g of insect biomasses (L) with the TB(+) baculovirus. (−) corresponds to an extract from an uninfected control pupa. B) Quantification of the RHDV capsid proteins production yields obtained in infected pupae or larvae and expressed in mg per g of insect biomass.
Figure 15:
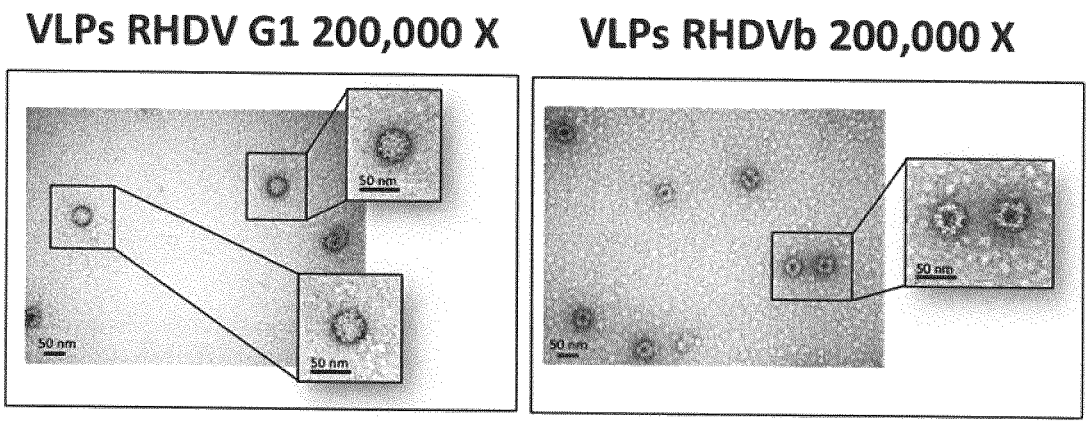
FIG. 15: VLPs formed after infection of T. ni pupae a TB (+) baculovirus expressing the VP60 protein from the RHDV G1 and RHDVb. Extracts from infected pupae at the optimal production times with each baculovirus were processed for VLP purification. Samples were observed by Electron microscopy using negative staining. The figure shows the VLPs at two magnifications. VLPs obtained with the two baculoviruses presented identical sizes and shapes. The micrographs are representative of the fields analyzed.

Sediments were analyzed by transmission electron microscopy performed by conventional means. Briefly, purified VLPs (approximately 5 were applied to glow-discharged carbon-coated grids for 2 min. Samples were negatively stained with 2% (w/v) aqueous uranyl acetate. Micrographs were recorded with an EM 2000 Ex microscope (JEOL, Japan). As shown in FIG. 14, VLPs of the expected size and shape corresponding to RHDV were observed, demonstrating that a corrected folding and self-assembling is carried out in the baculovirus-infected pupae tissues (FIG. 15).

Example 6. Virus Inoculum Production in Infected T. ni Pupae

Spodoptera frugiperda (Sf21 and Sf9) cell lines were cultured at 27° C. in TNMFH medium (PAN Biotech GmbH, Germany) with 10% heat-inactivated fetal bovine serum (PAN Biotech GmbH) and gentamicin (50 µg/ml) (PAN Biotech GmbH). Cell density and viability were assessed by Trypan blue staining. Cell viability was calculated on the basis of the percentage of living cells with respect to the total number of cells at various times post-infection.

The Sf9 cells, which were cultured in suspension, were infected in spinner flasks (80 ml of culture media) at a cell density of $2\times10^6$ cells/ml. Cell viability at the time of infection was >99% in suspension. Sf9 cells were infected in vitro with recombinant baculoviruses at a multiplicity of infection (MOI) of 0.01 to 0.1. After 72-96 h post-infection, the virus inoculum was recovered from supernatants after centrifugation. The virus titer was calculated by a plaque forming unit (pfu) assay, obtaining virus titers between $10^7$ to $10^8$ viruses per ml.

Figure 16:
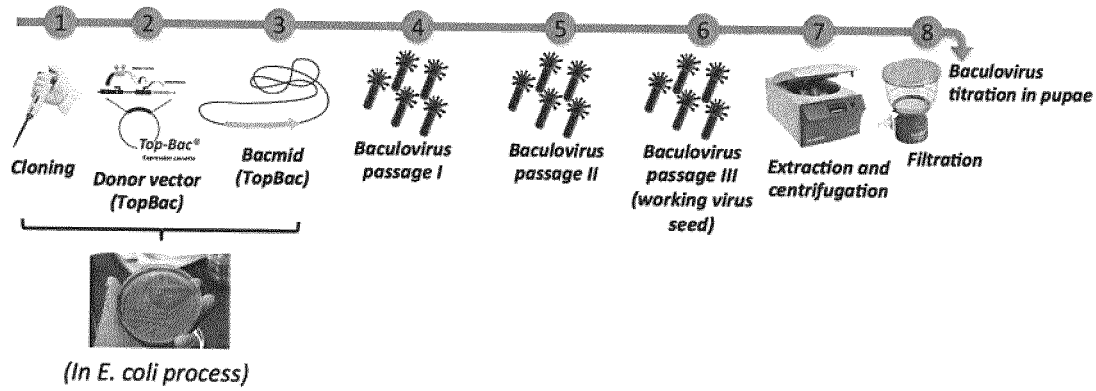
FIG. 16: Schematic example of procedure to obtain a virus inoculum from infected pupae in absence of insect cell cultures.

The viruses were used to infect T. ni pupae with doses ranging from $5\times10^2$ to $10^4$ pfu. After 3-7 days, the pupae were homogenized to collect the infective virus in cell culture media or in a specific PBS buffer containing DTT and protease inhibitor PMSF. Pupae homogenates were centrifuged to eliminate the pupae debris at 5,000×g during 30 min. Then, the supernatant containing the virus was filtered sequentially by a filter of 0.45 and 0.22 microns and the resulting virus preparation was preserved by mixing with glycerol and then it could be frozen or lyophilized. The virus stocks were titrated in T. ni fifth instar larvae using the Karber method concretely, LID50 (larvae infectious dose 50). The statistical meaning of one infectious dose calculated in this way is that a population of larvae infected with an ID50 will show a 50% of individual infected. Larvae were observed for at least 96 h in order to detect clinical signs and to follow their evolution to pupa. Typical virus titers were between $10^6$ to $10^8$ pfu/ml of virus preparation. Additionally, baculovirus inoculum can be obtained without a previous baculovirus vector generation in cell cultures. Pupae can be transfected with a bacmid obtained in bacteria by a transposition procedure. FIG. 16 represents the general procedure to obtain a virus stock in pupa by a cell-free system.

Example 7. Cell Culture and Viruses

The Spodoptera frugiperda Sf21 or SP cell lines were cultured in 6-well tissue culture plates ($1\times10^6$ cells/well) in TNM-FH insect medium (Pan Biotech™, Germany) containing 10% heat-inactivated fetal bovine serum (Pan Biotech™, Germany) at 27° C. AcMNPV recombinant baculoviruses were obtained by the "Bac-to-Bac" Baculovirus Expression System (Invitrogen™, USA). The different TB(+) transfer vectors containing the recombinant DNA regulatory elements were generated using the pFastBac™-DUAL plasmid (Invitrogen™). These transfer vectors were used to transfect Sf21 cells with Cellfectin® (Invitrogen™, USA). The resulting recombinant baculoviruses from the infection of Sf21 cells were then passaged twice in cells and titered by the plaque assay method. The obtained gene constructs of the TB (+) baculovirus expression cassettes are schematically shown in FIGS. 4, 7 and 10, showing the combinations of genetic regulatory elements involved in the genes expression (polhAc-ie-01/hr1p6.9p10, SEQ ID NO.: 17, plus the sequence of the gene coding for the desired protein, e.g., SEQ ID NOs: 26, 30, 32 and 33). The different expression cassettes were used to generate the recombinant baculoviruses used in the examples shown in FIGS. 6, 8, 9, 11, 12, 13, and 14.

Example 8. Generation of the Cloning Vector

The cloning vector is a small piece of DNA containing the TB(+) baculovirus expression cassette into which a foreign DNA fragment can be inserted by treating the vehicle and the foreign DNA with a restriction enzyme that creates the same overhang, then ligating the fragments together. The essential characteristics of the cloning vector are that it must include a synthetic multiple cloning site (MCS) to facilitate the insertion of foreign genes directed in a chosen orientation, a selectable marker, such as an antibiotic resistance to allow the selection of positively transformed cells and a functional origin of replication (ORI) for propagation in bacteria

Example 9. Generation of the Donor Vector Containing the Baculovirus Expression Cassette of the Present Invention A donor vector consists of a cloning vector, for example a pUC57 plasmid, containing the baculovirus expression cassette, into which a foreign gene has been cloned using the appropriate restriction enzymes. The TB(+) baculovirus expression cassette used was synthesized by ligating the following DNA sequences: (i) the baculovirus transcriptional regulator encoding sequence Ac-ie-01 (e.g., SEQ ID NOs: 1-5) downstream of a promoter sequence, such as the polh promoter (e.g., SEQ ID NO.: 10), and upstream of the HSV TK polyadenylation signal and (ii) in another locus an enhancer sequence, for example, the homologous region hr1, upstream of (iii) a promoter sequence, for example, p6.9p10 (e.g., SEQ ID NO.: 13), followed by a multiple cloning site (MCS) for cloning the gene of interest and the p10 polyadenylation signal downstream of the MCS (FIGS. 4, 7 and 10). The baculovirus expression cassette is flanked by specific restriction sites (for example BgIII and BstZ17I at the 5'-terminal end and Bgl II and Sgf I at the 3'-terminal end) to facilitate subcloning into a transfer vector of a commercial baculovirus generation system (based on transposition, for example the "Bac-to-Bac®" system (Invitrogen™), or based on homologous recombination, for example "flashBAC™" (Oxford Expression Technologies™). "Baculogold™" (BD Biosciences™), "BacPAK6™" (Clontech™), "Bac-N-Blue DNA™" (Invitrogen™).

The encoding foreign genes were cloned into the MCS of the cloning vector using the Nco I and Spe I restriction sites, generating the donor plasmid vectors.

Example 10. Generation of the Transfer Vector Containing the Baculovirus Expression Cassette of the Present Invention The transfer vector was generated by digesting a donor vector with BstZ17 1 of the 5'-flanking site and with Xba I and cloning it into the transfer vector pFastBac™ 1 that was also digested with the same enzymes. In this case, as a result of the subcloning, the SV40 polyadenylation signal of the baculovirus expression cassette is exchanged by the p10 polyadenylation signal from the transfer vector. Apart from this, all the elements of the expression cassette are included in the pFastBac transfer vector, substituting the polh promoter and MCS of the original commercial transfer vector.

Example 11. Generation of the Baculovirus Expression Vector Containing the Baculovirus Expression Cassette of the Present Invention Using the "Bac-to-Bac®" System The modified transfer vector pFastBac™1 and the TB(+) baculovirus expression cassette were used to generate the recombinant baculovirus by using the "Bac-to-Bac®" Baculovirus Expression System. More specifically, the modified transfer vector was used to transform the *E. coli* host strain DH10Bac™ that contains a baculovirus shuttle vector (bacmid) and a helper plasmid, and allows the generation of a recombinant bacmid following transposition of the expression cassette. The DNA of the recombinant bacmid containing the TB(+) baculovirus expression cassette of the present invention and the different foreign encoding genes were then used to transfect insect cells, for example, Sf21 cells, using Cellfectin®. Also the bacmid was used to transfect insect pupae. *Trichoplusia ni* (Cabbage looper) pupae at an age of 1 to 5 days were used for this experiment. 72 hours post-transfection, cells or pupae were harvested or processed and the first recombinant baculovirus generation was obtained. This recombinant baculovirus could then be further amplified and/or titered following conventional protocols. Similar procedures can be used to generate recombinant baculoviruses with other transfer vectors provided by commercial BEVSs.

Example 12. Infection of Insect Pupae

*Trichoplusia ni* (Cabbage looper) pupae at an age of 1 to 5 days were used for all experiments. The standard weight of each pupa was approximately 200-300 mg and pupae were injected manually or by a specifically designed robot with 1 to 10 µl of recombinant baculoviruses diluted in cell culture media or PBS 1× as to reach the number of plaque forming units (PFU) per dose selected. Pupae were collected at 72-168 h post-infection. The pupae collected were frozen immediately to be stored at −20° C. or −80° C. until they were processed for recombinant protein quantification. Total soluble, non-denatured proteins (TSNDPs) from frozen *T. ni* pupae infected by the baculoviruses were obtained by homogenization in presence of a extraction buffer using a blender or a homogenizer mixer for several min.

Example 13. Downstream Processing of Insect Pupae

Frozen pupae are disrupted by a homogenizer to obtain a crude extract containing a reducing agent in a concentration of 1-25 mM, a detergent in a concentration of 0.01%-2% and a mixture of protease inhibitors. The viscosity of the crude extract is reduced by its incubation with a diatomaceous earth for a specific period of time and then centrifuged to eliminate the insect debris and filtered to eliminate the diatomaceous earth. Then, the extract is clarified through tangential flow filtration using an appropriate filter depending of the recombinant protein nature. Finally, a diafiltration process is performed in the same tangential filtration device to change the buffer before further chromatography purification. FIG. 17 represents the general procedure to obtain a soluble recombinant protein extract from baculovirus-infected pupae.

Items of the present invention (I):

1. A pupa comprising a recombinant baculovirus and/or a bacmid derived from *Autographa californica* multicapsid nucleopolyhedrovirus (AcMNPV).

2. The pupa according to item 1, wherein the pupa belongs to the order Lepidoptera.

3. The pupa according to item 1, wherein the pupa belongs to the genera *Trichoplusia, Rachiplusia, Spodoptera, Heliothis, Manduca, Helicoverpa, Ascalapha* or *Samia*, preferably to the species *Trichoplusia ni, Manduca sexta, Spodoptera frugiperda, Spodoptera Ascalapha odorata,*

*Helicoverpa zea, Heliothis virescens, Rachiplusia nu* or *Samia cynthia*, or any other pupa susceptible to be infected by a recombinant baculovirus and/or a bacmid derived from AcMNPV.

4. The pupa according to any one of items 1 to 3, wherein the baculovirus comprises a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein.

5. A pupa comprising a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein.

6. The pupa according to item 5, wherein the pupa belongs to the order Lepidoptera.

7. The pupa according to item 6, wherein the pupa belongs to the genera *Trichoplusia, Rachiplusia, Spodoptera, Heliothis, Manduca, Helicoverpa, Ascalapha* or *Samia*, preferably to the species *Trichoplusia ni, Manduca sexta, Spodoptera frugiperda, Spodoptera litoralis, Ascalapha odorata, Helicoverpa zea, Heliothis virescens, Rachiplusia nu* or *Samia cynthia*, or any other pupa susceptible to be infected by a recombinant baculovirus and/or a bacmid derived from AcMNPV.

8. The pupa according to any one of items 1 to 7, wherein the pupa belongs to the species *Trichoplusia ni*.

9. The pupa according to any one of items 4 to 8, wherein the nucleic acid sequence that allows for the expression of the proteins IE-1, IE-0 and/or fragments thereof is selected from the group consisting of:
  (a) a nucleic acid containing the nucleotide sequence indicated in any of SEQ ID NOs: 1-5;
  (b) a nucleic acid sequence having a sequence identity of at least 70%, preferably at least 75%, more preferably at least 80%, more preferably at least 85%, more preferably at least 90% and most preferably at least 95% with the nucleotide sequence indicated in any of SEQ ID NOs: 1-5 and encoding a protein able to function as a transcriptional regulator in a recombinant baculovirus;
  (c) a nucleic acid sequence encoding an amino acid containing the amino acid sequence indicated in any of SEQ ID NOs: 6-9; and
  (d) a nucleic acid sequence encoding an amino acid sequence having a sequence similarity of at least 70%, preferably at least 75% more preferably at least 80%, more preferably at least 85%, more preferably at least 90% and most preferably at least 95% with the amino acid sequence indicated in any of SEQ ID NOs: 6-9 and able to function as a transcriptional regulator in a recombinant baculovirus.

10. The pupa according to any one of items 4 to 9, wherein the promoter that drives the expression of said recombinant protein is, selected from the group of nucleic acids comprising:
  (a) a nucleic acid containing the nucleotide sequence indicated in any of SEQ ID NOs: 10-14, preferably indicated in any of SEQ ID NOs: 11-13; and
  (b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NOs: 10-14, preferably indicated in any of SEQ ID NOs: 11-13.

11. The pupa according to any one of items 4 to 10, wherein the recombinant homologous region (hr) is the sequence indicated in SEQ ID NO: 21 (hr1).

12. The pupa according to any one of items 4 to 11, wherein the nucleic acid sequence that comprises combinations of recombinant promoters, sequences encoding transcriptional regulators and enhancer regions are selected from the group comprising SEQ ID NOs: 15-20.

13. The pupa according to any one of items 4 to 12, wherein the pupa further comprises a nucleic acid sequence encoding a recombinant protein.

14. The pupa according to item 13, wherein the recombinant protein is selected from the group consisting of subunit monomeric vaccine, subunit multimeric vaccine, virus like particle, therapeutic protein, antibody, enzyme, cytokine, blood clotting factor, anticoagulant, receptor, hormone, diagnostic protein reagents and the green fluorescent protein (GFP).

15. The pupa according to item 14, wherein the recombinant protein is a virus-like particle protein selected from the group consisting of:
  (a) Porcine circovirus capsid protein, preferably from porcine circovirus type 2 (e.g., SEQ ID NO.: 26),
  (b) Foot and mouth disease virus VP1, VP3 or VP0 protein,
  (c) Canine parvovirus VP1 and VP2 proteins,
  (d) Porcine parvovirus VP1 and VP2 proteins,
  (e) Human norovirus (genogroup I or II) capsid protein,
  (f) Calicivirus capsid protein,
  (g) Human papillomavirus L1 protein, preferably from human papillomavirus 16,
  (h) Hepatitis E protein E2,
  (i) Infectious bursal disease virus VP1, VP2 and VP3 proteins,
  (j) Astrovirus ORF2-encoded proteins,
  (k) Influenza virus HA (e.g., SEQ ID NO.: 30), NA and M1 proteins,
  (l) Hepatitis B core and surface antigens,
  (m) Human parvovinis VP1 and VP2 proteins, and
  (n) Rabbit calicivirus VP60 protein, preferably from rabbit haemorrhagic disease virus (e.g., SEQ ID NOs: 32 and 33).

16. Use of the pupa as defined in any one of items 1 to 15 for the expression of recombinant proteins.

17. The use according to item 16, wherein the recombinant protein is selected from the group consisting of subunit monomeric vaccine, subunit multimeric vaccine, virus like particle, therapeutic protein, antibody, enzyme, cytokine, blood clotting factor, anticoagulant, receptor, hormone, diagnostic protein reagents and the green fluorescent protein (GFP).

18. The use according to item 17, wherein the recombinant protein is a virus-like particle protein selected from the group consisting of:
  (a) Porcine circovirus capsid protein, preferably from porcine circovirus type 2 (e.g., SEQ ID NO.: 26),
  (b) Foot and mouth disease virus VP1, VP3 or VP0 protein,
  (c) Canine parvovirus VP1 and VP2 proteins,
  (d) Porcine parvovirus VP1 and VP2 proteins,
  (e) Human norovirus (genogroup I or II) capsid protein,
  (f) Calicivirus capsid protein, (g) Human papillomavirus L1 protein, preferably from human papillomavirus 16,
(h) Hepatitis E protein E2,
(i) Infectious bursal disease virus VP1, VP2 and VP3 proteins,
(j) Astrovirus ORF2-encoded proteins,
(k) Influenza virus HA (e.g., SEQ ID NO.: 30), NA and M1 proteins,
(l) Hepatitis B core and surface antigens,
(m) Human parvovirus VP1 and VP2 proteins, and
(n) Rabbit calicivirus VP60 protein, preferably from rabbit haemorrhagic disease virus (e.g., SEQ ID NOs: 32 and 33).

19. A method for producing at least one recombinant protein comprising the steps of:
(a) Providing a pupa;
(b) Inoculating the pupa of step (a) with a recombinant baculovirus derived from *Autographa californica* multicapsid nucleopolyhedrovirus (AcMNPV);
(c) Incubating the inoculated pupa of step (b) for a period of time sufficient for the at least one recombinant protein to be expressed;
(d) Obtaining the pupae comprising the at least one recombinant protein;
(e) Optionally, harvesting the at least one recombinant protein; and
(f) Optionally, purifying the at least one recombinant protein.

20. The method according to item 19, wherein the pupa belongs to the order Lepidoptera.

21. The method according to item 20, wherein the pupa belongs to the genera *Trichoplusia, Rachiplusia, Spodoptera, Manduca, Helicoverpa, Ascalapha* or *Samia*, preferably to the species *Trichoplusia ni, Manduca sexta, Spodoptera frugiperda, Spodoptera litoralis, Ascalapha odorata, Helicoverpa zea, Heliothis virescens, Rachiplusia nu* and, *Samia cynthia*, or any other pupa susceptible to be infected by a recombinant baculovirus and/or a bacmid derived from AcMNPV.

22. The method according to item 21, wherein the pupa belongs to the species *Trichoplusia ni*.

23. The method according to any one of items 19 to 22, wherein the recombinant baculovirus comprises a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein.

24. The method according to item 23, wherein the nucleic acid sequence that allows for the expression of the proteins IE-1, IE-0 and/or fragments thereof is selected from the group consisting of:
(a) a nucleic acid containing the nucleotide sequence indicated in any of SEQ ID NO: 1-5;
(b) a nucleic acid sequence having a sequence identity of at least 70%, preferably at least 7.5%, more preferably at least 80%, more preferably at least 85%, more preferably at least 90% and most preferably at least 95% with the nucleotide sequence indicated in any of SEQ ID NO: 1-5 and encoding a protein able to function as a transcriptional regulator in a recombinant baculovirus;
(c) a nucleic acid sequence encoding an amino acid containing the amino acid sequence indicated in any of SEQ ID NO: 6-9; and
(d) a nucleic acid sequence encoding an amino acid sequence having a sequence similarity of at least 70%, preferably at least 75%, more preferably at least 80%, more preferably at least 85%, more preferably at least 90% and most preferably at least 95% with the amino acid sequence indicated in any of SEQ ID NO: 6-9 and able to function as a transcriptional regulator in a recombinant baculovirus.

25. The method according to any one of items 23 to 24, wherein the promoter that drives the expression of said recombinant protein is, selected from the group of nucleic acids comprising:
(a) a nucleic acid containing the nucleotide sequence indicated in any of SEQ ID NO: 10-14, preferably indicated in any of SEQ ID NOs: 11-13; and
(b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NO: 10-14, preferably indicated in any of SEQ ID NOs: 11-13.

26. The method according to any one of items 23 to 25, wherein the recombinant homologous region (hr) is the sequence indicated in SEQ ID NO: 21 (hr1).

27. The method according to any one of items 23 to 26, wherein the nucleic acid sequence that comprises combinations of recombinant promoters, sequences encoding transcriptional regulators and enhancer regions are selected from the group comprising SEQ ID NO: 15-20.

28. The method according to any one of items 19 to 27, wherein the pupa further comprises a nucleic acid sequence encoding a recombinant protein.

29. The method according to item 28, wherein the recombinant protein is selected from the group consisting of subunit monomeric vaccine, subunit multimeric vaccine, virus like particle, therapeutic protein, antibody, enzyme, cytokine, blood clotting factor, anticoagulant, receptor, hormone, diagnostic protein reagents and the green fluorescent protein (GFP).

30. The method according to item 29, wherein the recombinant protein is a virus-like particle protein selected from the group consisting of:
(a) Porcine circovirus capsid protein, preferably from porcine circovirus type 2 (e.g., SEQ ID NO.: 26),
(b) Foot and mouth disease virus VP1, VP3 or VP0 protein,
(c) Canine parvovirus VP1 and VP2 proteins,
(d) Porcine parvovirus VP1 and VP2 proteins,
(e) Human norovirus (genogroup I or II) capsid protein,
(f) Calicivirus capsid protein,
(g) Human papillomavirus L1 protein, preferably from human papillomavirus 16,
(h) Hepatitis E protein E2,
(i) Infectious bursal disease virus VP1, VP2 and VP3 proteins,
(j) Astrovirus ORF2-encoded proteins,
(k) Influenza virus HA (e.g., SEQ ID NO.: 30), NA and M1 proteins,
(l) Hepatitis B core and surface antigens,
(m) Human parvovirus VP1 and VP2 proteins, and
(n) Rabbit calicivirus VP60 protein, preferably from rabbit haemorrhagic disease virus (e.g., SEQ ID NOs: 32 and 33).

31. The method according to any one of items 19 to 30, wherein the pupa is a silk-free pupa.

32. The method according to item 31, wherein the silk-free pupa is obtainable by dissolving the silk of cocoons comprising the pupae of *T. ni* with a solution of a salt of hypochlorous acid, preferably sodium hypochlorite.

33. The method according to any one of items 19 to 32, wherein the inoculation of the pupa with a recombinant baculovirus is performed by injecting the baculovirus into the pupa.

34. The method according to any one of items 19 to 33, wherein the inoculated pupa of step (b) is the pupa as defined in any one of items 1 to 15.

35. The method according to any one of items 19 to 34, wherein the pupa is inoculated with baculovirus in an amount of from 50 to $10^6$ PFUs/pupa.

36. A method for producing a silk-free pupa belonging to the order Lepidoptera comprising the steps of:
    (a) Providing a pupa contained in a cocoon;
    (b) Treating the cocoon containing a pupa with a solution of a salt of hypochlorous acid, preferably sodium hypochlorite; and
    (c) Obtaining a silk-free and disinfected pupa.

37. The method according to item 36, wherein the pupa does not belong to the species *Bombyx mori*.

38. The method according to any one of items 36 to 37, wherein the pupa belongs to the species *Trichoplusia ni*.

39. The method according to any one of items 36-38, wherein the pupae are provided in a matrix (or array).

40. A method for producing a recombinant baculovirus comprising the steps of:
    (a) Providing a pupa;
    (b) Transfecting the pupa of step (a) with a bacmid suitable for producing a recombinant baculovirus derived from *Autographa californica* multicapsid nucleopolyhedrovirus (AcMNPV);
    (c) Incubating the inoculated pupa of step (b) for a period of time sufficient for the recombinant baculovirus is produced;
    (d) Obtaining the pupae comprising the recombinant baculovirus;
    (e) Optionally, harvesting the recombinant baculovirus; and
    (f) Optionally, purifying the recombinant baculovirus.

41. The method according to item 39, wherein the pupa is the pupa as defined in any one of items 36-39.

42. The method according to any one of items 40-41, wherein the pupa belongs to the order Lepidoptera.

43. The method according to item 42, wherein the pupa belongs to the genera *Trichoplusia, Rachiplusia, Spodoptera, Heliothis, Manduca, Helicoverpa, Ascalapha* or *Samia*, preferably to the species *Trichoplusia ni, Manduca semi, Spodoptera frugiperda, Spodoptera litoralis, Ascalapha odorata, Helicoverpa zea, Heliothis virescens, Rachiplusia nu* or *Samia cynthia*, or any other pupa susceptible to be infected by a recombinant baculovirus and/or a bacmid derived from AcMNPV.

44. The method according to item 43, wherein the pupa belongs to the species *Trichoplusia ni*.

45. The method according to any one of items 40 to 44, wherein the bacmid suitable for producing a recombinant baculovirus derived from *Autographa californica* multicapsid nucleopolyhedrovirus (AcMNPV) comprises or alternatively, consists of, a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein.

46. The method according to item 45, wherein the wherein the nucleic acid sequence that allows for the expression of the proteins IE-1, IE-0 and/or fragments thereof is selected from the group consisting of:
    (a) a nucleic acid containing the nucleotide sequence indicated in any of SEQ ID NO: 1-5;
    (b) a nucleic acid sequence having a sequence identity of at least 70%, preferably at least 75%, more preferably at least 80%, more preferably at least 85%, more preferably at least 90% and most preferably at least 95% with the nucleotide sequence indicated in any of SEQ ID NO: 1-5 and encoding a protein able to function as a transcriptional regulator in a recombinant baculovirus;
    (c) a nucleic acid sequence encoding an amino acid containing the amino acid sequence indicated in any of SEQ ID NO: 6-9; and
    (d) a nucleic acid sequence encoding an amino acid sequence having a sequence similarity of at least 70%, preferably at least 75%, more preferably at least 80%, more preferably at least 85%, more preferably at least 90% and most preferably at least 95% with the amino acid sequence indicated in any of SEQ ID NO: 6-9 and able to function as a transcriptional regulator in a recombinant baculovirus.

47. The method according to any one of items 45 to 46, wherein the promoter that drives the expression of said recombinant protein is, selected from the group of nucleic acids comprising:
    (a) a nucleic acid containing the nucleotide sequence indicated in any of SEQ ID NO: 10-14, preferably indicated in any of SEQ ID NOs: 11-13; and
    (b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NO: 10-14, preferably indicated in any of SEQ ID NOs: 11-13.

48. The method according to any one of items 45 to 47, wherein the recombinant homologous region (hr) is the sequence indicated in SEQ ID NO: 21 (hr1).

49. The method according to any one of items 45 to 48, wherein the nucleic acid sequence that comprises combinations of recombinant promoters, sequences encoding transcriptional regulators and enhancer regions are selected from the group comprising SEQ ID NO: 15-20.

50. The method according to any one of items 40 to 49, wherein the pupa is a silk free pupa.

51. The method according to item 50, wherein the silk-free pupa is obtainable by dissolving the cocoons comprising the pupae of *T. ni* with a solution of a salt of hypochlorous acid, preferably sodium hypochlorite.

52. The method according to any one of items 40 to 51, wherein the transfected pupa of step (b) is the pupa as defined in any one of items 5 to 15.

53. The method according to any one of items 40 to 52, wherein the pupae are provided in a matrix.

54. A device comprising a precision pump, a mobile mechanic arm and a (removable) needle suitable for injecting a fluid into a pupa belonging to the order Lepidoptera, preferably to the genera *Trichoplusia, Rachiplusia, Spodoptera, Heliothis, Manduca, Helicoverpa, Ascalapha* or *Samia*, more preferably to the species *Trichoplusia ni, Manduca*

*sexta, Spodoptera frugiperda, Spodoptera litoralis, Ascalapha odorata, Helicoverpa zea, Heliothis virescens, Rachiplusia nu* or *Samia cynthia*, or any other pupa susceptible to be infected by a recombinant baculovirus and/or a bacmid derived from AcMNPV.

55. The device according to item 54, wherein the pupa is provided in a matrix or array.

56. The device according to any one of items 54 to 55, wherein the device further comprises a computer program for defining the position of the needle and/or for calculating the distance from the needle to the pupa and/or the distance of penetration of the needle into the pupa and/or the volume of liquid to be inoculated into the pupa and/or determining the coordinates of the inoculation needle and/or calculating the inoculation volume and/or time and/or the time between inoculation of the pupae.

57. The device according to item 56, further comprising a computer program for calculating the inoculation time and/or the time between inoculation of the pupae.

58. The device according to any one of items 54 to 57, wherein the device further comprises a camera for defining the position of the needle.

59. The device according to item 54, wherein the pupa is the pupa as defined in any one of items 1 to 15.

60. The device according to any one of items 54 to 59, wherein the injected fluid comprises a recombinant baculovirus or bacmid.

61. The device according to any one of items 54 to 60, wherein the device is suitable for performing step (b) as defined in any one of items 19 and/or 40.

62. The device according to any one of items 54 to 61, wherein the injected fluid into the pupa is in the range of from about 0.5 to about 10.0 µL, preferably about 5 µL.

63. The device according to any one of items 54 to 62, wherein the needle penetrates into the pupa a distance of from about 1 to about 5 mm, preferably about 3 mm.

64. The device according to any one of items 54 to 63, wherein the fluid injected into the pupa comprises baculovirus, preferably in an amount of from 50 to $10^6$ PFUs/dose injected into each pupa.

Items of the present invention (II):

1. A pupa comprising a recombinant baculovirus and/or a bacmid derived from *Autographa californica* multicapsid nucleopolyhedrovirus (AcMNPV), wherein preferably the pupa belongs to the order Lepidoptera, preferably to the genera *Trichoplusia, Rachiplusia, Spodoptera, Heliothis, Manduca, Helicoverpa, Ascalapha* or *Samia*, even more preferably to the species. *Trichoplusia ni, Manduca sexta, Spodoptera frugiperda, Spodoptera litoralis, Ascalapha odorata, Helicoverpa zea, Heliothis virescens, Rachiplusia nu* or *Samia cynthia*, or any other pupa susceptible to be infected by a recombinant baculovirus and/or a bacmid derived from AcMNPV.

2. The pupa according to item 1, wherein the baculovirus comprises a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein.

3. A pupa comprising a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein, wherein preferably the pupa belongs to the order Lepidoptera, preferably to the genera *Trichoplusia, Rachiplusia, Spodoptera, Heliothis, Manduca, Helicoverpa, Ascalapha* or *Samia*, even more preferably to the species *Trichoplusia ni, Manduca sexta, Spodoptera frugiperda, Spodoptera litoralis, Ascalapha odorata, Helicoverpa zea, Heliothis virescens, Rachiplusia nu* or *Samia cynthia*, or any other pupa susceptible to be infected by a recombinant baculovirus and/or a bacmid derived from AcMNPV.

4. The pupa according to any one of items 2 to 3, wherein the nucleic acid sequence that allows for the expression of the proteins IE-1, IE-0 and/or fragments thereof is selected from the group consisting of:
   (a) a nucleic acid containing the nucleotide sequence indicated in any of SEQ ID NOs: 1-5;
   (b) a nucleic acid sequence having a sequence identity of at least 70%, preferably at least 75%, more preferably at least 80%, more preferably at least 85%, more preferably at least 90% and most preferably at least 95% with the nucleotide sequence indicated in any of SEQ ID NOs: 1-5 and encoding a protein able to function as a transcriptional regulator in a recombinant baculovirus;
   (c) a nucleic acid sequence encoding an amino acid containing the amino acid sequence indicated in any of SEQ ID NOs: 6-9; and
   (d) a nucleic acid sequence encoding an amino acid sequence having a sequence similarity of at least 70%, preferably at least 75%, more preferably at least 80%, more preferably at least 85%, more preferably at least 90% and most preferably at least 95% with the amino acid sequence indicated in any of SEQ ID NOs: 6-9 and able to function as a transcriptional regulator in a recombinant baculovirus;
wherein the promoter that drives the expression of said recombinant protein is, selected from the group of nucleic acids comprising:
   (a) a nucleic acid containing the nucleotide sequence indicated in any of SEQ ID NOs: 10-14, preferably indicated in any of SEQ ID NOs: 11-13; and
   (b) a nucleic acid sequence able to function as a promoter in a recombinant baculovirus and having a sequence identity of at least 70%, preferably at least 75%, more preferably at least 80%, more preferably at least 85%, more preferably at least 90% and most preferably at least 95% with the nucleotide sequence indicated in any of SEQ ID NOs: 10-14, preferably indicated in any of SEQ ID NOs: 11-13; and
wherein the recombinant homologous region (hr) is the sequence indicated in SEQ ID NO: 21 (hr1).

5. The pupa according to any one of items 2 to 4, wherein the nucleic acid sequence that comprises combinations of recombinant promoters, sequences encoding transcriptional regulators and enhancer regions are selected from the group comprising SEQ ID NOs: 15-20.

6. The pupa according to any one of items 2 to 5, wherein the pupa further comprises a nucleic acid sequence encoding a recombinant protein, preferably selected from the group consisting of subunit monomeric vaccine, subunit multimeric vaccine, virus like particle, therapeutic protein, antibody, enzyme, cytokine, blood clotting factor, anticoagulant, receptor, hormone, diagnostic protein reagents and the green fluorescent protein (GFP).

7. Use of the pupa as defined in any one of items 1 to 6 for the expression of recombinant proteins, preferably selected from the group consisting of subunit monomeric vaccine, subunit multimeric vaccine, virus like particle, therapeutic protein, antibody, enzyme, cytokine, blood clotting factor, anticoagulant, receptor, hormone, diagnostic protein reagents and the green fluorescent protein (GFP).

8. A method for producing at least one recombinant protein comprising the steps of:
   (a) Providing a pupa, preferably a silk-free pupa;
   (b) Inoculating the pupa of step (a) with a recombinant baculovirus derived from *Autographa californica* multicapsid nucleopolyhedrovirus (AcMNPV);
   (c) Incubating the inoculated pupa of step (b) for a period of time sufficient for the at least one recombinant protein to be expressed;
   (d) Obtaining the pupae comprising the at least one recombinant protein;
   (e) Optionally, harvesting the at least one recombinant protein; and
   (f) Optionally, purifying the at least one recombinant protein,
wherein preferably the pupa belongs to the order Lepidoptera, preferably to the genera *Trichoplusia, Rachiplusia, Spodoptera, Heliothis, Manduca, Helicoverpa, Ascalapha* or *Samia*, even more preferably to the species *Trichoplusia ni, Manduca sexta, Spodoptera frugiperda, Spodoptera litoralis, Ascalapha odorata, Helicoverpa zea, Heliothis virescens, Rachiplusia nu* and, *Samia cynthia*, or any other pupa susceptible to be infected by a recombinant baculovirus and/or a bacmid derived from AcMNPV.

9. The method according to item 8, wherein the recombinant baculovirus comprises a nucleic acid sequence that allows for the expression above endogenous levels of the proteins IE1, IE-0 and/or fragments thereof functioning as transcriptional regulators above endogenous levels obtained during baculovirus infection and a recombinant homologous region (hr) operably linked to any promoter that is suitable for driving the expression of a recombinant protein, wherein preferably the nucleic acid sequence that allows for the expression above endogenous levels of the proteins IE-1, IE-0 and/or fragments thereof functioning as transcriptional regulators above endogenous levels obtained during baculovirus infection and the recombinant homologous region (hr) operably linked to any promoter that is suitable for driving the expression of a recombinant protein are as defined in claim 4.

10. The method according to item 11, wherein the nucleic acid sequence that comprises combinations of recombinant promoters, sequences encoding transcriptional regulators and enhancer regions are selected from the group comprising SEQ ID NO: 15-20.

11. The method according to any one of items 8 to 10, wherein the pupa further comprises a nucleic acid sequence encoding a recombinant protein, preferably selected from the group consisting of subunit monomeric vaccine, subunit multimeric vaccine, virus like particle, therapeutic protein, antibody, enzyme, cytokine, blood clotting factor, anticoagulant, receptor, hormone, diagnostic protein reagents and the green fluorescent protein (GFP).

12. A method for producing a silk-free pupa belonging to the order Lepidoptera, preferably to the species *T. ni*, comprising the steps of:
   (a) Providing a pupa contained in a silk cocoon;
   (b) Treating the silk cocoon containing a pupa with a solution of a salt of hypochlorous acid, preferably sodium hypochlorite; and
   (c) Obtaining a silk-free and disinfected pupa.

13. A method for producing a recombinant baculovirus comprising the steps of:
   (a) Providing a pupa, preferably a silk-free pupa preferably belonging to the order Lepidoptera, preferably to the genera *Trichoplusia, Rachiplusia, Spodoptera, Heliothis, Manduca, Helicoverpa, Ascalapha* or *Samia*, even more preferably to the species *Trichoplusia ni, Manduca sexta, Spodoptera frugiperda, Spodoptera litoralis, Ascalapha odorata, Helicoverpa zea, Heliothis virescens, Rachiplusia nu* or *Samia cynthia*, or any other pupa susceptible to be infected by a recombinant baculovirus and/or a bacmid derived from AcMNPV;
   (b) Transfecting the pupa of step (a) with a bacmid suitable for producing a recombinant baculovirus derived from *Autographa californica* multicapsid nucleopolyhedrovirus (AcMNPV);
   (c) Incubating the inoculated pupa of step (b) for a period of time sufficient for the recombinant baculovirus is produced;
   (d) Obtaining the pupae comprising the recombinant baculovirus;
   (e) Optionally, harvesting the recombinant baculovirus; and
   (f) Optionally, purifying the recombinant baculovirus.

14. The method according to item 13, wherein the bacmid suitable for producing a recombinant baculovirus derived from *Autographa californica* multicapsid nucleopolyhedrovirus (AcMNPV) comprises or alternatively, consists of, a nucleic acid sequence that allows for the expression above endogenous levels of the proteins IE-1, IE-0 and/or fragments thereof functioning as transcriptional regulators above endogenous levels obtained during baculovirus infection and a recombinant homologous region (hr) operably linked to any promoter that is suitable for driving the expression of a recombinant protein, wherein preferably the nucleic acid sequence that allows for the expression above endogenous levels of the proteins IE-1, IE-0 and/or fragments thereof functioning as transcriptional regulators above endogenous levels obtained during baculovirus infection and the recombinant homologous region (hr) operably linked to any promoter that is suitable for driving the expression of a recombinant protein are as defined in claim 4.

15. The method according to item 14, wherein the nucleic acid sequence that comprises combinations of recombinant promoters, sequences encoding transcriptional regulators and enhancer regions are selected from the group comprising SEQ ID NO: 15-20.

16. A device comprising a precision pump, a mobile mechanic arm and a (removable) needle suitable for injecting a fluid into a pupa belonging to the order Lepidoptera, preferably to the genera *Trichoplusia, Rachiplusia, Spodoptera, Heliothis, Manduca, Helicoverpa, Ascalapha* or *Samia*, even more preferably to the species *Trichoplusia ni, Manduca sexta, Spodoptera frugiperda, Spodoptera litoralis, Ascalapha odorata, Helicoverpa zea, Heliothis virescens, Rachiplusia nu* or *Samia cynthia*, or any other pupa susceptible to be infected by a recombinant baculovirus and/or a bacmid derived from AcMNPV, wherein preferably the pupa is provided in a matrix or array.

17. The device according to item 16, wherein the device further comprises a computer program for defining the position of the needle and/or for calculating the distance from the needle to the pupa and/or the distance of penetration of the needle into the pupa and/or the volume of liquid (preferably comprising a recombinant baculovirus or bacmid) to be inoculated into the pupa, and wherein the device preferably further comprises a computer program for, e.g., determining the coordinates of the inoculation needle and/or calculating the inoculation volume and/or time and/or the time between inoculation of the pupae.

The invention claimed is:

1. A silk-free pupa comprising a recombinant baculovirus and/or a bacmid derived from *Autographa californica* multicapsid nucleopolyhedrovirus (AcMNPV), wherein the silk-free pupa belongs to genus *Trichoplusia*, and wherein the recombinant baculovirus and/or bacmid was injected into the silk-free pupa.

2. The silk-free pupa of claim 1, wherein the recombinant baculovirus and/or bacmid comprises a nucleic acid sequence encoding a recombinant protein.

3. The silk-free pupa of claim 1, wherein the baculovirus and/or bacmid comprises:
   (i) a nucleic acid sequence that allows for expression, above an endogenous level, of IE-1, IE-0, and/or fragments thereof, wherein expressed IE-1, IE-0, and/or fragments thereof are each capable of functioning as a transcriptional regulator above an endogenous level obtained during a baculovirus infection; and
   (ii) a recombinant homologous region (hr) operably linked to any promoter that is suitable for driving expression of a recombinant protein, wherein the nucleic acid sequence of (i) comprises
   (a) a nucleic acid comprising the nucleotide sequence set forth in any one of SEQ ID NOs: 1-5,
   (b) a nucleic acid sequence having a sequence identity of at least 70% with the nucleotide sequence set forth in any one of SEQ ID NOs: 1-5 and encoding a protein that is able to function as a transcriptional regulator in a recombinant baculovirus,
   (c) a nucleic acid sequence encoding an amino acid sequence comprising the amino acid sequence set forth in any one of SEQ ID NOs: 6-9, or
   (d) a nucleic acid sequence encoding an amino acid sequence that (1) has a sequence identity of at least 70% with the amino acid sequence set forth in any one of SEQ ID NOs: 6-9 and (2) is able to function as a transcriptional regulator in a recombinant baculovirus.

4. A silk-free pupa comprising
a recombinant baculovirus and/or a bacmid derived from *Autographa californica* multicapsid nucleopolyhedrovirus (AcMNPV), wherein the recombinant baculovirus and/or bacmid was injected into the silk-free pupa, and wherein the recombinant baculovirus and/or a bacmid comprises:
(i) a nucleic acid sequence that allows for expression, above an endogenous level, of IE-1, IE-0, and/or fragments thereof, wherein expressed IE-1, IE-0, and/or fragments thereof are each capable of functioning as a transcriptional regulator above an endogenous level obtained during a baculovirus infection; and
(ii) a recombinant homologous region (hr) operably linked to any promoter that is suitable for driving expression of a recombinant protein,
wherein the silk-free pupa belongs to genus *Trichoplusia*, and wherein the nucleic acid sequence of (i) comprises
   (a) a nucleic acid comprising the nucleotide sequence set forth in any one of SEQ ID NOs: 1-5,
   (b) a nucleic acid sequence having a sequence identity of at least 80% with the nucleotide sequence set forth in any one of SEQ ID NOs: 1-5 and encoding a protein that is able to function as a transcriptional regulator in a recombinant baculovirus,
   (c) a nucleic acid sequence encoding an amino acid comprising the amino acid sequence set forth in any one of SEQ ID NOs: 6-9, or
   (d) a nucleic acid sequence encoding an amino acid sequence that (1) has a sequence identity of at least 70% with the amino acid sequence set forth in any one of SEQ ID NOs: 6-9 and (2) is able to function as a transcriptional regulator in a recombinant baculovirus.

5. The silk-free pupa of claim 3, further comprising a promoter that drives expression of the recombinant protein, wherein the promoter is selected from the group consisting of:
   (a) a nucleic acid comprising the nucleotide sequence set forth in any of SEQ ID NOs: 10-14; and
   (b) a nucleic acid sequence able to function as a promoter in a recombinant baculovirus and having a sequence identity of at least 70% with the nucleotide sequence set forth in any of SEQ ID NOs: 10-14; and/or
wherein the recombinant homologous region (hr) comprises or consists of the sequence set forth in SEQ ID NO: 21 (hr1).

6. The silk-free pupa of claim 2, wherein the recombinant baculovirus further comprises the nucleic acid sequence set forth in any one of SEQ ID NOs: 15-20.

7. The silk-free pupa of claim 3, wherein the pupa further comprises a nucleic acid sequence encoding a recombinant protein.

8. A method for producing at least one recombinant protein, comprising:
   (a) providing a silk-free pupa of genus *Trichoplusia*;
   (b) injecting the silk-free pupa of (a) with
   a recombinant baculovirus derived from *Autographa californica* multicapsid nucleopolyhedrovirus (AcMNPV) to obtain an inoculated silk-free pupa, wherein the recombinant baculovirus comprises a nucleic acid sequence encoding at least one recombinant protein; and
   (c) incubating the inoculated silk-free pupa of (b) for a period of time sufficient for the at least one recombinant protein to be expressed,
   thereby obtaining the silk-free pupa comprising the at least one recombinant protein.

9. The method of claim 8, wherein the recombinant baculovirus comprises:

(i) a nucleic acid sequence that allows for expression, above an endogenous level, of IE-1, IE-0, and/or fragments thereof, wherein expressed IE-1, IE-0, and/or fragments thereof are each capable of functioning as a transcriptional regulator above an endogenous level obtained during a baculovirus infection; and (ii) a recombinant homologous region (hr) operably linked to any promoter that is suitable for driving expression of a recombinant protein, wherein the nucleic acid sequence of (i) comprises (a) a nucleic acid comprising the nucleotide sequence set forth in any one of SEQ ID NOs: 1-5, (b) a nucleic acid sequence having a sequence identity of at least 70% with the nucleotide sequence set forth in any one of SEQ ID NOs: 1-5 and encoding a protein that is able to function as a transcriptional regulator in a recombinant baculovirus, (c) a nucleic acid sequence encoding an amino acid comprising the amino acid sequence set forth in any one of SEQ ID NOs: 6-9, or (d) a nucleic acid sequence encoding an amino acid sequence that (1) has a sequence identity of at least 70% with the amino acid sequence set forth in any one of SEQ ID NOs: 6-9, and (2) is able to function as a transcriptional regulator in a recombinant baculovirus.

10. The method of claim 9, wherein the recombinant baculovirus comprises the nucleic acid sequence set forth in any one of SEQ ID NOs: 15-20.

11. The method of claim 8, wherein the silk-free pupa is externally disinfected, and wherein providing the silk-free pupa in (a) comprises (i) providing the pupa contained in a silk cocoon; and (ii) treating the silk cocoon containing the pupa with a solution of a salt of hypochlorous acid; thereby obtaining the silk-free and externally disinfected pupa.

12. A method for producing a silk-free pupa comprising a recombinant baculovirus, comprising:

(a) providing a silk-free pupa belonging to genus *Trichoplusia;*

(b) injecting the silk-free pupa of (a) with a bacmid suitable for producing a recombinant baculovirus derived from *Autographa californica* multicapsid nucleopolyhedrovirus (AcMNPV) to obtain an inoculated silk-free pupa; and (c) incubating the inoculated silk-free pupa of (b) for a period of time sufficient to produce the recombinant baculovirus, thereby obtaining the silk-free pupa comprising the recombinant baculovirus.

13. The method of claim 12, wherein the bacmid suitable for producing a recombinant baculovirus derived from *Autographa californica* multicapsid nucleopolyhedrovirus (AcMNPV) comprises:

(i) a nucleic acid sequence that allows for expression, above an endogenous level, of IE-1, IE-0, and/or fragments thereof, wherein expressed IE-1, IE-0, and/or fragments thereof are each capable of functioning as a transcriptional regulator above an endogenous level obtained during baculovirus infection; and (ii) a recombinant homologous region (hr) operably linked to any promoter that is suitable for driving expression of a recombinant protein, wherein the nucleic acid sequence of (i) comprises (a) a nucleic acid comprising the nucleotide sequence set forth in any one of SEQ ID NOs: 1-5, (b) a nucleic acid sequence having a sequence identity of at least 70% with the nucleotide sequence set forth in any one of SEQ ID NOs: 1-5 and encoding a protein that is able to function as a transcriptional regulator in a recombinant baculovirus, (c) a nucleic acid sequence encoding an amino acid comprising the amino acid sequence set forth in any one of SEQ ID NOs: 6-9, or (d) a nucleic acid sequence encoding an amino acid sequence that (1) has a sequence identity of at least 70% with the amino acid sequence set forth in any one of SEQ ID NOs: 6-9 and (2) is able to function as a transcriptional regulator in a recombinant baculovirus.

14. The method of claim 13, wherein the recombinant baculovirus comprises the nucleic acid sequence set forth in any one of SEQ ID NOs: 15-20.

15. The method of claim 8, wherein injecting the silk-free pupa in (b) comprises injecting a fluid comprising the recombinant baculovirus into the silk-free pupa using a device comprising a precision pump, a mobile mechanic arm and a needle suitable for injecting the fluid into the silk-free pupa.

16. The method according to claim 15, wherein the device further comprises a computer program for defining a position of the needle and/or for calculating a distance from the needle to the silk-free pupa and/or a distance of penetration of the needle into the silk-free pupa and/or a volume of liquid to be inoculated into the silk-free pupa.

17. The silk-free pupa of claim 2, wherein the recombinant baculovirus and/or bacmid comprises: (i) a nucleic acid sequence encoding a baculovirus transcriptional regulator; and (ii) an enhancer homologous region (hr) operably linked to a promoter suitable for driving the expression of the recombinant protein.

18. The method of claim 12, wherein the injecting in (b) comprises injecting the silk-free pupa of (a) with a bacmid comprising (i) a nucleic acid sequence encoding a baculovirus transcriptional regulator; (ii) a recombinant homologous region (hr) operably linked to a promoter; and (iii) a nucleic acid sequence encoding a protein.

19. The silk-free pupa of claim 1, wherein the silk-free pupa has been externally disinfected.

* * * * *

SEQUENCE LISTING

<160> NUMBER OF SEQ ID NOS: 38

<210> SEQ ID NO 1
<211> LENGTH: 1911
<212> TYPE: DNA
<213> ORGANISM: Autographa californica nucleopolyhedrovirus

<400> SEQUENCE: 1

```
atgatccgta catccagcca cgtcctgaac gtccaagaaa acatcatgac ttccaactgt      60
gcttccagcc cctactcctg tgaggccact tcagcctgcg ctgaggccca gcaactgcag     120
gtggacacag gtggcgataa gatcgtgaac aaccaggtca ccatgactca aatcaacttc     180
aacgcttcct acacctctgc cagcactccc tctcgtgcta gcttcgacaa ctcatactcg     240
gagttctgcg acaagcaacc taacgattac ttgtcttact acaaccaccc aaccccggac     300
ggagctgata ctgtcatctc cgactctgaa accgctgccg ctagcaactt cctcgcctca     360
gttaactcgc tcactgacaa cgatttggtg gagtgtctgc tcaagaccac tgacaacctg     420
gaggaagctg tgtcctctgc ctactacagc gagtcactcg aacagccagt ggtcgaacaa     480
ccctctccta gctcagctta ccacgccgag tccttcgaac actctgctgg tgtcaaccag     540
ccgtcggcca caggcaccaa gaggaagttg gacgagtacc tggataactc ccagggagtt     600
gtgggtcaat tcaacaagat caagttgaga cctaagtaca agaagagcac catccagtca     660
tgcgctacac tggaacaaac catcaaccac aacactaaca tctgtacagt ggcttccacc     720
caggagatca ctcactactt cacaaacgac ttcgccccct acctgatgag gttcgacgat     780
aacgactaca actcgaacag attctccgat cacatgtctg aaaccggtta ctacatgttc     840
gtcgttaaga gtccgaggt gaagcctttc gaaatcatct tcgccaagta cgtctctaac      900
gtggtctacg agtacacaaa caactactac atggttgaca accgtgtgtt cgttgtgacc     960
ttcgataaga tccgcttcat gatcagctac aacctggtta aggagactgg catcgaaatc    1020
ccacactcac aggacgtctg caacgatgag accgccgctc aaaactgcaa gaagtgtcac    1080
ttcgtggacg tccaccacac attcaaggcc gctctgacct cctacttcaa cctcgatatg    1140
tactacgctc agacaacctt cgtgaccttg ctgcaatcac tcggcgagcg taagtgtgga    1200
ttcctcttgt cgaagttgta cgagatgtac caggacaaga acctcttcac tttgcccatc    1260
atgctgagcc gcaaggaatc aaacgagatc gaaaccgcct ctaacaactt cttcgtctcg    1320
ccatacgttt cccagatcct caagtactcg gagtccgtcc aattcccgga caaccctccc    1380
aacaagtacg tcgttgataa cctgaacctc atcgtgaaca agaagagcac tctgacatac    1440
aagtactcgt ccgtcgctaa cctgctcttc aacaactaca gtaccacga caacatcgct     1500
tctaacaaca acgccgagaa cctcaagaag gtcaagaagg aagacggaag catgcacatc    1560
gttgagcagt acttgactca aaacgtcgat aacgttaagg gtcacaactt catcgtgttg    1620
tccttcaaga acgaggaaag gctgaccatc gctaagaaga caaggagtt ctactggatc     1680
tctggcgaaa tcaaggacgt tgatgtgagc caggtcatcc aaaagtacaa cagattcaag    1740
cacccacatgt tcgtgatcgg caaggtcaac cgtcgcgagt caactacact gcacaacaac    1800
ttgctgaagc tcttggcctt gatcctgcag ggactggtgc cactctccga cgccatcaca    1860
ttcgccgagc aaaagctcaa ctgcaagtac aagaagttcg agttcaacta a             1911
```

<210> SEQ ID NO 2
<211> LENGTH: 1749
<212> TYPE: DNA
<213> ORGANISM: Autographa californica nucleopolyhedrovirus

<400> SEQUENCE: 2

```
atgactcaaa tcaacttcaa cgcttcctac acctctgcca gcactccctc tcgtgctagc    60
ttcgacaact catactcgga gttctgcgac aagcaaccta acgattactt gtcttactac   120
aaccacccaa ccccggacgg agctgatact gtcatctccg actctgaaac cgctgccgct   180
agcaacttcc tcgcctcagt taactcgctc actgacaacg atttggtgga gtgtctgctc   240
aagaccactg acaacctgga ggaagctgtg tcctctgcct actacagcga gtcactcgaa   300
cagccagtgg tcgaacaacc ctctcctagc tcagcttacc acgccgagtc cttcgaacac   360
tctgctggtg tcaaccagcc gtcggccaca ggcaccaaga ggaagttgga cgagtacctg   420
gataactccc agggagttgt gggtcaattc aacaagatca agttgagacc taagtacaag   480
aagagcacca tccagtcatg cgctacactg aacaaaccat caaccacaa cactaacatc    540
tgtacagtgg cttccaccca ggagatcact cactacttca aaacgactt cgccccctac   600
ctgatgaggt tcgacgataa cgactacaac tcgaacagat tctccgatca catgtctgaa   660
accggttact acatgttcgt cgttaagaag tccgaggtga agcctttcga atcatcttc    720
gccaagtacg tctctaacgt ggtctacgag tacacaaaca actactacat ggttgacaac   780
cgtgtgttcg ttgtgaccct cgataagatc cgcttcatga tcagctacaa cctggttaag   840
gagactggca tcgaaatccc acactcacag gacgtctgca cgatgagac cgccgctcaa   900
aactgcaaga agtgtcactt cgtggacgtc caccacacat tcaaggccgc tctgacctcc   960
tacttcaacc tcgatatgta ctacgctcag acaaccttcg tgaccttgct gcaatcactc  1020
ggcgagcgta agtgtggatt cctcttgtcg aagttgtacg agatgtacca ggacaagaac  1080
ctcttcactt tgcccatcat gctgagccgc aaggaatcaa acgagatcga accgcctct   1140
aacaacttct tcgtctcgcc atacgtttcc cagatcctca gtactcgga gtccgtccaa   1200
ttcccggaca ccctcccaa caagtacgtc gttgataacc tgaacctcat cgtgaacaag   1260
aagagcactc tgacatacaa gtactcgtcc gtcgctaacc tgctcttcaa caactacaag   1320
taccacgaca catcgcttc taacaacaac gccgagaacc tcaagaaggt caagaaggaa   1380
gacggaagca tgcacatcgt tgagcagtac ttgactcaaa acgtcgataa cgttaagggt   1440
cacaacttca tcgtgttgtc cttcaagaac gaggaaaggc tgaccatcgc taagaagaac   1500
aaggagttct actggatctc tggcgaaatc aaggacgttg atgtgagcca ggtcatccaa   1560
aagtacaaca gattcaagca ccacatgttc gtgatcggca aggtcaaccg tcgcgagtca   1620
actacactgc acaacaactt gctgaagctc ttggccttga tcctgcaggg actggtgcca   1680
ctctccgacg ccatcacatt cgccgagcaa aagctcaact gcaagtacaa gaagttcgag   1740
ttcaactaa                                                          1749
```

<210> SEQ ID NO 3
<211> LENGTH: 1911
<212> TYPE: DNA
<213> ORGANISM: Autographa californica nucleopolyhedrovirus

<400> SEQUENCE: 3

```
atgatccgta catccagcca cgtcctgaac gtccaagaaa acatcatgac ttccaactgt    60
gcttccagcc cctactcctg tgaggccact tcagcctgcg ctgaggccca gcaactgcag   120
gtggacacag gtggcgataa gatcgtgaac aaccaggtca ccatgactca aatcaacttc   180
aacgcttcct acacctctgc cagcactccc tctcgtgcta gcttcgacaa ctcatactcg   240
```

-continued

| | |
|---|---:|
| gagttctgcg acaagcaacc taacgattac ttgtcttact acaaccaccc aaccccggac | 300 |
| ggagctgata ctgtcatctc cgactctgaa accgctgccg ctagcaactt cctcgcctca | 360 |
| gttaactcgc tcactgacaa cgatttggtg gagtgtctgc tcaagaccac tgacaacctg | 420 |
| gaggaagctg tgtcctctgc ctactacagc gagtcactcg aacagccagt ggtcgaacaa | 480 |
| ccctctccta gctcagctta ccacgccgag tccttcgaac actctgctgg tgtcaaccag | 540 |
| ccgtcggcca caggcaccaa gaggaagttg gacgagtacc tggataactc cagggagtt | 600 |
| gtgggtcaat tcaacaagat caagttgaga cctaagtaca agaagagcac catccagtca | 660 |
| tgcgctacac tggaacaaac catcaaccac aacactaaca tctgtacagt ggcttccacc | 720 |
| caggagatca ctcactactt cacaaacgac ttcgccccct acctgatgag gttcgacgat | 780 |
| aacgactaca actcgaacag attctccgat cacatgtctg aaaccggtta ctacatgttc | 840 |
| gtcgttaaga gtccgaggt gaagcctttc gaaatcatct tcgccaagta cgtctctaac | 900 |
| gtggtctacg agtacacaaa caactactac atggttgaca accgtgtgtt cgttgtgacc | 960 |
| ttcgataaga tccgcttcat gatcagctac aacctggtta aggagactgg catcgaaatc | 1020 |
| ccacactcac aggacgtctg caacgatgag accgccgctc aaaactgcaa gaagtgtcac | 1080 |
| ttcgtggacg tccaccacac attcaaggcc gctctgacct cctacttcaa cctcgatatg | 1140 |
| tactacgctc agacaacctt cgtgaccttg ctgcaatcac tcggcgagcg taagtgtgga | 1200 |
| ttcctcttgt cgaagttgta cgagatgtac caggacaaga acctcttcac tttgcccatc | 1260 |
| atgctgagcc gcaaggaatc aaacgagatc gaaaccgcct ctaacaactt cttcgtctcg | 1320 |
| ccatacgttt cccagatcct caagtactcg gagtccgtcc aattcccgga caaccctccc | 1380 |
| aacaagtacg tcgttgataa cctgaacctc atcgtgaaca agaagagcac tctgacatac | 1440 |
| aagtactcgt ccgtcgctaa cctgctcttc aacaactaca agtaccacga caacatcgct | 1500 |
| tctaacaaca cgccgagaa cctcaagaag gtcaagaagg aagacggaag catgcacatc | 1560 |
| gttgagcagt acttgactca aaacgtcgat aacgttaagg gtcacaactt catcgtgttg | 1620 |
| tccttcaaga cgaggaaag gctgaccatc gctaagaaga caaggagtt ctactggatc | 1680 |
| tctggcgaaa tcaaggacgt tgatgtgagc caggtcatcc aaaagtacaa cagattcaag | 1740 |
| caccacatgt tcgtgatcgg caaggtcaac cgtcgcgagt caactacact gcacaacaac | 1800 |
| ttgctgaagc tcttggcctt gatcctgcag ggactggtgc cactctccga cgccatcaca | 1860 |
| ttcgccgagc aaaagctcaa ctgcaagtac aagaagttcg agttcaacta a | 1911 |

<210> SEQ ID NO 4
<211> LENGTH: 666
<212> TYPE: DNA
<213> ORGANISM: Autographa californica nucleopolyhedrovirus

<400> SEQUENCE: 4

| | |
|---|---:|
| atgactcaaa tcaacttcaa cgcttcctac acctctgcca gcactccctc tcgtgctagc | 60 |
| ttcgacaact catactcgga gttctgcgac aagcaaccta cgattactt gtcttactac | 120 |
| aaccacccaa ccccggacgg agctgatact gtcatctccg actctgaaac cgctgccgct | 180 |
| agcaacttcc tcgcctcagt taactcgctc actgacaacg atttggtgga gtgtctgctc | 240 |
| aagaccactg acaacctgga ggaagctgtg tcctctgcct actacagcga gtcactcgaa | 300 |
| cagccagtgg tcgaacaacc ctctcctagc tcagcttacc acgccgagtc cttcgaacac | 360 |
| tctgctggtg tcaaccagcc gtcggccaca ggcaccaaga ggaagttgga cgagtacctg | 420 |
| gataactccc agggagttgt gggtcaattc aacaagatca agttgagacc taagtacaag | 480 |

```
aagagcacca tccagtcatg cgctacactg gaacaaacca tcaaccacaa cactaacatc      540
tgtacagtgg cttccaccca ggagatcact cactacttca caaacgactt cgcccctac      600 ctgatgaggt tcgacgataa cgactacaac tcgaacagat tctccgatca catgtctgaa      660
accggt                                                                666

<210> SEQ ID NO 5
<211> LENGTH: 828
<212> TYPE: DNA
<213> ORGANISM: Autographa californica nucleopolyhedrovirus

<400> SEQUENCE: 5
atgatccgta catccagcca cgtcctgaac gtccaagaaa acatcatgac ttccaactgt       60
gcttccagcc cctactcctg tgaggccact tcagcctgcg ctgaggccca gcaactgcag      120
gtggacacag gtggcgataa gatcgtgaac aaccaggtca ccatgactca aatcaacttc      180
aacgcttcct acacctctgc cagcactccc tctcgtgcta gcttcgacaa ctcatactcg      240
gagttctgcg acaagcaacc taacgattac ttgtcttact acaaccaccc aaccccggac      300
ggagctgata ctgtcatctc cgactctgaa accgctgccg ctagcaactt cctcgcctca      360
gttaactcgc tcactgacaa cgatttggtg gagtgtctgc tcaagaccac tgacaacctg      420
gaggaagctg tgtcctctgc ctactacagc gagtcactcg aacagccagt ggtcgaacaa      480
ccctctccta gctcagctta ccacgccgag tccttcgaac actctgctgg tgtcaaccag      540
ccgtcggcca caggcaccaa gaggaagttg acgagtacc tggataactc ccagggagtt      600
gtgggtcaat tcaacaagat caagttgaga cctaagtaca agaagagcac catccagtca      660
tgcgctacac tggaacaaac catcaaccac aacactaaca tctgtacagt ggcttccacc      720
caggagatca ctcactactt cacaaacgac ttcgccccct acctgatgag gttcgacgat      780
aacgactaca actcgaacag attctccgat cacatgtctg aaaccggt                  828

<210> SEQ ID NO 6
<211> LENGTH: 582
<212> TYPE: PRT
<213> ORGANISM: Autographa californica nucleopolyhedrovirus

<400> SEQUENCE: 6

Met Thr Gln Ile Asn Phe Asn Ala Ser Tyr Thr Ser Ala Ser Thr Pro
  1               5                  10                  15

Ser Arg Ala Ser Phe Asp Asn Ser Tyr Ser Glu Phe Cys Asp Lys Gln
             20                  25                  30

Pro Asn Asp Tyr Leu Ser Tyr Tyr Asn His Pro Thr Pro Asp Gly Ala
         35                  40                  45

Asp Thr Val Ile Ser Asp Ser Glu Thr Ala Ala Ser Asn Phe Leu
     50                  55                  60

Ala Ser Val Asn Ser Leu Thr Asp Asn Asp Leu Val Glu Cys Leu Leu
 65                  70                  75                  80

Lys Thr Thr Asp Asn Leu Glu Glu Ala Val Ser Ser Ala Tyr Tyr Ser
                 85                  90                  95

Glu Ser Leu Glu Gln Pro Val Val Glu Gln Pro Ser Pro Ser Ser Ala
            100                 105                 110

Tyr His Ala Glu Ser Phe Glu His Ser Ala Gly Val Asn Gln Pro Ser
        115                 120                 125

Ala Thr Gly Thr Lys Arg Lys Leu Asp Glu Tyr Leu Asp Asn Ser Gln
    130                 135                 140
```

```
Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
                165                 170                 175

Asn Thr Asn Ile Cys Thr Val Ala Ser Thr Gln Glu Ile Thr His Tyr
            180                 185                 190

Phe Thr Asn Asp Phe Ala Pro Tyr Leu Met Arg Phe Asp Asp Asn Asp
        195                 200                 205

Tyr Asn Ser Asn Arg Phe Ser Asp His Met Ser Glu Thr Gly Tyr Tyr
    210                 215                 220

Met Phe Val Val Lys Lys Ser Glu Val Lys Pro Phe Glu Ile Ile Phe
225                 230                 235                 240

Ala Lys Tyr Val Ser Asn Val Val Tyr Glu Tyr Thr Asn Asn Tyr Tyr
                245                 250                 255

Met Val Asp Asn Arg Val Phe Val Val Thr Phe Asp Lys Ile Arg Phe
                260                 265                 270

Met Ile Ser Tyr Asn Leu Val Lys Glu Thr Gly Ile Glu Ile Pro His
            275                 280                 285

Ser Gln Asp Val Cys Asn Asp Glu Thr Ala Ala Gln Asn Cys Lys Lys
        290                 295                 300

Cys His Phe Val Asp Val His His Thr Phe Lys Ala Ala Leu Thr Ser
305                 310                 315                 320

Tyr Phe Asn Leu Asp Met Tyr Ala Gln Thr Thr Phe Val Thr Leu
                325                 330                 335

Leu Gln Ser Leu Gly Glu Arg Lys Cys Gly Phe Leu Leu Ser Lys Leu
            340                 345                 350

Tyr Glu Met Tyr Gln Asp Lys Asn Leu Phe Thr Leu Pro Ile Met Leu
        355                 360                 365

Ser Arg Lys Glu Ser Asn Glu Ile Glu Thr Ala Ser Asn Asn Phe Phe
    370                 375                 380

Val Ser Pro Tyr Val Ser Gln Ile Leu Lys Tyr Ser Glu Ser Val Gln
385                 390                 395                 400

Phe Pro Asp Asn Pro Asn Lys Tyr Val Asp Asn Leu Asn Leu
                405                 410                 415

Ile Val Asn Lys Lys Ser Thr Leu Thr Tyr Lys Tyr Ser Ser Val Ala
                420                 425                 430

Asn Leu Leu Phe Asn Asn Tyr Lys Tyr His Asp Asn Ile Ala Ser Asn
            435                 440                 445

Asn Asn Ala Glu Asn Leu Lys Lys Val Lys Lys Glu Asp Gly Ser Met
        450                 455                 460

His Ile Val Glu Gln Tyr Leu Thr Gln Asn Val Asp Asn Val Lys Gly
465                 470                 475                 480

His Asn Phe Ile Val Leu Ser Phe Lys Asn Glu Glu Arg Leu Thr Ile
                485                 490                 495

Ala Lys Lys Asn Lys Glu Phe Tyr Trp Ile Ser Gly Glu Ile Lys Asp
                500                 505                 510

Val Asp Val Ser Gln Val Ile Gln Lys Tyr Asn Arg Phe Lys His His
            515                 520                 525

Met Phe Val Ile Gly Lys Val Asn Arg Arg Glu Ser Thr Thr Leu His
        530                 535                 540

Asn Asn Leu Leu Lys Leu Leu Ala Leu Ile Leu Gln Gly Leu Val Pro
545                 550                 555                 560
```

Leu Ser Asp Ala Ile Thr Phe Ala Glu Gln Lys Leu Asn Cys Lys Tyr
                565                 570                 575

Lys Lys Phe Glu Phe Asn
            580

<210> SEQ ID NO 7
<211> LENGTH: 636
<212> TYPE: PRT
<213> ORGANISM: Autographa californica nucleopolyhedrovirus

<400> SEQUENCE: 7

Met Ile Arg Thr Ser Ser His Val Leu Asn Val Gln Glu Asn Ile Met
1               5                   10                  15

Thr Ser Asn Cys Ala Ser Ser Pro Tyr Ser Cys Glu Ala Thr Ser Ala
            20                  25                  30

Cys Ala Glu Ala Gln Gln Leu Gln Val Asp Thr Gly Gly Asp Lys Ile
        35                  40                  45

Val Asn Asn Gln Val Thr Met Thr Gln Ile Asn Phe Asn Ala Ser Tyr
    50                  55                  60

Thr Ser Ala Ser Thr Pro Ser Arg Ala Ser Phe Asp Asn Ser Tyr Ser
65                  70                  75                  80

Glu Phe Cys Asp Lys Gln Pro Asn Asp Tyr Leu Ser Tyr Tyr Asn His
                85                  90                  95

Pro Thr Pro Asp Gly Ala Asp Thr Val Ile Ser Asp Ser Glu Thr Ala
            100                 105                 110

Ala Ala Ser Asn Phe Leu Ala Ser Val Asn Ser Leu Thr Asp Asn Asp
        115                 120                 125

Leu Val Glu Cys Leu Leu Lys Thr Thr Asp Asn Leu Glu Glu Ala Val
    130                 135                 140

Ser Ser Ala Tyr Tyr Ser Glu Ser Leu Glu Gln Pro Val Val Glu Gln
145                 150                 155                 160

Pro Ser Pro Ser Ser Ala Tyr His Ala Glu Ser Phe Glu His Ser Ala
                165                 170                 175

Gly Val Asn Gln Pro Ser Ala Thr Gly Thr Lys Arg Lys Leu Asp Glu
            180                 185                 190

Tyr Leu Asp Asn Ser Gln Gly Val Val Gly Gln Phe Asn Lys Ile Lys
        195                 200                 205

Leu Arg Pro Lys Tyr Lys Lys Ser Thr Ile Gln Ser Cys Ala Thr Leu
    210                 215                 220

Glu Gln Thr Ile Asn His Asn Thr Asn Ile Cys Thr Val Ala Ser Thr
225                 230                 235                 240

Gln Glu Ile Thr His Tyr Phe Thr Asn Asp Phe Ala Pro Tyr Leu Met
                245                 250                 255

Arg Phe Asp Asp Asn Asp Tyr Asn Asn Arg Phe Ser Asp His Met
            260                 265                 270

Ser Glu Thr Gly Tyr Tyr Met Phe Val Val Lys Lys Ser Glu Val Lys
        275                 280                 285

Pro Phe Glu Ile Ile Phe Ala Lys Tyr Val Ser Asn Val Val Tyr Glu
    290                 295                 300

Tyr Thr Asn Asn Tyr Tyr Met Val Asp Asn Arg Val Phe Val Val Thr
305                 310                 315                 320

Phe Asp Lys Ile Arg Phe Met Ile Ser Tyr Asn Leu Val Lys Glu Thr
                325                 330                 335

Gly Ile Glu Ile Pro His Ser Gln Asp Val Cys Asn Asp Glu Thr Ala
            340                 345                 350

-continued

```
Ala Gln Asn Cys Lys Lys Cys His Phe Val Asp Val His His Thr Phe
            355                 360                 365

Lys Ala Ala Leu Thr Ser Tyr Phe Asn Leu Asp Met Tyr Tyr Ala Gln
    370                 375                 380

Thr Thr Phe Val Thr Leu Leu Gln Ser Leu Gly Glu Arg Lys Cys Gly
385                 390                 395                 400

Phe Leu Leu Ser Lys Leu Tyr Glu Met Tyr Gln Asp Lys Asn Leu Phe
                405                 410                 415

Thr Leu Pro Ile Met Leu Ser Arg Lys Glu Ser Asn Glu Ile Glu Thr
            420                 425                 430

Ala Ser Asn Asn Phe Phe Val Ser Pro Tyr Val Ser Gln Ile Leu Lys
        435                 440                 445

Tyr Ser Glu Ser Val Gln Phe Pro Asp Asn Pro Pro Asn Lys Tyr Val
    450                 455                 460

Val Asp Asn Leu Asn Leu Ile Val Asn Lys Lys Ser Thr Leu Thr Tyr
465                 470                 475                 480

Lys Tyr Ser Ser Val Ala Asn Leu Leu Phe Asn Asn Tyr Lys Tyr His
                485                 490                 495

Asp Asn Ile Ala Ser Asn Asn Ala Glu Asn Leu Lys Lys Val Lys
            500                 505                 510

Lys Glu Asp Gly Ser Met His Ile Val Glu Gln Tyr Leu Thr Gln Asn
        515                 520                 525

Val Asp Asn Val Lys Gly His Asn Phe Ile Val Leu Ser Phe Lys Asn
    530                 535                 540

Glu Glu Arg Leu Thr Ile Ala Lys Lys Asn Lys Glu Phe Tyr Trp Ile
545                 550                 555                 560

Ser Gly Glu Ile Lys Asp Val Asp Val Ser Gln Val Ile Gln Lys Tyr
                565                 570                 575

Asn Arg Phe Lys His His Met Phe Val Ile Gly Lys Val Asn Arg Arg
            580                 585                 590

Glu Ser Thr Thr Leu His Asn Asn Leu Leu Lys Leu Leu Ala Leu Ile
        595                 600                 605

Leu Gln Gly Leu Val Pro Leu Ser Asp Ala Ile Thr Phe Ala Glu Gln
    610                 615                 620

Lys Leu Asn Cys Lys Tyr Lys Lys Phe Glu Phe Asn
625                 630                 635

<210> SEQ ID NO 8
<211> LENGTH: 222
<212> TYPE: PRT
<213> ORGANISM: Autographa californica nucleopolyhedrovirus

<400> SEQUENCE: 8

Met Thr Gln Ile Asn Phe Asn Ala Ser Tyr Thr Ser Ala Ser Thr Pro
1               5                   10                  15

Ser Arg Ala Ser Phe Asp Asn Ser Tyr Ser Glu Phe Cys Asp Lys Gln
            20                  25                  30

Pro Asn Asp Tyr Leu Ser Tyr Tyr Asn His Pro Thr Pro Asp Gly Ala
        35                  40                  45

Asp Thr Val Ile Ser Asp Ser Glu Thr Ala Ala Ala Ser Asn Phe Leu
    50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
```

```
            85                  90                  95
Glu Ser Leu Glu Gln Pro Val Val Glu Gln Pro Ser Pro Ser Ser Ala
            100                 105                 110

Tyr His Ala Glu Ser Phe Glu His Ser Ala Gly Val Asn Gln Pro Ser
            115                 120                 125

Ala Thr Gly Thr Lys Arg Lys Leu Asp Glu Tyr Leu Asp Asn Ser Gln
130                 135                 140

Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
                165                 170                 175

Asn Thr Asn Ile Cys Thr Val Ala Ser Thr Gln Glu Ile Thr His Tyr
            180                 185                 190

Phe Thr Asn Asp Phe Ala Pro Tyr Leu Met Arg Phe Asp Asn Asp
            195                 200                 205

Tyr Asn Ser Asn Arg Phe Ser Asp His Met Ser Glu Thr Gly
210                 215                 220

<210> SEQ ID NO 9
<211> LENGTH: 276
<212> TYPE: PRT
<213> ORGANISM: Autographa californica nucleopolyhedrovirus

<400> SEQUENCE: 9

Met Ile Arg Thr Ser Ser His Val Leu Asn Val Gln Glu Asn Ile Met
1               5                   10                  15

Thr Ser Asn Cys Ala Ser Ser Pro Tyr Ser Cys Glu Ala Thr Ser Ala
            20                  25                  30

Cys Ala Glu Ala Gln Gln Leu Gln Val Asp Thr Gly Gly Asp Lys Ile
        35                  40                  45

Val Asn Asn Gln Val Thr Met Thr Gln Ile Asn Phe Asn Ala Ser Tyr
    50                  55                  60

Thr Ser Ala Ser Thr Pro Ser Arg Ala Ser Phe Asp Asn Ser Tyr Ser
65                  70                  75                  80

Glu Phe Cys Asp Lys Gln Pro Asn Asp Tyr Leu Ser Tyr Tyr Asn His
                85                  90                  95

Pro Thr Pro Asp Gly Ala Asp Thr Val Ile Ser Asp Ser Glu Thr Ala
            100                 105                 110

Ala Ala Ser Asn Phe Leu Ala Ser Val Asn Ser Leu Thr Asp Asn Asp
        115                 120                 125

Leu Val Glu Cys Leu Leu Lys Thr Thr Asp Asn Leu Glu Glu Ala Val
    130                 135                 140

Ser Ser Ala Tyr Tyr Ser Glu Ser Leu Glu Gln Pro Val Val Glu Gln
145                 150                 155                 160

Pro Ser Pro Ser Ser Ala Tyr His Ala Glu Ser Phe Glu His Ser Ala
                165                 170                 175

Gly Val Asn Gln Pro Ser Ala Thr Gly Thr Lys Arg Lys Leu Asp Glu
            180                 185                 190

Tyr Leu Asp Asn Ser Gln Gly Val Val Gly Gln Phe Asn Lys Ile Lys
        195                 200                 205

Leu Arg Pro Lys Tyr Lys Lys Ser Thr Ile Gln Ser Cys Ala Thr Leu
    210                 215                 220

Glu Gln Thr Ile Asn His Asn Thr Asn Ile Cys Thr Val Ala Ser Thr
225                 230                 235                 240
```

Gln Glu Ile Thr His Tyr Phe Thr Asn Asp Phe Ala Pro Tyr Leu Met
            245                 250                 255

Arg Phe Asp Asp Asn Asp Tyr Asn Ser Asn Arg Phe Ser Asp His Met
        260                 265                 270

Ser Glu Thr Gly
        275

<210> SEQ ID NO 10
<211> LENGTH: 128
<212> TYPE: DNA
<213> ORGANISM: Autographa californica nucleopolyhedrovirus

<400> SEQUENCE: 10
atcatggaga taattaaaat gataaccatc tcgcaaataa ataagtattt tactgttttc    60
gtaacagttt tgtaataaaa aaacctataa atattccgga ttattcatac cgtcccacca   120
tcgggcgc                                                           128

<210> SEQ ID NO 11
<211> LENGTH: 122
<212> TYPE: DNA
<213> ORGANISM: Autographa californica nucleopolyhedrovirus

<400> SEQUENCE: 11
atacggacct taattcaac ccaacacaat atattatagt taaataagaa ttattatcaa     60
atcatttgta tattaattaa aatactatac tgtaaattac attttattta caatcactcg   120
ac                                                                 122

<210> SEQ ID NO 12
<211> LENGTH: 571
<212> TYPE: DNA
<213> ORGANISM: Artificial Sequence
<220> FEATURE:
<223> OTHER INFORMATION: Recombinant chimeric promoter

<400> SEQUENCE: 12
aaaaacatcg attagggtga ctgaaggtta cattggggta ggttatggtt aatacgtaat    60
ggtttaacac caaaacgata tcatggattt tatataaggt gtaataatat ttttaatgag   120
tggacgcgtc gggtcaatgt cctgcctatt gacgtcataa catattaggt gattatatta   180
aaaatagttt aaactcaaat attacttgca agtttaagtt tcatcataat ctgatcataa   240
gtttcaccca acagaaacc aaaagcataa ctatcgaata tctttagctt cccatgaaga    300
aagattaccg taaccatcac taggatttta tacgattgta gaaaataaag tattctcagt   360
ctcttttcag agcgctataa aaaggggtgc attctcggta agagtacagt tgaactcaca   420
tcgagttaac tccacgctgc agtctcgaga tacggacctt aattcaacc caacacaata    480 tattatagtt aaataagaat tattatcaaa tcatttgtat attaattaaa atactatact   540
gtaaattaca ttttatttac aatcactcga c                                 571

<210> SEQ ID NO 13
<211> LENGTH: 465
<212> TYPE: DNA
<213> ORGANISM: Artificial Sequence
<220> FEATURE:
<223> OTHER INFORMATION: Recombinant chimeric promoter

<400> SEQUENCE: 13
ggtaccaaat tccgttttgc gacgatgcag agttttgaa caggctgctc aaacacatag     60

| | |
|---|---|
| atccgtaccc gctcagtcgg atgtattaca atgcagccaa taccatgttt tacacgacta | 120 |
| tggaaaacta tgccgtgtcc aattgcaagt tcaacattga ggattacaat aacatattta | 180 |
| aggtgatgga aaatattagg aaacacagca acaaaaattc aaacgaccaa gacgagttaa | 240 |
| acatatattt gggagttcag tcgtcgaatg caaagcgtaa aaaatattaa taaggtaaaa | 300 |
| attacagcta cataaattac acaatttaaa ctgcagtctg gagatacgga cctttaattc | 360 |
| aacccaacac aatatattat agttaaataa gaattattat caaatcattt gtatattaat | 420 |
| taaaatacta tactgtaaat tacattttat ttacaatcac tcgac | 465 |

<210> SEQ ID NO 14
<211> LENGTH: 436
<212> TYPE: DNA
<213> ORGANISM: Autographa californica nucleopolyhedrovirus

<400> SEQUENCE: 14

| | |
|---|---|
| aaaaacatcg attagggtga ctgaaggtta cattggggta ggttatggtt aatacgtaat | 60 |
| ggtttaacac caaaacgata tcatggattt tatataaggt gtaataatat ttttaatgag | 120 |
| tggacgcgtc gggtcaatgt cctgcctatt gacgtcataa catattaggt gattatatta | 180 |
| aaaatagttt aaactcaaat attacttgca agtttaagtt tcatcataat ctgatcataa | 240 |
| gtttcaccca aacagaaacc aaaagcataa ctatcgaata tctttagctt cccatgaaga | 300 |
| aagattaccg taaccatcac taggatttta tacgattgta gaaaataaag tattctcagt | 360 |
| ctcttttcag agcgctataa aaagggggtgc attctcggta agagtacagt tgaactcaca | 420 |
| tcgagttaac tccacg | 436 |

<210> SEQ ID NO 15
<211> LENGTH: 3163
<212> TYPE: DNA
<213> ORGANISM: Artificial Sequence
<220> FEATURE:
<223> OTHER INFORMATION: Recombinant expression cassette

<400> SEQUENCE: 15

| | |
|---|---|
| ttagttgaac tcgaacttct tgtacttgca gttgagcttt tgctcggcga atgtgatggc | 60 |
| gtcggagagt ggcaccagtc cctgcaggat caaggccaag agcttcagca agttgttgtg | 120 |
| cagtgtagtt gactcgcgac ggttgacctt gccgatcacg aacatgtggt gcttgaatct | 180 |
| gttgtacttt tggatgacct ggctcacatc aacgtccttg atttcgccag agatccagta | 240 |
| gaactccttg ttcttcttag cgatggtcag cctttcctcg ttcttgaagg acaacacgat | 300 |
| gaagttgtga cccttaacgt tatcgacgtt ttgagtcaag tactgctcaa cgatgtgcat | 360 |
| gcttccgtct tccttcttga ccttcttgag gttctcggcg ttgttgttag aagcgatgtt | 420 |
| gtcgtggtac ttgtagttgt tgaagagcag gttagcgacg gacgagtact tgtatgtcag | 480 |
| agtgctcttc ttgttcacga tgaggttcag gttatcaacg acgtacttgt tgggagggtt | 540 |
| gtccgggaat tggacggact ccgagtactt gaggatctgg gaaacgtatg gcgagacgaa | 600 |
| gaagttgtta gaggcggttt cgatctcgtt tgattccttg cggctcagca tgatgggcaa | 660 |
| agtgaagagg ttcttgtcct ggtacatctc gtacaacttc gacaaggaga atccacactt | 720 |
| acgctcgccg agtgattgca gcaaggtcac gaaggttgtc tgagcgtagt acatatcgag | 780 |
| gttgaagtag gaggtcagag cggccttgaa tgtgtggtgg acgtccacga agtgacactt | 840 |
| cttgcagttt tgagcggcgg tctcatcgtt gcagacgtcc tgtgagtgtg ggatttcgat | 900 |
| gccagtctcc ttaaccaggt tgtagctgat catgaagcgg atcttatcga aggtcacaac | 960 |

```
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg tagggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg taagctgag ctaggagagg ttgttcgac    1440 cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatt   1920
gggtcatcta gattcgaaag cggccgcgac tagtgagctc gtcgacgtag gccttttgaat  1980 tccgcgcgct tcggaccggg atccgcgccc gatggtggga cggtatgaat aatccggaat   2040
atttataggt ttttttatta caaaactgtt acgaaaacag taaaatactt atttatttgc   2100
gagatggtta tcattttaat tatctccatg atctattaat attccggagt atacatcgat   2160 gttgaccccca acaaaagatt tataattaat cataatcacg aacaacaaca agtcaatgaa   2220
acaaataaac aagttgtcga taaaacattc ataaatgaca cagcaacata caattcttgc   2280
ataataaaaa tttaaatgac atcatatttg agaataacaa atgacattat ccctcgattg   2340
tgttttacaa gtagaattct acccgtaaag cgagtttagt tttgaaaaac aaatgacatc   2400
atttgtataa tgacatcatc ccctgattgt gttttacaag tagaattcta tccgtaaagc   2460
gagttcagtt ttgaaaacaa atgagtcata cctaaacacg ttaataatct tctgatatca   2520
gcttatgact caagttatga gccgtgtgca aaacatgaga taagtttatg acatcatcca   2580
ctgatcgtgc gttacaagta gaattctact cgtaaagcca gttcggttat gagccgtgtg   2640
caaaacatga catcagctta tgactcatac ttgattgtgt tttacgcgta gaattctact   2700
cgtaaagcga gttcggttat gagccgtgtg caaaacatga catcagctta tgagtcataa   2760
ttaatcgtgc gttacaagta gaattctact cgtaaagcga gttgaaggat catatttagt   2820
tgcgtttatg agataagatt gaaagcacgt gtaaaatgtt tcccgcgcgt tggcacaact   2880
atttacaatg cggccaagtt ataaaagatt ctaatctgat atgttttaaa acacctttgc   2940
ggcccgagtt gtttgcgtac gtgactagcg aagaagatgt gtggaccgca gaacagatag   3000
taaaacaaaa ccctagtatt ggagcaataa tcgatgagct catacggacc tttaattcaa   3060
cccaacacaa tatattatag ttaaataaga attattatca aatcatttgt atattaatta   3120
aaatactata ctgtaaatta catttttattt acaatcactc gac                   3163
```

<210> SEQ ID NO 16
<211> LENGTH: 3656
<212> TYPE: DNA

<213> ORGANISM: Artificial Sequence
<220> FEATURE:
<223> OTHER INFORMATION: Recombinant expression cassette

<400> SEQUENCE: 16

```
ttagttgaac tcgaacttct tgtacttgca gttgagcttt tgctcggcga atgtgatggc     60
gtcggagagt ggcaccagtc cctgcaggat caaggccaag agcttcagca agttgttgtg    120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaaacgat     300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccgggt    1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatt   1920
gggtcatcta gattcgaaag cggccgcgac tagtgagctc gtcgacgtag cctttgaat    1980
tccgcgcgct tcggaccggg atccgcgccc gatggtggga cggtatgaat aatccggaat   2040
atttataggt tttttttatta caaaactgtt acgaaaacag taaaatactt atttatttgc   2100
gagatggtta tcatttttaat tatctccatg atctattaat attccggagt atacatcgat   2160
gttgacccca acaaaagatt tataattaat cataatcacg aacaacaaca agtcaatgaa   2220
```

```
acaaataaac aagttgtcga taaaacattc ataaatgaca cagcaacata caattcttgc    2280
ataataaaaa tttaaatgac atcatatttg agaataacaa atgacattat ccctcgattg    2340
tgttttacaa gtagaattct acccgtaaag cgagtttagt tttgaaaaac aaatgacatc    2400
atttgtataa tgacatcatc ccctgattgt gttttacaag tagaattcta tccgtaaagc    2460
gagttcagtt ttgaaaacaa atgagtcata cctaaacacg ttaataatct tctgatatca    2520
gcttatgact caagttatga gccgtgtgca aaacatgaga taagtttatg acatcatcca    2580
ctgatcgtgc gttacaagta gaattctact cgtaaagcca gttcggttat gagccgtgtg    2640
caaaacatga catcagctta tgactcatac ttgattgtgt tttacgcgta gaattctact    2700
cgtaaagcga gttcggttat gagccgtgtg caaaacatga catcagctta tgagtcataa    2760
ttaatcgtgc gttacaagta gaattctact cgtaaagcga gttgaaggat catatttagt    2820
tgcgtttatg agataagatt gaaagcacgt gtaaaatgtt tcccgcgcgt tggcacaact    2880
atttacaatg cggccaagtt ataaaagatt ctaatctgat atgttttaaa acacctttgc    2940
ggcccgagtt gtttgcgtac gtgactagcg aagaagatgt gtggaccgca gaacagatag    3000
taaaacaaaa ccctagtatt ggagcaataa tcgatgagct cgtcgacgta ggcctttgaa    3060
ttccgcgcgc ttcggaccgg gatccaaaaa catcgattag ggtgactgaa ggttacattg    3120
gggtaggtta tggttaatac gtaatggttt aacaccaaaa cgatatcatg gattttatat    3180
aaggtgtaat aatatttttA atgagtggac gcgtcgggtc aatgtcctgc ctattgacgt    3240
cataacatat taggtgatta tattaaaaat agtttaaact caaatattac ttgcaagttt    3300
aagtttcatc ataatctgat cataagtttc acccaaacag aaaccaaaag cataactatc    3360
gaatatcttt agcttcccat gaagaaagat taccgtaacc atcactagga ttttatacga    3420
ttgtagaaaa taaagtattc tcagtctctt ttcagagcgc tataaaaagg ggtgcattct    3480
cggtaagagt acagttgaac tcacatcgag ttaactccac gctgcagtct cgagatacgg    3540
acctttaatt caacccaaca caatatatta tagttaaata agaattatta tcaaatcatt    3600
tgtatattaa ttaaaatact atactgtaaa ttacatttta tttacaatca ctcgac        3656
```

<210> SEQ ID NO 17
<211> LENGTH: 3541
<212> TYPE: DNA
<213> ORGANISM: Artificial Sequence
<220> FEATURE:
<223> OTHER INFORMATION: Recombinant expression cassette

<400> SEQUENCE: 17

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg acgagtact tgtatgtcag     480 agtgctcttc ttgttcacga tgaggttcag gttatcaacg acgtacttgt tgggagggtt     540
gtccgggaat tggacggact ccgagtactt gaggatctgg gaaacgtatg gcgagacgaa     600
```

```
gaagttgtta gaggcggttt cgatctcgtt tgattccttg cggctcagca tgatgggcaa        660
agtgaagagg ttcttgtcct ggtacatctc gtacaacttc gacaagagga atccacactt        720
acgctcgccg agtgattgca gcaaggtcac gaaggttgtc tgagcgtagt acatatcgag        780
gttgaagtag gaggtcagag cggccttgaa tgtgtggtgg acgtccacga agtgacactt        840
cttgcagttt tgagcggcgg tctcatcgtt gcagacgtcc tgtgagtgtg ggatttcgat        900
gccagtctcc ttaaccaggt tgtagctgat catgaagcgg atcttatcga aggtcacaac        960
gaacacacgg ttgtcaacca tgtagtagtt gtttgtgtac tcgtagacca cgttagagac       1020
gtacttggcg aagatgattt cgaaaggctt caccctcggac ttcttaacga cgaacatgta       1080
gtaaccggtt tcagacatgt gatcggagaa tctgttcgag ttgtagtcgt tatcgtcgaa       1140
cctcatcagg taggggcga agtcgtttgt gaagtagtga gtgatctcct gggtggaagc       1200
cactgtacag atgttagtgt tgtggttgat ggtttgttcc agtgtagcgc atgactggat       1260
ggtgctcttc ttgtacttag gtctcaactt gatcttgttg aattgaccca caactccctg       1320
ggagttatcc aggtactcgt ccaacttcct cttggtgcct gtggccgacg gctgttgac        1380 accagcagag tgttcgaagg actcggcgtg gtaagctgag ctaggagagg ttgttcgac        1440 cactggctgt tcgagtgact cgctgtagta ggcagaggac acagcttcct ccaggttgtc       1500
agtggtcttg agcagacact ccaccaaatc gttgtcagtg agcgagttaa ctgaggcgag       1560
gaagttgcta cgcgcagcgg tttcagagtc ggagatgaca gtatcagctc cgtccggggt       1620
tgggtggttg tagtaagaca agtaatcgtt aggttgcttg tcgcagaact ccgagtatga       1680
gttgtcgaag ctagcacgag agggagtgct ggcagaggtg taggaagcgt tgaagttgat       1740
ttgagtcatg gtgacctggt tgttcacgat cttatcgcca cctgtgtcca cctgcagttg       1800
ctgggcctca gcgcaggctg aagtggcctc acaggagtag gggctggaag cacagttgga       1860
agtcatgatg ttttcttgga cgttcaggac gtggctggat gtacggatca tagatctatc       1920
tagattcgaa agcggccgcg actagtgagc tcgtcgacgt aggcctttga attccgcgcg       1980
cttcggaccg ggatccgcgc ccgatggtgg gacggtatga ataatccgga atatttatag       2040 gttttttttat tacaaaactg ttacgaaaac agtaaaatac ttatttattt gcagatggt       2100 tatcatttta attatctcca tgatctatta atattccgga gtatacatcg atgttgaccc       2160
caacaaaaga tttataatta atcataatca cgaacaacaa caagtcaatg aaacaaataa       2220
acaagttgtc gataaaacat tcataaatga cacagcaaca tacaattctt gcataataaa       2280
aatttaaatg acatcatatt tgagaataac aaatgacatt atccctcgat tgtgttttac       2340
aagtagaatt ctacccgtaa agcgagttta gttttgaaaa acaaatgaca tcatttgtat       2400
aatgacatca tccctgatt tgtgtttaca agtagaattc tatccgtaaa gcgagttcag        2460
ttttgaaaac aaatgagtca tacctaaaca cgttaataat cttctgatat cagcttatga       2520
ctcaagttat gagccgtgtg caaaacatga gataagttta tgacatcatc cactgatcgt       2580
gcgttacaag tagaattcta ctcgtaaagc cagttcggtt atgagccgtg tgcaaaacat       2640
gacatcagct tatgactcat acttgattgt gttttacgcg tagaattcta ctcgtaaagc       2700
gagttcggtt atgagccgtg tgcaaaacat gacatcagct tatgagtcat aattaatcgt       2760
gcgttacaag tagaattcta ctcgtaaagc gagttgaagg atcatattta gttgcgttta       2820
tgagataaga ttgaaagcac gtgtaaaatg tttcccgcgc gttggcacaa ctatttacaa       2880
tgcggccaag ttataaaaga ttctaatctg atatgtttta aaacaccttt gcggcccgag       2940
ttgtttgcgt acgtgactag cgaagaagat gtgtggaccg cagaacagat agtaaaacaa       3000
```

| | |
|---|---|
| aaccctagta ttggagcaat aatcgatgag ctcgtcgacg taggcctttg aattccgcgc | 3060 |
| gcttcggacc gggatcggta ccaaattccg ttttgcgacg atgcagagtt tttgaacagg | 3120 |
| ctgctcaaac acatagatcc gtacccgctc agtcggatgt attacaatgc agccaatacc | 3180 |
| atgttttaca cgactatgga aaactatgcc gtgtccaatt gcaagttcaa cattgaggat | 3240 |
| tacaataaca tatttaaggt gatggaaaat attaggaaac acagcaacaa aaattcaaac | 3300 |
| gaccaagacg agttaaacat atatttggga gttcagtcgt cgaatgcaaa gcgtaaaaaa | 3360 |
| tattaataag gtaaaaatta cagctacata aattacacaa tttaaactgc agtctggaga | 3420 |
| tacgaccttt taattcaacc caacacaata tattatagtt aaataagaat tattatcaaa | 3480 |
| tcatttgtat attaattaaa atactatact gtaaattaca ttttatttac aatcactcga | 3540 |
| c | 3541 |

<210> SEQ ID NO 18
<211> LENGTH: 3512
<212> TYPE: DNA
<213> ORGANISM: Artificial Sequence
<220> FEATURE:
<223> OTHER INFORMATION: Recombinant expression cassette

<400> SEQUENCE: 18

| | |
|---|---|
| ttagttgaac tcgaacttct tgtacttgca gttgagcttt tgctcggcga atgtgatggc | 60 |
| gtcggagagt ggcaccagtc cctgcaggat caaggccaag agcttcagca agttgttgtg | 120 |
| cagtgtagtt gactcgcgac ggttgacctt gccgatcacg aacatgtggt gcttgaatct | 180 |
| gttgtacttt tggatgacct ggctcacatc aacgtccttg atttcgccag agatccagta | 240 |
| gaactccttg ttcttcttag cgatggtcag cctttcctcg ttcttgaagg acaaacgat | 300 |
| gaagttgtga cccttaacgt tatcgacgtt ttgagtcaag tactgctcaa cgatgtgcat | 360 |
| gcttccgtct tccttcttga ccttcttgag gttctcggcg ttgttgttag aagcgatgtt | 420 |
| gtcgtggtac ttgtagttgt tgaagagcag gttagcgacg gacgagtact tgtatgtcag | 480 |
| agtgctcttc ttgttcacga tgaggttcag gttatcaacg acgtacttgt tgggagggtt | 540 |
| gtccgggaat tggacggact ccgagtactt gaggatctgg gaaacgtatg gcgagacgaa | 600 |
| gaagttgtta gaggcggttt cgatctcgtt tgattccttg cggctcagca tgatgggcaa | 660 |
| agtgaagagg ttcttgtcct ggtacatctc gtacaacttc gacaagagga atccacactt | 720 |
| acgctcgccg agtgattgca gcaaggtcac gaaggttgtc tgagcgtagt acatatcgag | 780 |
| gttgaagtag gaggtcagag cggccttgaa tgtgtggtgg acgtccacga agtgacactt | 840 |
| cttgcagttt tgagcggcgg tctcatcgtt gcagacgtcc tgtgagtgtg ggatttcgat | 900 |
| gccagtctcc ttaaccaggt tgtagctgat catgaagcgg atcttatcga aggtcacaac | 960 |
| gaacacacgg ttgtcaacca tgtagtagtt gtttgtgtac tcgtagacca cgttagagac | 1020 |
| gtacttggcg aagatgattt cgaaaggctt cacctcggac ttcttaacga cgaacatgta | 1080 |
| gtaaccggtt tcagacatgt gatcggagaa tctgttcgag ttgtagtcgt tatcgtcgaa | 1140 |
| cctcatcagg taggggcga agtcgtttgt gaagtagtga gtgatctcct gggtggaagc | 1200 |
| cactgtacag atgttagtgt tgtggttgat ggtttgttcc agtgtagcgc atgactggat | 1260 |
| ggtgctcttc ttgtacttag gtctcaactt gatcttgttg aattgaccca caactccctg | 1320 |
| ggagttatcc aggtactcgt ccaacttcct cttggtgcct gtggccgacg gctggttgac | 1380 |
| accagcagag tgttcgaagg actcggcgtg gtaagctgag ctaggagagg gttgttcgac | 1440 |

```
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt     1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagatgcatt cgcgaggtac cgagctcgaa ttcactggcc gtcgttttac aacgtcgtga    1980
ctggaaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca cccctttta tagcgctctg aaaagagact gagaatactt tattttctac     2160
aatcgtataa aatcctagtg atggttacgg taatctttct tcatgggaag ctaaagatat    2220
tcgatagtta tgcttttggt ttctgtttgg gtgaaactta tgatcagatt atgatgaaac    2280
ttaaacttgc aagtaatatt tgagtttaaa ctattttaa tataatcacc taatatgtta     2340
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttgta tacatcgatg ttgaccccaa     2520
caaaagattt ataattaatc ataatcacga acaacaacaa gtcaatgaaa caaataaaca    2580
agttgtcgat aaaacattca taaatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg     2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaatgtttt cccgcgcgtt ggcacaacta tttacaatgc    3240
ggccaagtta taaagattc taatctgata tgttttaaaa cacctttgcg gcccgagttg     3300
tttgcgtacg tgactagcga agaagatgtg tggaccgcag aacagatagt aaaacaaaac    3360
cctagtattg gagcaataat cgatgagctc atacggacct taattcaac ccaacacaat     3420
atattatagt taaataagaa ttattatcaa atcatttgta tattaattaa aatactatac    3480
tgtaaattac attttatta caatcactcg ac                                   3512
```

<210> SEQ ID NO 19
<211> LENGTH: 4005
<212> TYPE: DNA
<213> ORGANISM: Artificial Sequence
<220> FEATURE:
<223> OTHER INFORMATION: Recombinant expression cassette

<400> SEQUENCE: 19

```
ttagttgaac tcgaacttct tgtacttgca gttgagcttt tgctcggcga atgtgatggc    60
gtcggagagt ggcaccagtc cctgcaggat caaggccaag agcttcagca agttgttgtg   120
cagtgtagtt gactcgcgac ggttgacctt gccgatcacg aacatgtggt gcttgaatct   180
gttgtacttt tggatgacct ggctcacatc aacgtccttg atttcgccag agatccagta   240
gaactccttg ttcttcttag cgatggtcag cctttcctcg ttcttgaagg acaacacgat   300
gaagttgtga cccttaacgt tatcgacgtt ttgagtcaag tactgctcaa cgatgtgcat   360
gcttccgtct tccttcttga ccttcttgag gttctcggcg ttgttgttag aagcgatgtt   420
gtcgtggtac ttgtagttgt tgaagagcag gttagcgacg gacgagtact tgtatgtcag   480
agtgctcttc ttgttcacga tgaggttcag gttatcaacg acgtacttgt gggagggtt    540 gtccgggaat tggacggact ccgagtactt gaggatctgg gaaacgtatg gcagacgaa    600 gaagttgtta gaggcggttt cgatctcgtt tgattccttg cggctcagca tgatgggcaa   660
agtgaagagg ttcttgtcct ggtacatctc gtacaacttc gacaagagga atccacactt   720
acgctcgccg agtgattgca gcaaggtcac gaaggttgtc tgagcgtagt acatatcgag   780
gttgaagtag gaggtcagag cggccttgaa tgtgtggtgg acgtccacga agtgacactt   840
cttgcagttt tgagcggcgg tctcatcgtt gcagacgtcc tgtgagtgtg ggatttcgat   900
gccagtctcc ttaaccaggt tgtagctgat catgaagcgg atcttatcga aggtcacaac   960
gaacacacgg ttgtcaacca tgtagtagtt gtttgtgtac tcgtagacca cgttagagac  1020
gtacttggcg aagatgattt cgaaaggctt cacctcggac ttcttaacga cgaacatgta  1080
gtaaccggtt tcagacatgt gatcggagaa tctgttcgag ttgtagtcgt tatcgtcgaa  1140
cctcatcagg taggggcga agtcgtttgt gaagtagtga gtgatctcct gggtggaagc  1200
cactgtacag atgttagtgt tgtggttgat ggtttgttcc agtgtagcgc atgactggat  1260
ggtgctcttc ttgtacttag gtctcaactt gatcttgttg aattgaccca caactccctg  1320
ggagttatcc aggtactcgt ccaacttcct cttggtgcct gtggccgacg gctggttgac  1380
accagcagag tgttcgaagg actcggcgtg gtaagctgag ctaggagagg ttgttcgac   1440 cactggctgt tcgagtgact cgctgtagta ggcagaggac acagcttcct ccaggttgtc  1500
agtggtcttg agcagacact ccaccaaatc gttgtcagtg agcgagttaa ctgaggcgag  1560
gaagttgcta gcggcagcgg tttcagagtc ggagatgaca gtatcagctc cgtccggggt  1620
tgggtggttg tagtaagaca agtaatcgtt aggttgcttg tcgcagaact ccgagtatga  1680
gttgtcgaag ctagcacgag agggagtgct ggcagaggtg taggaagcgt tgaagttgat  1740
ttgagtcatg gtgacctggt tgttcacgat cttatcgcca cctgtgtcca cctgcagttg  1800
ctgggcctca gcgcaggctg aagtggcctc acaggagtag gggctggaag cacagttgga  1860
agtcatgatg ttttcttgga cgttcaggac gtggctggat gtacggatca tagatctatc  1920
tagatgcatt cgcgaggtac cgagctcgaa ttcactggcc gtcgttttac aacgtcgtga  1980
ctgggaaaac cctggcgtta cccaacttaa tcgccttgca gcacatcccc ctttcgccag  2040
ctgctagcac catggctcga gcgtggagtt aactcgatgt gagttcaact gtactcttac  2100
cgagaatgca ccccttttta tagcgctctg aaaagagact gagaatactt tattttctac  2160
aatcgtataa aatcctagtg atggttacgg taatctttct tcatgggaag ctaaagatat  2220
tcgatagtta tgcttttggt ttctgtttgg gtgaaactta tgatcagatt atgatgaaac  2280
ttaaacttgc aagtaatatt tgagtttaaa ctattttaa tataatcacc taatatgtta   2340
```

-continued

```
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttgta tacatcgatg ttgaccccaa    2520
caaaagattt ataattaatc ataatcacga acaacaacaa gtcaatgaaa caaataaaca    2580
agttgtcgat aaaacattca taaatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgatgagctc gtcgacgtag gcctttgaat tccgcgcgct    3420
tcggaccggg atccaaaaac atcgattagg gtgactgaag gttacattgg ggtaggttat    3480
ggttaatacg taatggttta acaccaaaac gatatcatgg atttatata aggtgtaata    3540 atatttttaa tgagtggacg cgtcgggtca atgtcctgcc tattgacgtc ataacatatt    3600
aggtgattat attaaaaata gtttaaactc aaatattact tgcaagttta gtttcatca    3660 taatctgatc ataagtttca cccaaacaga accaaaagc ataactatcg aatatctta    3720 gcttcccatg aagaaagatt accgtaacca tcactaggat tttatacgat tgtagaaaat    3780
aaagtattct cagtctcttt tcagagcgct ataaaagggg gtgcattctc ggtaagagta    3840
cagttgaact cacatcgagt taactccacg ctgcagtctc gagatacgga ccttaattc    3900 aacccaacac aatatattat agttaaataa gaattattat caaatcattt gtatattaat    3960
taaaatacta tactgtaaat tacatttat ttacaatcac tcgac                     4005
```

<210> SEQ ID NO 20
<211> LENGTH: 3898
<212> TYPE: DNA
<213> ORGANISM: Artificial Sequence
<220> FEATURE:
<223> OTHER INFORMATION: Recombinant expression cassette

<400> SEQUENCE: 20

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag ccttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
```

```
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg ttgttcgac    1440 cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccgggt    1620 tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagatgcatt cgcgaggtac cgagctcgaa ttcactggcc gtcgttttac aacgtcgtga   1980
ctgggaaaac cctggcgtta cccaacttaa tcgccttgca gcacatcccc ctttcgccag   2040
ctgctagcac catggctcga gcgtggagtt aactcgatgt gagttcaact gtactcttac   2100
cgagaatgca ccccttttta tagcgctctg aaaagagact gagaatactt tattttctac   2160
aatcgtataa aatcctagtg atggttacgg taatctttct tcatgggaag ctaaagatat   2220
tcgatagtta tgcttttggt ttctgtttgg gtgaaactta tgatcagatt atgatgaaac   2280
ttaaacttgc aagtaatatt tgagtttaaa ctattttta tataatcacc taatatgtta   2340
tgacgtcaat aggcaggaca ttgacccgac gcgtccactc attaaaaata ttattacacc   2400
ttatataaaa tccatgatat cgttttggtg ttaaaccatt acgtattaac cataacctac   2460
cccaatgtaa ccttcagtca ccctaatcga tgttttgta tacatcgatg ttgaccccaa   2520
caaaagattt ataattaatc ataatcacga acaacaacaa gtcaatgaaa caaataaaca   2580
agttgtcgat aaaacattca taaatgacac agcaacatac aattcttgca taataaaaat   2640
ttaaatgaca tcatatttga gaataacaaa tgacattatc cctcgattgt gttttacaag   2700
tagaattcta cccgtaaagc gagtttagtt ttgaaaaaca aatgacatca tttgtataat   2760
```

-continued

```
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgatgagctc gtcgacgtag gcctttgaat tccgcgcgct    3420
tcggaccggg atcggtacca aattccgttt tgcgacgatg cagagttttt gaacaggctg    3480
ctcaaacaca tagatccgta cccgctcagt cggatgtatt acaatgcagc caataccatg    3540
ttttacacga ctatggaaaa ctatgccgtg tccaattgca agttcaacat tgaggattac    3600
aataacatat ttaaggtgat ggaaaatatt aggaaacaca gcaacaaaaa ttcaaacgac    3660
caagacgagt taaacatata tttgggagtt cagtcgtcga atgcaaagcg taaaaaatat    3720
taataaggta aaaattacag ctacataaat tacacaattt aaactgcagt ctggagatac    3780 ggaccttttaa ttcaacccaa cacaatatat tatagttaaa taagaattat tatcaaatca    3840
tttgtatatt aattaaaaata ctatactgta aattacattt tatttacaat cactcgac     3898
```

<210> SEQ ID NO 21
<211> LENGTH: 881
<212> TYPE: DNA
<213> ORGANISM: Autographa californica nucleopolyhedrovirus

<400> SEQUENCE: 21

```
atcgatgttg accccaacaa aagatttata attaatcata atcacgaaca acaacaagtc      60
aatgaaacaa ataaacaagt tgtcgataaa acattcataa atgacacagc aacatacaat     120
tcttgcataa taaaaattta aatgacatca tatttgagaa taacaaatga cattatccct     180
cgattgtgtt ttacaagtag aattctaccc gtaaagcgag tttagtttttg aaaaacaaat     240 gacatcattt gtataatgac atcatcccct gattgtgttt tacaagtaga attctatccg     300
taaagcgagt tcagttttga aaacaaatga gtcataccta aacacgttaa taatcttctg     360
atatcagctt atgactcaag ttatgagccg tgtgcaaaac atgagataag tttatgacat     420
catccactga tcgtgcgtta caagtagaat tctactcgta aagccagttc ggttatgagc     480
cgtgtgcaaa acatgacatc agcttatgac tcatacttga ttgtgtttta cgcgtagaat     540
tctactcgta aagcgagttc ggttatgagc cgtgtgcaaa acatgacatc agcttatgag     600
tcataattaa tcgtgcgtta caagtagaat tctactcgta aagcgagttg aaggatcata     660
tttagttgcg tttatgagat aagattgaaa gcacgtgtaa aatgtttccc gcgcgttggc     720
acaactattt acaatgcggc caagttataa aagattctaa tctgatatgt tttaaaacac     780
ctttgcggcc cgagttgttt gcgtacgtga ctagcgaaga agatgtgtgg accgcagaac     840
agatagtaaa acaaaaccct agtattggag caataatcga t                         881
```

<210> SEQ ID NO 22
<211> LENGTH: 2124

```
<212> TYPE: DNA
<213> ORGANISM: Artificial Sequence
<220> FEATURE:
<223> OTHER INFORMATION: Recombinant DNA construct fusing the Ac-ie-01
      cDNA to the polh promoter

<400> SEQUENCE: 22
atcatggaga taattaaaat gataaccatc tcgcaaataa ataagtattt tactgttttc      60
gtaacagttt tgtaataaaa aaacctataa atattccgga ttattcatac cgtcccacca     120
tcgggcgcgg atcccggtcc gaagcgcgcg gaattcaaag gcctacgtcg acgagctcac     180
tagtcgcggc cgctttcgaa tctagataga tctatgatcc gtacatccag ccacgtcctg     240
aacgtccaag aaaacatcat gacttccaac tgtgcttcca gcccctactc ctgtgaggcc     300
acttcagcct gcgctgaggc ccagcaactg caggtggaca caggtggcga taagatcgtg     360
aacaaccagg tcaccatgac tcaaatcaac ttcaacgctt cctacacctc tgccagcact     420
ccctctcgtg ctagcttcga caactcatac tcggagttct gcgacaagca acctaacgat     480
tacttgtctt actacaacca cccaaccccg gacggagctg atactgtcat ctccgactct     540
gaaaccgctg ccgctagcaa cttcctcgcc tcagttaact cgctcactga caacgatttg     600
gtggagtgtc tgctcaagac cactgacaac ctggaggaag ctgtgtcctc tgcctactac     660
agcgagtcac tcgaacagcc agtggtcgaa caaccctctc ctagctcagc ttaccacgcc     720
gagtccttcg aacactctgc tggtgtcaac cagccgtcgg ccacaggcac caagaggaag     780
ttggacgagt acctggataa ctcccaggga gttgtgggtc aattcaacaa gatcaagttg     840
agacctaagt acaagaagag caccatccag tcatgcgcta cactggaaca aaccatcaac     900
cacaacacta acatctgtac agtggcttcc acccaggaga tcactcacta cttcacaaac     960
gacttcgccc cctacctgat gaggttcgac gataacgact acaactcgaa cagattctcc    1020
gatcacatgt ctgaaaccgg ttactacatg ttcgtcgtta agaagtccga ggtgaagcct    1080
ttcgaaatca tcttcgccaa gtacgtctct aacgtggtct acgagtacac aaacaactac    1140
tacatggttg acaaccgtgt gttcgttgtg accttcgata agatccgctt catgatcagc    1200
tacaacctgg ttaaggagac tggcatcgaa atcccacact cacaggacgt ctgcaacgat    1260
gagaccgccg ctcaaaactg caagaagtgt cacttcgtgg acgtccacca cacattcaag    1320
gccgctctga cctcctactt caacctcgat atgtactacg ctcagacaac cttcgtgacc    1380
ttgctgcaat cactcggcga gcgtaagtgt ggattcctct tgtcgaagtt gtacgagatg    1440
taccaggaca agaacctctt cactttgccc atcatgctga gccgcaagga atcaaacgag    1500
atcgaaaccg cctctaacaa cttcttcgtc tcgccatacg tttcccagat cctcaagtac    1560
tcggagtccg tccaattccc ggacaaccct cccaacaagt acgtcgttga taacctgaac    1620
ctcatcgtga acaagaagag cactctgaca tacaagtact cgtccgtcgc taacctgctc    1680
ttcaacaact acaagtacca cgacaacatc gcttctaaca caacgccga gaacctcaag    1740
aaggtcaaga aggaagacgg aagcatgcac atcgttgagc agtacttgac tcaaaacgtc    1800
gataacgtta agggtcacaa cttcatcgtg ttgtccttca agaacgagga aaggctgacc    1860
atcgctaaga agaacaagga gttctactgg atctctggcg aaatcaagga cgttgatgtg    1920
agccaggtca tccaaaagta caacagattc aagcaccaca tgttcgtgat cggcaaggtc    1980
aaccgtcgcg agtcaactac actgcacaac aacttgctga gctcttggc cttgatcctg    2040
cagggactgg tgccactctc cgacgccatc acattcgccg agcaaaagct caactgcaag    2100
tacaagaagt tcgagttcaa ctaa                                           2124
```

<210> SEQ ID NO 23
<211> LENGTH: 911
<212> TYPE: DNA
<213> ORGANISM: Artificial Sequence
<220> FEATURE:
<223> OTHER INFORMATION: Recombinant DNA construct fusing the GFP cDNA
      to the polh promoter

<400> SEQUENCE: 23

```
atcatggaga taattaaaat gataaccatc tcgcaaataa ataagtattt tactgttttc      60
gtaacagttt tgtaataaaa aaacctataa atattccgga ttattcatac cgtcccacca     120
tcgggcgcgg atccaaggcc actagtgcgg ccgctctgca gtctcgagca tgcggtacca     180
agcttgaatt catggtgagc aagggcgagg agctgttcac cggggtggtg cccatcctgg     240
tcgagctgga cggcgacgta acggccaca agttcagcgt gtccggcgag ggcgagggcg      300
atgccaccta cggcaagctg accctgaagt tcatctgcac caccggcaag ctgcccgtgc     360
cctggcccac cctcgtgacc accctgacct acggcgtgca gtgcttcagc cgctaccccg     420
accacatgaa gcagcacgac ttcttcaagt ccgccatgcc cgaaggctac gtccaggagc     480
gcaccatctt cttcaaggac gacggcaact acaagacccg cgccgaggtg aagttcgagg     540
gcgacaccct ggtgaaccgc atcgagctga agggcatcga cttcaaggag gacggcaaca     600
tcctggggca caagctggag tacaactaca acagccacaa cgtctatatc atggccgaca     660
agcagaagaa cggcatcatg gtgaacttca gatccgcca caacatcgag gacggcagcg      720
tgcagctcgc cgaccactac cagcagaaca cccccatcgg cgacggcccc gtgctgctgc     780
ccgacaacca ctacctgagc acccagtccg ccctgagcaa agaccccaac gagaagcgcg     840
atcacatggt cctgctggag ttcgtgaccg ccgccgggat cactctcggc atggacgagc     900
tgtacaagta a                                                          911
```

<210> SEQ ID NO 24
<211> LENGTH: 1502
<212> TYPE: DNA
<213> ORGANISM: Artificial Sequence
<220> FEATURE:
<223> OTHER INFORMATION: hr1pB2(9)p10

<400> SEQUENCE: 24

```
atcgatgttg accccaacaa aagatttata attaatcata atcacgaaca acaacaagtc      60
aatgaaacaa ataaacaagt tgtcgataaa acattcataa atgacacagc aacatacaat     120
tcttgcataa taaaaattta aatgacatca tatttgagaa taacaaatga cattatccct     180
cgattgtgtt ttacaagtag aattctaccc gtaaagcgag tttagttttg aaaaacaaat     240
gacatcattt gtataatgac atcatcccct gattgtgttt tacaagtaga attctatccg     300
taaagcgagt tcagttttga aaacaaatga gtcatacctaaacacgttaa taatcttctg     360
atatcagctt atgactcaag ttatgagccg tgtgcaaaac atgagataag tttatgacat     420
catccactga tcgtgcgtta caagtagaat tctactcgta aagccagttc ggttatgagc     480
cgtgtgcaaa acatgacatc agcttatgac tcatacttga ttgtgtttta cgcgtagaat     540
tctactcgta aagcgagttc ggttatgagc cgtgtgcaaa acatgacatc agcttatgag     600
tcataattaa tcgtgcgtta caagtagaat tctactcgta aagcgagttg aaggatcata     660
tttagttgcg tttatgagat aagattgaaa gcacgtgtaa aatgtttccc gcgcgttggc     720
acaactattt acaatgcggc caagttataa aagattctaa tctgatatgt tttaaaacac     780
```

-continued

```
ctttgcggcc cgagttgttt gcgtacgtga ctagcgaaga agatgtgtgg accgcagaac    840
agatagtaaa acaaaaccct agtattggag caataatcga tgagctcgtc gacgtaggcc    900
tttgaattcc gcgcgcttcg gaccgggatc caaaaacatc gattagggtg actgaaggtt    960
acattggggt aggttatggt taatacgtaa tggtttaaca ccaaaacgat atcatggatt   1020
ttatataagg tgtaataata tttttaatga gtggacgcgt cgggtcaatg tcctgcctat   1080
tgacgtcata acatattagg tgattatatt aaaaatagtt taaactcaaa tattacttgc   1140
aagtttaagt ttcatcataa tctgatcata agtttcaccc aaacagaaac caaaagcata   1200
actatcgaat atctttagct tcccatgaag aaagattacc gtaaccatca ctaggatttt   1260
atacgattgt agaaaataaa gtattctcag tctcttttca gagcgctata aaaaggggtg   1320
cattctcggt aagagtacag ttgaactcac atcgagttaa ctccacgctg cagtctcgag   1380
atacggacct ttaattcaac ccaacacaat atattatagt taaataagaa ttattatcaa   1440
atcatttgta tattaattaa aatactatac tgtaaattac attttattta caatcactcg   1500
ac                                                                  1502
```

```
<210> SEQ ID NO 25
<211> LENGTH: 702
<212> TYPE: DNA
<213> ORGANISM: Porcine circovirus type 2

<400> SEQUENCE: 25
atgacgtatc caaggaggcg tttccgcaga cgaagacacc gcccccgcag ccatcttggc     60
cagatcctcc gccgccgccc ctggctcgtc cacccccgcc accgttaccg ctggagaagg    120
aaaaatggca tcttcaacac ccgcctctcc cgcaccttcg gatatactgt caaggctacc    180
acagtcacaa cgccctcctg ggcggtggac atgatgagat ttaatattaa cgactttgtt    240
cccccgggag gggggaccaa caaaatctct ataccctttg aatactacag aataagaaag    300
gttaaggttg aattctggcc ctgctcccca atcacccagg gtgacagggg agtgggctcc    360
actgctgtta ttctagatga taactttgta acaaaggcca cagccctaac ctatgacccc    420
tatgtaaact actcctcccg ccatacaatc ccccaaccct tctcctacca ctcccgttac    480
ttcacaccca aacctgtact ggatagaact attgattact tccagccaaa caacaaaaaa    540
aatcagcttt ggctgaggct acaaacctct gcaaatgtag accacgtagg cctcggcact    600
gcgttcgaaa acagtaaata cgaccaggac tacaatatcc gtgtaaccat gtatgtacaa    660
ttcagagaat ttaatcttaa agaccccccca cttaaaccct aa                       702
```

```
<210> SEQ ID NO 26
<211> LENGTH: 233
<212> TYPE: PRT
<213> ORGANISM: Porcine circovirus type 2

<400> SEQUENCE: 26

Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60
```

```
Pro Ser Trp Ala Val Asp Met Met Arg Phe Asn Ile Asn Asp Phe Val
 65                  70                  75                  80

Pro Pro Gly Gly Gly Thr Asn Lys Ile Ser Ile Pro Phe Glu Tyr Tyr
                 85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Lys Asn Gln Leu Trp Leu Arg Leu Gln Thr Ser Ala Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 27
<211> LENGTH: 4550
<212> TYPE: DNA
<213> ORGANISM: Artificial Sequence
<220> FEATURE:
<223> OTHER INFORMATION: polhAc-ie-01/hrp6.9p10Cap-p10

<400> SEQUENCE: 27

```
ttagttgaac tcgaacttct tgtacttgca gttgagcttt tgctcggcga atgtgatggc      60
gtcggagagt ggcaccagtc cctgcaggat caaggccaag agcttcagca agttgttgtg    120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcagacgaa     600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
```

```
gtaaccggtt tcagacatgt gatcggagaa tctgttcgag ttgtagtcgt tatcgtcgaa    1140
cctcatcagg taggggggcga agtcgtttgt gaagtagtga gtgatctcct gggtggaagc   1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg ttgttcgac     1440 cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccggggt    1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagattcgaa agcggccgcg actagtgagc tcgtcgacgt aggcctttga attccgcgcg    1980
cttcggaccg ggatccgcgc ccgatggtgg gacggtatga ataatccgga atatttatag    2040 gttttttat tacaaaactg ttacgaaaac agtaaaatac ttatttattt gcagatggt    2100 tatcatttta attatctcca tgatctatta atattccgga gtataccta  ccgtaaagcg    2160 agtttagttt tgaaaacaa atgacatcat ttgtataatg acatcatccc ctgattgtgt     2220
tttacaagta gaattctatc cgtaaagcga gttcagtttt gaaaacaaat gagtcatacc    2280
taaacacgtt aataatcttc tgatatcagc ttatgactca agttatgagc cgtgtgcaaa    2340
acatgagata agtttatgac atcatccact gatcgtgcgt tacaagtaga attctactcg    2400
taaagccagt tcggttatga gccgtgtgca aaacatgaca tcagcttatg actcatactt    2460
gattgtgttt tacgcgtaga attctactcg taaagcgagt tcggttatga gccgtgtgca    2520
aaacatgaca tcagcttatg agtcataatt aatcgtgcgt tacaagtaga attctactcg    2580
taaagcgagt tgaaggatca tatttagttg cgtttatgag ataagattga aagcacgtgt    2640
aaaatgtttc cgagctcgtc gacgtaggcc tttgaattcc gcgcgcttcg gacccgggatc   2700 ggtaccaaat tccgttttgc gacgatgcag agttttgaa caggctgctc aaacacatag     2760
atccgtaccc gctcagtcgg atgtattaca atgcagccaa taccatgttt tacacgacta    2820
tggaaaacta tgccgtgtcc aattgcaagt tcaacattga ggattacaat aacatattta    2880
aggtgatgga aaatattagg aaacacagca acaaaaattc aaacgaccaa gacgagttaa    2940
acatatattt gggagttcag tcgtcgaatg caaagcgtaa aaaatattaa taaggtaaaa    3000
attacagcta cataaaattac acaattttaaa ctgcagtctg gagatacgga cctttaattc    3060
aacccaacac aatatattat agttaaataa gaattattat caaatcattt gtatattaat    3120
taaaatacta tactgtaaat tacatttttat ttacaatcac tcgacctcga gatgacgtat    3180
ccaaggaggc gttccgcag acgaagacac cgccccgca gccatcttgg ccagatcctc       3240
cgccgccgcc cctggctcgt ccaccccgc caccgttacc gctggagaag gaaaaatggc     3300
atcttcaaca cccgcctctc ccgcaccttg ggatatactg tcaaggctac cacagtcaca    3360
acgccctcct gggcggtgga catgatgaga tttaatatta acgactttgt tccccccggga    3420 gggggaccca acaaaatctc tatacccttt gaatactaca gaataagaaa ggttaaggtt    3480
```

```
gaattctggc cctgctcccc aatcacccag ggtgacaggg gagtgggctc cactgctgtt      3540
attctagatg ataactttgt aacaaaggcc acagccctaa cctatgaccc ctatgtaaac      3600
tactcctccc gccatacaat cccccaaccc ttctcctacc actcccgtta cttcacaccc      3660
aaacctgtac tggatagaac tattgattac ttccagccaa acaacaaaaa aaatcagctt      3720
tggctgaggc tacaaacctc tgcaaatgta gaccacgtag gcctcggcac tgcgttcgaa      3780
aacagtaaat acgaccagga ctacaatatc cgtgtaacca tgtatgtaca attcagagaa      3840
tttaatctta aagacccccc acttaaaccc taaccatgga agcttatgaa tcgttttttaa     3900 aataacaaat caattgtttt ataatattcg tacgattctt tgattatgta ataaaatgtg      3960
atcattagga agattacgaa aaatatataaa aatatgagtt ctgtgtgtat aacaaatgct     4020
gtaaacgcca caattgtgtt tgttgcaaat aaacccatga ttatttgatt aaaattgttg      4080
ttttctttgt tcatagacaa tagtgtgttt tgcctaaacg tgtactgcat aaactccatg      4140
cgagtgtata gcgagctagt ggctaacgct tgccccacca agtagattc gtcaaaatcc       4200 tcaatttcat caccctcctc caagtttaac atttggccgt cggaattaac ttctaaagat      4260
gccacataat ctaataaatg aaatagagat tcaaacgtgg cgtcatcgtc cgtttcgacc      4320
atttccgaaa agaactcggg cataaactct atgatttctc tggacgtggt gttgtcgaaa      4380
ctctcaaagt acgcagtcag gaacgtgcgc gacatgtcgt cgggaaactc gcgcggaaac      4440
atgttgttgt aaccgaacgg gtcccatagc gccaaaacca aatctgccag cgtcaataga     4500
atgagcacga tgccgacaat ggagctggct tggatagcga ttcgagttaa                4550
```

<210> SEQ ID NO 28
<211> LENGTH: 836
<212> TYPE: DNA
<213> ORGANISM: Artificial sequence
<220> FEATURE:
<223> OTHER INFORMATION: polhCap

<400> SEQUENCE: 28

```
atcatggaga taattaaaat gataaccatc tcgcaaataa ataagtattt tactgttttc       60
gtaacagttt tgtaataaaa aaacctataa atattccgga ttattcatac cgtcccacca      120
tcgggcgcgg atccatgacg tatccaagga ggcgtttccg cagacgaaga caccgccccc      180
gcagccatct tggccagatc ctccgccgcc gcccctggct cgtccacccc cgccaccgtt      240
accgctggag aaggaaaaat ggcatcttca cacccgcct ctcccgcacc ttcggatata       300
ctgtcaaggc taccacagtc acaacgccct cctgggcgt ggacatgatg agatttaata      360
ttaacgactt tgttcccccg ggagggggga ccaacaaaat ctctataccc tttgaatact      420
acagaataag aaaggttaag gttgaattct ggccctgctc cccaatcacc cagggtgaca     480
ggggagtggg ctccactgct gttattctag atgataactt tgtaacaaag gccacagccc      540
taacctatga cccctatgta aactactcct cccgccatac aatcccccaa cccttctcct     600
accactcccg ttacttcaca cccaaacctg tactggatag aactattgat tacttccagc     660
caaacaacaa aaaaaatcag ctttggctga ggctacaaac ctctgcaaat gtagaccacg     720
taggcctcgg cactgcgttc gaaaacagta aatacgacca ggactacaat atccgtgtaa     780
ccatgtatgt acaattcaga gaatttaatc ttaaagaccc cccacttaaa ccctaa        836
```

<210> SEQ ID NO 29
<211> LENGTH: 3873
<212> TYPE: DNA

<213> ORGANISM: Artificial Sequence
<220> FEATURE:
<223> OTHER INFORMATION: polhAc-ie-01/hr1p6.9p10Cap

<400> SEQUENCE: 29

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg acgagtact  tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcgagacgaa     600
gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg taggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg ttgttcgac     1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt    1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagattcgaa agcggccgcg actagtgagc tcgtcgacgt aggcctttga attccgcgcg    1980
cttcggaccg ggatccgcgc ccgatggtgg gacggtatga ataatccgga atatttatag    2040
gttttttttat tacaaaactg ttacgaaaac agtaaaatac ttatttatttt gcgagatggt    2100
tatcatttta attatctcca tgatctatta atattccgga gtataccta  ccgtaaagcg    2160
agtttagttt tgaaaaacaa atgacatcat ttgtataatg acatcatccc ctgattgtgt    2220
```

```
tttacaagta gaattctatc cgtaaagcga gttcagtttt gaaaacaaat gagtcatacc   2280
taaacacgtt aataatcttc tgatatcagc ttatgactca agttatgagc cgtgtgcaaa   2340
acatgagata agtttatgac atcatccact gatcgtgcgt tacaagtaga attctactcg   2400
taaagccagt tcggttatga gccgtgtgca aaacatgaca tcagcttatg actcatactt   2460
gattgtgttt tacgcgtaga attctactcg taaagcgagt tcggttatga gccgtgtgca   2520
aaacatgaca tcagcttatg agtcataatt aatcgtgcgt tacaagtaga attctactcg   2580
taaagcgagt tgaaggatca tatttagttg cgtttatgag ataagattga aagcacgtgt   2640
aaaatgtttc cgagctcgtc gacgtaggcc tttgaattcc gcgcgcttcg gaccgggatc   2700
ggtaccaaat tccgttttgc gacgatgcag agtttttgaa caggctgctc aaacacatag   2760
atccgtaccc gctcagtcgg atgtattaca atgcagccaa taccatgttt tacacgacta   2820
tggaaaacta tgccgtgtcc aattgcaagt tcaacattga ggattacaat aacatattta   2880
aggtgatgga aaatattagg aaacacagca acaaaaattc aaacgaccaa gacgagttaa   2940
acatatattt gggagttcag tcgtcgaatg caaagcgtaa aaaatattaa taaggtaaaa   3000
attacagcta cataaattac acaatttaaa ctgcagtctg gagatacgga cctttaattc   3060
aacccaacac aatatattat agttaaataa gaattattat caaatcattt gtatattaat   3120
taaaatacta tactgtaaat tacattttat ttacaatcac tcgacctcga gatgacgtat   3180
ccaaggaggc gtttccgcag acgaagacac cgcccccgca gccatcttgg ccagatcctc   3240
cgccgccgcc cctggctcgt ccacccccgc caccgttacc gctggagaag gaaaaatggc   3300
atcttcaaca cccgcctctc ccgcaccttc ggatatactg tcaaggctac cacagtcaca   3360
acgccctcct gggcggtgga catgatgaga tttaatatta acgactttgt tcccccggga   3420
ggggggacca acaaaatctc tatacccttt gaatactaca gaataagaaa ggttaaggtt   3480
gaattctggc cctgctcccc aatcacccag ggtgacaggg gagtgggctc cactgctgtt   3540
attctagatg ataactttgt aacaaaggcc acagccctaa cctatgaccc ctatgtaaac   3600
tactcctccc gccatacaat cccccaaccc ttctcctacc actcccgtta cttcacaccc   3660
aaacctgtac tggatagaac tattgattac ttccagccaa acaacaaaaa aaatcagctt   3720
tggctgaggc tacaaacctc tgcaaatgta gaccacgtag gcctcggcac tgcgttcgaa   3780
aacagtaaat acgaccagga ctacaatatc cgtgtaacca tgtatgtaca attcagagaa   3840
tttaatctta aagacccccc acttaaaccc taa                                3873
```

<210> SEQ ID NO 30
<211> LENGTH: 1632
<212> TYPE: DNA
<213> ORGANISM: Influenza virus PR8 strain

<400> SEQUENCE: 30

```
atgaaattct tagtcaacgt tgcccttgtt tttatggtcg tatacatttc ttacatctat     60
gcggatcctg acacaatatg tataggctac catgcgaaca attcaaccga cactgttgac    120
acagtactcg agaagaatgt gacagtgaca cactctgtta acctgctcga agacagccac    180
aacggaaaac tatgtagatt aaaaggaata gccccactac aattggggaa atgtaacatc    240
gccggatggc tcttgggaaa cccagaatgc gacccactgc ttccagtgag atcatggtcc    300
tacattgtag aaacaccaaa ctctgagaat ggaatatgtt atccaggaga tttcatcgac    360
tatgaggagc tgagggagca attgagctca gtgtcatcat tcgaaagatt cgaaatattt    420
```

```
cccaaagaaa gctcatggcc caaccacaac acaaacggag taacggcagc atgctcccat      480
gaggggaaaa gcagttttta cagaaatttg ctatggctga cggagaagga gggctcatac      540
ccaaagctga aaattctta tgtgaacaaa aagggaaag aagtccttgt actgtgggt        600 attcatcacc cgcctaacag taaggaacaa cagaatctct atcagaatga aaatgcttat      660
gtctctgtag tgacttcaaa ttataacagg agatttaccc cggaaatagc agaaagaccc      720
aaagtaagag atcaagctgg gaggatgaac tattactgga ccttgctaaa acccggagac      780
acaataatat ttgaggcaaa tggaaatcta atagcaccaa tgtatgcttt cgcactgagt      840
agaggctttg gtccggcat catcacctca aacgcatcaa tgcatgagtg taacacgaag       900
tgtcaaacac ccctgggagc tataaacagc agtctcccctt accagaatat acacccagtc    960
acaataggag agtgcccaaa atacgtcagg agtgccaaat tgaggatggt tacaggacta    1020
aggaacactc cgtccattca atccagaggt ctatttggag ccattgccgg ttttattgaa    1080
gggggatgga ctggaatgat agatggatgg tatggttatc atcatcagaa tgaacaggga    1140
tcaggctatg cagcggatca aaaaagcaca caaaatgcca ttaacgggat tacaaacaag    1200
gtgaacactg ttatcgagaa aatgaacatt caattcacag ctgtgggtaa agaattcaac    1260
aaattagaaa aaggatggaa aaatttaaat aaaaagttg atgatggatt tctggacatt    1320
tggacatata atgcagaatt gttagttcta ctggaaaatg aaaggactct ggatttccat    1380
gactcaaatg tgaagaatct gtatgagaaa gtaaaaagcc aattaaagaa taatgccaaa    1440
gaaatcggaa atggatgttt tgagttctac cacaagtgtg acaatgaatg catggaaagt    1500
gtaagaaatg gactatga ttatccaaaa tattcagaag agtcaaagtt gaacagggaa     1560
aaggtagatg gagtgaaatt ggaatcaatg gggatctatc agatttctag acatcaccac    1620
caccatcact aa                                                         1632
```

<210> SEQ ID NO 31
<211> LENGTH: 10273
<212> TYPE: DNA
<213> ORGANISM: Artificial sequence
<220> FEATURE:
<223> OTHER INFORMATION: polhAc-ie-01/hr1p6.9p10MelHA

<400> SEQUENCE: 31

```
ttctctgtca cagaatgaaa attttttctgt catctcttcg ttattaatgt ttgtaattga     60
ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcgggggc tccctttagg gttccgattt agtgctttac ggcacctcga    300
ccccaaaaaa cttgattagg gtgatggttc acgtagtggg ccatcgccct gatagacggt    360
ttttcgccct ttgacgttgg agtccacgtt ctttaatagt ggactcttgt tccaaactgg    420
aacaacactc aaccctatct cggtctattc ttttgattta aagggattt tgccgatttc     480 ggcctattgg ttaaaaaatg agctgattta caaaaatttt aacgcgaatt ttaacaaaat    540
attaacgttt acaatttcag gtggcacttt tcggggaaat gtgcgcggaa ccccctatttg   600 tttattttc taaatacatt caaatatgta tccgctcatg agacaataac cctgataaat    660
gcttcaataa tattgaaaaa ggaagagtat gagtattcaa catttccgtg tcgcccttat    720 tcccttttttt gcggcatttt gccttcctgt ttttgctcac ccagaaacgc tggtgaaagt    780
aaaagatgct gaagatcagt tgggtgcacg agtgggttac atcgaactgg atctcaacag    840
```

```
cggtaagatc cttgagagtt ttcgccccga agaacgtttt ccaatgatga gcacttttaa    900
agttctgcta tgtggcgcgg tattatcccg tattgacgcc gggcaagagc aactcggtcg    960
ccgcatacac tattctcaga atgacttggt tgagtactca ccagtcacag aaaagcatct   1020
tacggatggc atgacagtaa gagaattatg cagtgctgcc ataaccatga gtgataacac   1080
tgcggccaac ttacttctga caacgatcgg aggaccgaag gagctaaccg ctttttttgca   1140
caacatgggg gatcatgtaa ctcgccttga tcgttgggaa ccggagctga atgaagccat   1200
accaaacgac gagcgtgaca ccacgatgcc tgtagcaatg gcaacaacgt tgcgcaaact   1260
attaactggc gaactactta ctctagcttc ccggcaacaa ttaatagact ggatggaggc   1320
ggataaagtt gcaggaccac ttctgcgctc ggcccttccg gctggctggt ttattgctga   1380
taaatctgga gccggtgagc gtgggtctcg cggtatcatt gcagcactgg ggccagatgg   1440
taagccctcc cgtatcgtag ttatctacac gacggggagt caggcaacta tggatgaacg   1500
aaatagacag atcgctgaga taggtgcctc actgattaag cattggtaac tgtcagacca   1560
agtttactca tatatacttt agattgattt aaaacttcat ttttaattta aaaggatcta   1620
ggtgaagatc cttttttgata atctcatgac caaaatccct taacgtgagt tttcgttcca   1680
ctgagcgtca gaccccgtag aaaagatcaa aggatcttct tgagatcctt ttttttctgcg   1740
cgtaatctgc tgcttgcaaa caaaaaaacc accgctacca gcggtggttt gtttgccgga   1800
tcaagagcta ccaactcttt ttccgaaggt aactggcttc agcagagcgc agataccaaa   1860
tactgtcctt ctagtgtagc cgtagttagg ccaccacttc aagaactctg tagcaccgcc   1920
tacatacctc gctctgctaa tcctgttacc agtggctgct gccagtggcg ataagtcgtg   1980
tcttaccggg ttggactcaa gacgatagtt accggataag cgcagcggt cgggctgaac   2040
ggggggttcg tgcacacagc ccagcttgga gcgaacgacc tacaccgaac tgagatacct   2100
acagcgtgag cattgagaaa gcgccacgct tcccgaaggg agaaaggcgg acaggtatcc   2160
ggtaagcggc agggtcggaa caggagagcg cacgagggag cttccagggg gaaacgcctg   2220
gtatctttat agtcctgtcg ggtttcgcca cctctgactt gagcgtcgat ttttgtgatg   2280
ctcgtcaggg gggcggagcc tatggaaaaa cgccagcaac gcggcctttt tacggttcct   2340
ggccttttgc tggccttttg ctcacatgtt ctttcctgcg ttatcccctg attctgtgga   2400
taaccgtatt accgcctttg agtgagctga taccgctcgc cgcagccgaa cgaccgagcg   2460
cagcgagtca gtgagcgagg aagcggaaga gcgcctgatg cggtattttc tccttacgca   2520
tctgtgcggt atttcacacc gcagaccagc cgcgtaacct ggcaaaatcg gttacggttg   2580
agtaataaat ggatgccctg cgtaagcggg tgtgggcgga caataaagtc ttaaactgaa   2640
caaaatagat ctaaactatg acaataaagt cttaaactag acagaatagt tgtaaactga   2700
aatcagtcca gttatgctgt gaaaaagcat actggacttt tgttatggct aaagcaaact   2760
cttcattttc tgaagtgcaa attgcccgtc gtattaaaga ggggcgtggc caagggcatg   2820
gtaaagacta tattcgcggc gttgtgacaa tttaccgaac aactccgcgg ccgggaagcc   2880
gatctcggct tgaacgaatt gttaggtggc ggtacttggg tcgatatcaa agtgcatcac   2940
ttcttcccgt atgcccaact ttgtatagag agccactgcg gatcgtcac cgtaatctgc   3000
ttgcacgtag atcacataag caccaagcgc gttggcctca tgcttgagga gattgatgag   3060
cgcggtggca atgccctgcc tccggtgctc gccggagact gcgagatcat agatatagat   3120
ctcactacgc ggctgctcaa acctgggcag aacgtaagcc gcgagagcgc caacaaccgc   3180
```

-continued

| | | | | | |
|---|---|---|---|---|---|
| ttcttggtcg | aaggcagcaa | gcgcgatgaa | tgtcttacta | cggagcaagt | tcccgaggta | 3240 |
| atcggagtcc | ggctgatgtt | gggagtaggt | ggctacgtct | ccgaactcac | gaccgaaaag | 3300 |
| atcaagagca | gcccgcatgg | atttgacttg | gtcagggccg | agcctacatg | tgcgaatgat | 3360 |
| gcccatactt | gagccaccta | actttgtttt | agggcgactg | ccctgctgcg | taacatcgtt | 3420 |
| gctgctgcgt | aacatcgttg | ctgctccata | acatcaaaca | tcgacccacg | gcgtaacgcg | 3480 |
| cttgctgctt | ggatgcccga | ggcatagact | gtacaaaaaa | acagtcataa | caagccatga | 3540 |
| aaaccgccac | tgcgccgtta | ccaccgctgc | gttcggtcaa | ggttctggac | cagttgcgtg | 3600 |
| agcgcatacg | ctacttgcat | tacagtttac | gaaccgaaca | ggcttatgtc | aactgggttc | 3660 |
| gtgccttcat | ccgtttccac | ggtgtgcgtc | acccggcaac | cttgggcagc | agcgaagtcg | 3720 |
| aggcatttct | gtcctggctg | gcgaacgagc | gcaaggtttc | ggtctccacg | catcgtcagg | 3780 |
| cattggcggc | cttgctgttc | ttctacggca | aggtgctgtg | cacggatctg | ccctggcttc | 3840 |
| aggagatcgg | tagacctcgg | ccgtcgcggc | gcttgccggt | ggtgctgacc | ccggatgaag | 3900 |
| tggttcgcat | cctcggtttt | ctggaaggcg | agcatcgttt | gttcgcccag | gactctagct | 3960 |
| atagttctag | tggttggcct | acgtacccgt | agtggctatg | gcagggcttg | ccgccccgac | 4020 |
| gttggctgcg | agccctgggc | cttcacccga | acttgggggg | tggggtgggg | aaaaggaaga | 4080 |
| aacgcgggcg | tattggtccc | aatggggtct | cggtggggta | tcgacagagt | gccagccctg | 4140 |
| ggaccgaacc | ccgcgtttat | gaacaaacga | cccaacaccc | gtgcgtttta | ttctgtctt | 4200 |
| ttattgccgt | catagcgcgg | gttccttccg | gtattgtctc | cttccgtgtt | tcagttagcc | 4260 |
| tcccccatct | cccggtaccg | catgctatgc | atcagctggc | acgacaggtt | tcccgactgg | 4320 |
| aaagcgggca | gtgagcgcaa | cgcaattaat | gtgagttagc | tcactcatta | ggcacccag | 4380 |
| gctttacact | ttatgcttcc | ggctcgtatg | ttgtgtggaa | ttgtgagcgg | ataacaattt | 4440 |
| cacacaggaa | acagctatga | ccatgattac | gccaagcttg | catgcaggcc | tctgcagtcg | 4500 |
| acgggcccgg | gatccgatga | cccaatacta | gtttagttga | actcgaactt | cttgtacttg | 4560 |
| cagttgagct | tttgctcggc | gaatgtgatg | gcgtcggaga | gtggcaccag | tccctgcagg | 4620 |
| atcaaggcca | agagcttcag | caagttgttg | tgcagtgtag | ttgactcgcg | acggttgacc | 4680 |
| ttgccgatca | cgaacatgtg | gtgcttgaat | ctgttgtact | tttggatgac | ctggctcaca | 4740 |
| tcaacgtcct | tgatttcgcc | agagatccag | tagaactcct | tgttcttctt | agcgatggtc | 4800 |
| agccttttcct | cgttcttgaa | ggacaacacg | atgaagttgt | gacccttaac | gttatcgacg | 4860 |
| ttttgagtca | agtactgctc | aacgatgtgc | atgcttccgt | cttccttctt | gaccttcttg | 4920 |
| aggttctcgg | cgttgttgtt | agaagcgatg | ttgtcgtggt | acttgtagtt | gttgaagagc | 4980 |
| aggttagcga | cggacgagta | cttgtatgtc | agagtgctct | tcttgttcac | gatgaggttc | 5040 |
| aggttatcaa | cgacgtactt | gttgggaggg | ttgtccggga | attggacgga | ctccgagtac | 5100 |
| ttgaggatct | gggaaacgta | tggcgagacg | aagaagttgt | tagaggcggt | ttcgatctcg | 5160 |
| tttgattcct | tgcggctcag | catgatgggc | aaagtgaaga | ggttcttgtc | ctggtacatc | 5220 |
| tcgtacaact | tcgacaagag | gaatccacac | ttacgctcgc | cgagtgattg | cagcaaggtc | 5280 |
| acgaaggttg | tctgagcgta | gtacatatcg | aggttgaagt | aggaggtcag | agcggccttg | 5340 |
| aatgtgtggt | ggacgtccac | gaagtgacac | ttcttgcagt | tttgagcggc | ggtctcatcg | 5400 |
| ttgcagacgt | cctgtgagtg | tgggatttcg | atgccagtct | ccttaaccag | gttgtagctg | 5460 |
| atcatgaagc | ggatcttatc | gaaggtcaca | acgaacacac | ggttgtcaac | catgtagtag | 5520 |
| ttgtttgtgt | actcgtagac | cacgttagag | acgtacttgg | cgaagatgat | ttcgaaaggc | 5580 |

```
ttcacctcgg acttcttaac gacgaacatg tagtaaccgg tttcagacat gtgatcggag    5640
aatctgttcg agttgtagtc gttatcgtcg aacctcatca ggtaggggc gaagtcgttt     5700 gtgaagtagt gagtgatctc ctgggtggaa gccactgtac agatgttagt gttgtggttg    5760
atggtttgtt ccagtgtagc gcatgactgg atggtgctct tcttgtactt aggtctcaac    5820
ttgatcttgt tgaattgacc cacaactccc tgggagttat ccaggtactc gtccaacttc    5880
ctcttggtgc ctgtggccga cggctggttg acaccagcag agtgttcgaa ggactcggcg    5940
tggtaagctg agctaggaga gggttgttcg accactggct gttcgagtga ctcgctgtag    6000
taggcagagg acacagcttc ctccaggttg tcagtggtct tgagcagaca ctccaccaaa    6060
tcgttgtcag tgagcgagtt aactgaggcg aggaagttgc tagcggcagc ggtttcagag    6120
tcggagatga cagtatcagc tccgtccggg gttgggtggt tgtagtaaga caagtaatcg    6180
ttaggttgct tgtcgcagaa ctccgagtat gagttgtcga agctagcacg agagggagtg    6240
ctggcagagg tgtaggaagc gttgaagttg atttgagtca tggtgacctg gttgttcacg    6300
atcttatcgc cacctgtgtc cacctgcagt tgctgggcct cagcgcaggc tgaagtggcc    6360
tcacaggagt aggggctgga agcacagttg gaagtcatga tgttttcttg gacgttcagg    6420
acgtggctgg atgtacggat catagatcta tctagattcg aaagcggccg cgactagtga    6480
gctcgtcgac gtaggccttt gaattccgcg cgcttcggac cgggatccgc gcccgatggt    6540
gggacggtat gaataatccg gaatatttat aggttttttt attacaaaac tgttacgaaa    6600
acagtaaaat acttatttat ttgcgagatg gttatcattt taattatctc catgatctat    6660
taatattccg gagtatacct acccgtaaag cgagtttagt tttgaaaaac aaatgacatc    6720
atttgtataa tgacatcatc ccctgattgt gttttacaag tagaattcta tccgtaaagc    6780
gagttcagtt ttgaaaacaa atgagtcata cctaaacacg ttaataatct tctgatatca    6840
gcttatgact caagttatga gccgtgtgca aaacatgaga taagtttatg acatcatcca    6900
ctgatcgtgc gttacaagta gaattctact cgtaaagcca gttcggttat gagccgtgtg    6960
caaaacatga catcagctta tgactcatac ttgattgtgt tttacgcgta gaattctact    7020
cgtaaagcga gttcggttat gagccgtgtg caaaacatga catcagctta tgagtcataa    7080
ttaatcgtgc gttacaagta gaattctact cgtaaagcga gttgaaggat catatttagt    7140
tgcgtttatg agataagatt gaaagcacgt gtaaaatgtt tccgagctcg tcgacgtagg    7200
cctttgaatt ccgcgcgctt cggaccggga tcggtaccaa attccgtttt gcgacgatgc    7260 agagttttg aacaggctgc tcaaacacat agatccgtac ccgctcagtc ggatgtatta    7320
caatgcagcc ataccatgt tttacacgac tatggaaaac tatgccgtgt ccaattgcaa     7380
gttcaacatt gaggattaca ataacatatt taaggtgatg gaaatatta ggaaacacag     7440 caacaaaaat tcaaacgacc aagacgagtt aaacatatat ttgggagttc agtcgtcgaa    7500
tgcaaagcgt aaaaaatatt aataaggtaa aaattacagc tacataaatt acacaattta    7560
aactgcagtc tggagatacg gacctttaat tcaacccaac acaatatatt atagttaaat    7620
aagaattatt atcaaatcat ttgtatatta attaaaatac tatactgtaa attacatttt    7680
atttacaatc actcgacctc gacatgaaat tcttagtcaa cgttgccctt gttttatgg    7740 tcgtatacat ttcttacatc tatgcggatc ctgacacaat atgtataggc taccatgcga    7800
acaattcaac cgacactgtt gacacagtac tcgagaagaa tgtgacagtg acacactctg    7860
ttaacctgct cgaagacagc cacaacggaa aactatgtag attaaaagga atagccccac    7920
```

```
tacaattggg gaaatgtaac atcgccggat ggctcttggg aaacccagaa tgcgacccac    7980
tgcttccagt gagatcatgg tcctacattg tagaaacacc aaactctgag aatggaatat    8040
gttatccagg agatttcatc gactatgagg agctgaggga gcaattgagc tcagtgtcat    8100
cattcgaaag attcgaaata tttcccaaag aaagctcatg gcccaaccac aacacaaacg    8160
gagtaacggc agcatgctcc catgagggga aaagcagttt ttacagaaat ttgctatggc    8220
tgacggagaa ggagggctca tacccaaagc tgaaaaattc ttatgtgaac aaaaaaggga    8280
aagaagtcct tgtactgtgg ggtattcatc acccgcctaa cagtaaggaa caacagaatc    8340
tctatcagaa tgaaaatgct tatgtctctg tagtgacttc aaattataac aggagattta    8400
ccccggaaat agcagaaaga cccaaagtaa gagatcaagc tgggaggatg aactattact    8460
ggaccttgct aaaccccgga gacacaataa tatttgaggc aaatggaaat ctaatagcac    8520
caatgtatgc tttcgcactg agtagaggct ttgggtccgg catcatcacc tcaaacgcat    8580
caatgcatga gtgtaacacg aagtgtcaaa caccccctggg agctataaac agcagtctcc    8640
cttaccagaa tatacaccca gtcacaatag gagagtgccc aaaatacgtc aggagtgcca    8700
aattgaggat ggttacagga ctaaggaaca ctccgtccat tcaatccaga ggtctatttg    8760
gagccattgc cggtttttatt gaaggggat ggactggaat gatagatgga tggtatggtt    8820
atcatcatca gaatgaacag ggatcaggct atgcagcgga tcaaaaaagc acacaaaatg    8880
ccattaacgg gattacaaac aaggtgaaca ctgttatcga gaaatgaac attcaattca    8940 cagctgtggg taaagaattc aacaaattag aaaaaggat ggaaaattta aataaaaaag    9000
ttgatgatgg atttctggac atttggacat ataatgcaga attgttagtt ctactggaaa    9060
atgaaaggac tctggatttc catgactcaa atgtgaagaa tctgtatgag aaagtaaaaa    9120
gccaattaaa gaataatgcc aaagaaatcg gaaatggatg ttttgagttc taccacaagt    9180
gtgacaatga atgcatggaa agtgtaagaa atgggactta tgattatccc aaatattcag    9240
aagagtcaaa gttgaacagg gaaaaggtag atggagtgaa attggaatca atggggatct    9300
atcagatttc tagacatcac caccaccatc actaaccatg gaagcttatg aatcgttttt    9360
aaaataacaa atcaattgtt ttataatatt cgtacgattc tttgattatg taataaaatg    9420
tgatcattag gaagattacg aaaaatataa aaaatatgag ttctgtgtgt ataacaaatg    9480
ctgtaaacgc cacaattgtg tttgttgcaa ataaacccat gattatttga ttaaaattgt    9540 tgttttctt gttcatagac aatagtgtgt tttgcctaaa cgtgtactgc ataaactcca    9600
tgcgagtgta tagcgagcta gtggctaacg cttgccccac caaagtagat tcgtcaaaat    9660
cctcaatttc atcaccctcc tccaagttta acatttggcc gtcggaatta acttctaaag    9720
atgccacata atctaataaa tgaaatagag attcaaacgt ggcgtcatcg tccgtttcga    9780
ccatttccga aaagaactcg ggcataaact ctatgatttc tctggacgtg gtgttgtcga    9840
aactctcaaa gtacgcagtc aggaacgtgc gcgacatgtc gtcgggaaac tcgcgcggaa    9900
acatgttgtt gtaaccgaac gggtcccata gcgccaaaac caaatctgcc agcgtcaata    9960
gaatgagcac gatgccgaca atggagctgg cttggatagc gattcgagtt aacctaggag    10020
atccgaacca gataagtgaa atctagttcc aaactatttt gtcattttta attttcgtat    10080
tagcttacga cgctacaccc agttcccatc tattttgtca ctcttcccta aataatcctt    10140
aaaaactcca tttccacccc tcccagttcc caactatttt gtccgccac agcggggcat    10200 ttttcttcct gttatgtttt taatcaaaca tcctgccaac tccatgtgac aaaccgtcat    10260
cttcggctac ttt                                                       10273
```

<210> SEQ ID NO 32
<211> LENGTH: 2074
<212> TYPE: DNA
<213> ORGANISM: Rabbit hemorrhagic disease virus AST789

<400> SEQUENCE: 32

| | | | | | | |
|---|---|---|---|---|---|---|
| atggagggca | aagcccgcac | agcgccgcaa | ggcgaagcag | caggcactgc | caccacagca | 60 |
| tcagtccctg | gaaccacaac | cgatggcatg | daccccggcg | ttgtggccac | taccagcgtg | 120 |
| gtcactgcag | agaattcatc | cgcatcgatt | gcaacggcag | ggattggcgg | accaccccaa | 180 |
| caggtggacc | aacaagagac | atggagaacg | aactttatt | ataatgacgt | tttcacttgg | 240 |
| tcagtcgcgg | atgcccctgg | cagcatactt | tacaccgttc | aacattctcc | acagaacaac | 300 |
| ccattcacag | ccgtgctgag | ccagatgtat | gctggctggg | ctggtggcat | gcagtttcgc | 360 |
| ttcatagttg | ccggatcggg | tgtgtttggt | gggcggttgg | ttgcggccgt | gataccaccg | 420 |
| ggcatcgaga | ttggaccagg | gctggaggtc | aggcaattcc | cccatgttgt | catcgacgct | 480 |
| cgttcacttg | aacctgtcac | catcaccatg | ccagacttgc | gtcccaacat | gtaccatcca | 540 |
| actggtgacc | ctggccttgt | tcccacacta | gtccttagtg | tttataacaa | cctcatcaac | 600 |
| ccgtttggtg | ggtccaccag | cgcaatccag | gtgacagtgg | aaacaaggcc | aagtgaagat | 660 |
| tttgagttcg | tgatgattcg | agcccctcc | agcaagactg | ttgactcaat | ttcacccgca | 720 |
| ggcctcctca | cgaccccagt | cctcactggg | gttggcaatg | acaacaggtg | gaatggccaa | 780 |
| atagtgggac | tgcaaccagt | acctggaggg | ttctctacgt | gcaacaggca | ttggaacttg | 840 |
| aatggcagca | catatggctg | gtcaagcccc | cggtttgccg | acattgacca | tcgaagaggc | 900 |
| agtgcaagtt | accctggatc | caacgcaacc | aacgtgcttc | agttttggta | tgccaatgct | 960 |
| gggtctgcaa | tcgacaatcc | catctcccag | gttgcaccag | acggctttcc | tgatatgtcg | 1020 |
| ttcgtgccct | ttaacggccc | tggcattcca | gccgcggggt | gggtcggatt | tggtgcaatc | 1080 |
| tggaacagta | acagcggtgc | ccccaacgtt | acgactgtgc | aggcttatga | gttaggtttt | 1140 |
| gccactgggg | caccaggcaa | cctccagccc | accaccaaca | cttcaggttc | acagactgtc | 1200 |
| gccaagtcca | tatatgccgt | ggtaactggc | acagcccaaa | accccgccgg | attgtttgtg | 1260 |
| atggcctcgg | gtgttatctc | caccccaagt | gccaacgcca | tcacatacac | gccccaacca | 1320 |
| gacagaattg | taaccacacc | cggcactcct | gccgctgcac | ctgtgggtaa | gaacacaccc | 1380 |
| atcatgttcg | cgtctgtcgt | caggcgcacc | ggtgacgtca | acgccacagc | tgggtcagct | 1440 |
| aacgggaccc | agtacggcac | aggctctcaa | ccactgccag | taacaattgg | actttcgctc | 1500 |
| aacaactact | cgtcagcact | tatgcccgga | cagtttttcg | tttggcagtt | aacctttgca | 1560 |
| tctggtttca | tggagattgg | tttaagtgtg | gacgggtatt | tttatgcagg | aacaggagcc | 1620 |
| tcaaccacac | tcattgactt | gactgaactc | attgacgtac | gccctgtggg | acccaggcca | 1680 |
| tccaagagca | cactcgtgtt | caacctgggg | ggcacagcca | atggcttttc | ttatgtctga | 1740 |
| attcatcgga | ctgggacttg | caggtgccag | cgttttgagc | aatgcattgc | tccgcaggca | 1800 |
| agagctgcaa | ctacaaagac | aagctttgga | gaatggggtg | gttttgaaag | ccgaccaatt | 1860 |
| aggtaggtta | ggttttaatc | caaatgaagt | taagaatgtg | attgtaggta | atagtttag | 1920 |
| tagtaatgtt | agattaagta | atatgcataa | tgatgctagt | gtagttaatg | cttataatgt | 1980 |
| gtataatcct | gccagcaatg | gcatcagaaa | gaaaattaag | agtttgaata | atagtgttaa | 2040 |
| gatttataac | accactgggg | agtccagtgt | ttaa | | | 2074 |

<210> SEQ ID NO 33
<211> LENGTH: 1740
<212> TYPE: DNA
<213> ORGANISM: Rabbit hemorrhagic disease virus N11

<400> SEQUENCE: 33

```
atggagggta aagccagaac ggcgtcgcaa ggagaaaccg caggaacagc tacaaccgca      60
agcgtgccag gaacaacaac cgatggaatg gaccctggtg tggtggcaac cacttccgtt     120
gtgacaacgg agaacgcatc tacctcaatc gccactgcag gaattggtgg ccctccccag     180
caagtggatc agcaagaaac atggaggacg aacttctact acaacgacgt tttcacctgg     240
agcgtggcgg atgctcctgg taacatcctg tacaccgtgc agcactcgcc tcaaaacaac     300
cccttcactg ctgtcctctc ccagatgtac gccggctggg caggtggtat gcaattcagg     360
ttcatcgtcg ccggttcagg cgttttcggc ggaagactcg tggctgccgt cattccaccg     420
ggcatcgaga ttggaccggg tttggaagtg aggcagttcc cacacgtcgt tatcgacgcc     480
agatccctgg agcctgtcac aattacgatg ccagatttgc gcccgaacat gtaccatcct     540
accggcaacc ccggattggt cccaactttg gttctgtcag tgtacaacaa cctgatcaac     600
cccttcggtg gcagtacctc ggctattcag gttaccgtgg agactcgccc tagtgaggac     660
ttcgaattcg tcatgatccg tgccccctcc agcaagactg ttgactccat tagcccggca     720
gatctgctca ccactcctgt gttgacaggc gtcgaacgg ataaccgctg gaacggagaa      780
atcgtgggtc tgcagcctgt ccccggaggt ttcagcacat gcaaccgtca ctggaacctc     840
aacggctcta ccttcggatg gtcttcacca cgcttgcag cgatcgacca tgatcgtggt      900
aacgctagct accctggcag ttcgtccagc aacgtgctgg agttgtggta cgcctctgca     960
ggttcagctg ccgacaaccc catctctcag attgctccgg acggtttccc tgatatgtcc    1020
ttcgtcccct tcagcggcac aacggtgcca acagctggtt gggtcggctt cggcggaatc    1080
tggaactctt caaacggagc gcccttcgtc accactgttc aagcttacga actgggtttc    1140
gcgactggcg ctccatcaaa cccacagccg acaacgacca ctagtggtgc ccaaatcgtt    1200
gcaaagtcga tttacggagt ggctacaggt atcaaccagg cgacggctgg actgttcgtt    1260
atggcgagtg gtgtgatctc gaccoctaac agttcggcta ttacctacac tcctcaaccc    1320
aacaggatcg tgaacgcacc aggaacacct gcagctgctc ccatcggaaa aaacacgcca    1380
attatgttcg cttccgtggt ccgccgtact ggcgacatca acgccgaagc aggctctaca    1440
aacggaacgc agtacggtgc tggctcacaa ccactgccgg tcacagttgg actgagtctc    1500
aacaactact ccagcgctct gatgccagga cagttcttcg tgtggcaact caacttcgct    1560
tccggtttca tggagttggg cctgagcgtc gacggatact tctacgccgg aaccggtgcg    1620
tctgctactc tcatcgactt gtcagaactg gtcgatatta ggcctgttgg tcctagaccc    1680
agcacgagca ctctggtcta caacttgggc ggcactacta acggattctc atacgtctaa    1740
```

<210> SEQ ID NO 34
<211> LENGTH: 5249
<212> TYPE: DNA
<213> ORGANISM: Artificial sequence
<220> FEATURE:
<223> OTHER INFORMATION: polhAc-ie-01/hr1p6.9p10CVP60 G1 (AST89)

<400> SEQUENCE: 34

```
agttgaactc gaacttcttg tacttgcagt tgagcttttg ctcggcgaat gtgatggcgt      60
cggagagtgg caccagtccc tgcaggatca aggccaagag cttcagcaag ttgttgtgca     120
```

```
gtgtagttga ctcgcgacgg ttgaccttgc cgatcacgaa catgtggtgc ttgaatctgt    180
tgtacttttg gatgacctgg ctcacatcaa cgtccttgat ttcgccagag atccagtaga    240
actccttgtt cttcttagcg atggtcagcc tttcctcgtt cttgaaggac aacacgatga    300
agttgtgacc cttaacgtta tcgacgtttt gagtcaagta ctgctcaacg atgtgcatgc    360
ttccgtcttc cttcttgacc ttcttgaggt tctcggcgtt gttgttagaa gcgatgttgt    420
cgtggtactt gtagttgttg aagagcaggt tagcgacgga cgagtacttg tatgtcagag    480
tgctcttctt gttcacgatg aggttcaggt tatcaacgac gtacttgttg ggagggttgt    540
ccgggaattg gacggactcc gagtacttga ggatctggga aacgtatggc gagacgaaga    600
agttgttaga ggcggtttcg atctcgtttg attccttgcg gctcagcatg atgggcaaag    660
tgaagaggtt cttgtcctgg tacatctcgt acaacttcga caagaggaat ccacacttac    720
gctcgccgag tgattgcagc aaggtcacga aggttgtctg agcgtagtac atatcgaggt    780
tgaagtagga ggtcagagcg gccttgaatg tgtggtggac gtccacgaag tgacacttct    840
tgcagttttg agcggcggtc tcatcgttgc agacgtcctg tgagtgtggg atttcgatgc    900
cagtctcctt aaccaggttg tagctgatca tgaagcggat cttatcgaag gtcacaacga    960
acacacggtt gtcaaccatg tagtagttgt ttgtgtactc gtagaccacg ttagagacgt   1020
acttggcgaa gatgatttcg aaaggcttca cctcggactt cttaacgacg aacatgtagt   1080
aaccggtttc agacatgtga tcggagaatc tgttcgagtt gtagtcgtta tcgtcgaacc   1140
tcatcaggta gggggcgaag tcgtttgtga agtagtgagt gatctcctgg gtggaagcca   1200
ctgtacagat gttagtgttg tggttgatgg tttgttccag tgtagcgcat gactggatgg   1260
tgctcttctt gtacttaggt ctcaacttga tcttgttgaa ttgacccaca actccctggg   1320
agttatccag gtactcgtcc aacttcctct tggtgcctgt ggccgacggc tggttgacac   1380
cagcagagtg ttcgaaggac tcggcgtggt aagctgagct aggagagggt tgttcgacca   1440
ctggctgttc gagtgactcg ctgtagtagg cagaggacac agcttcctcc aggttgtcag   1500
tggtcttgag cagacactcc accaaatcgt tgtcagtgag cgagttaact gaggcgagga   1560
agttgctagc ggcagcggtt tcagagtcgg agatgacagt atcagctccg tccggggttg   1620
ggtggttgta gtaagacaag taatcgttag gttgcttgtc gcagaactcc gagtatgagt   1680
tgtcgaagct agcacgagag ggagtgctgg cagaggtgta ggaagcgttg aagttgatttt  1740 gagtcatggt gacctggttg ttcacgatct tatcgccacc tgtgtccacc tgcagttgct   1800
gggcctcagc gcaggctgaa gtggcctcac aggagtaggg gctggaagca cagttggaag   1860
tcatgatgtt ttcttggacg ttcaggacgt ggctggatgt acggatcata gatctatcta   1920
gattcgaaag cggccgcgac tagtgagctc gtcgacgtag gcctttgaat tccgcgcgct   1980
tcggaccggg atccgcgccc gatggtggga cggtatgaat aatccggaat atttataggt   2040
tttttattta caaaactgtt acgaaaacag taaaatactt atttatttgc gagatggtta   2100
tcattttaat tatctccatg atctattaat attccggagt atacctaccc gtaaagcgag   2160
tttagttttg aaaacaaat gacatcattt gtataatgac atcatcccct gattgtgttt    2220
tacaagtaga attctatccg taaagcgagt tcagttttga aaacaaatga gtcataccta   2280
aacacgttaa taatcttctg atatcagctt atgactcaag ttatgagccg tgtgcaaaac   2340
atgagataag tttatgacat catccactga tcgtgcgtta caagtagaat tctactcgta   2400
aagccagttc ggttatgagc cgtgtgcaaa acatgacatc agcttatgac tcatacttga   2460
```

-continued

```
ttgtgtttta cgcgtagaat tctactcgta aagcgagttc ggttatgagc cgtgtgcaaa    2520
acatgacatc agcttatgag tcataattaa tcgtgcgtta caagtagaat tctactcgta    2580
aagcgagttg aaggatcata tttagttgcg tttatgagat aagattgaaa gcacgtgtaa    2640
aatgtttccg agctcgtcga cgtaggcctt tgaattccgc gcgcttcgga ccgggatcgg    2700
taccaaattc cgttttgcga cgatgcagag tttttgaaca ggctgctcaa acacatagat    2760
ccgtacccgc tcagtcggat gtattacaat gcagccaata ccatgtttta cacgactatg    2820
gaaaactatg ccgtgtccaa ttgcaagttc aacattgagg attacaataa catatttaag    2880
gtgatggaaa atattaggaa acacagcaac aaaaattcaa acgaccaaga cgagttaaac    2940
atatatttgg gagttcagtc gtcgaatgca aagcgtaaaa aatattaata aggtaaaaat    3000
tacagctaca taattacac aatttaaact gcagtctgga gatacggacc tttaattcaa     3060
cccaacacaa tatattatag ttaaataaga attattatca aatcatttgt atattaatta    3120
aaatactata ctgtaaatta cattttattt acaatcactc gacctcgaga taaatatgga    3180
gggcaaagcc cgcacagcgc cgcaaggcga agcagcaggc actgccacca cagcatcagt    3240
ccctggaacc acaaccgatg gcatggaccc cggcgttgtg ccactacca gcgtggtcac      3300 tgcagagaat tcatccgcat cgattgcaac ggcagggatt ggcggaccac cccaacaggt    3360
ggaccaacaa gagacatgga gaacgaactt ttattataat gacgttttca cttggtcagt    3420
cgcggatgcc cctggcagca tactttacac cgttcaacat tctccacaga acaacccatt    3480
cacagccgtg ctgagccaga tgtatgctgg ctgggctggt ggcatgcagt ttcgcttcat    3540
agttgccgga tcgggtgtgt ttggtgggcg gttggttgcg ccgtgatac caccgggcat     3600 cgagattgga ccagggctgg aggtcaggca attcccccat gttgtcatcg acgctcgttc    3660
acttgaacct gtcaccatca ccatgccaga cttgcgtccc aacatgtacc atccaactgg    3720
tgaccctggc cttgttccca cactagtcct tagtgtttat aacaacctca tcaacccgtt    3780
tggtgggtcc accagcgcaa tccaggtgac agtggaaaca aggccaagtg aagattttga    3840
gttcgtgatg attcgagccc cctccagcaa gactgttgac tcaatttcac ccgcaggcct    3900
cctcacgacc ccagtcctca ctggggttgg caatgacaac aggtggaatg ccaaatagt    3960 gggactgcaa ccagtacctg gagggttctc tacgtgcaac aggcattgga acttgaatgg    4020
cagcacatat ggctggtcaa gccccccggtt gccgacatt gaccatcgaa gaggcagtgc    4080
aagttaccct ggatccaacg caaccaacgt gcttcagttt tggtatgcca atgctgggtc    4140
tgcaatcgac aatcccatct cccaggttgc accagacggc tttcctgata tgtcgttcgt    4200 gcccttaac ggccctggca ttccagccgc ggggtgggtc ggatttggtg caatctggaa     4260
cagtaacagc ggtgccccca acgttacgac tgtgcaggct tatgagttag gttttgccac    4320
tggggcacca ggcaacctcc agcccaccac caacacttca ggttcacaga ctgtcgccaa    4380
gtccatatat gccgtggtaa ctggcacagc ccaaaacccc gccggattgt ttgtgatggc    4440
ctcgggtgtt atctccaccc caagtgccaa cgccatcaca tacacgcccc aaccagacag    4500
aattgtaacc acacccggca ctcctgccgc tgcacctgtg ggtaagaaca cacccatcat    4560
gttcgcgtct gtcgtcaggc gcaccggtga cgtcaacgcc acagctgggt cagctaacgg    4620
gacccagtac ggcacaggct ctcaaccact gccagtaaca attggactt cgctcaacaa     4680 ctactcgtca gcacttatgc ccggacagtt tttcgtttgg cagttaacct ttgcatctgg    4740
tttcatggag attggtttaa gtgtggacgg gtatttttat gcaggaacag gagcctcaac    4800
cacactcatt gacttgactg aactcattga cgtacgccct gtgggaccca ggccatccaa    4860
```

-continued

| | |
|---|---|
| gagcacactc gtgttcaacc tgggggcac agccaatggc ttttcttatg tctgaattca | 4920 |
| tcggactggg acttgcaggt gccagcgttt tgagcaatgc attgctccgc aggcaagagc | 4980 |
| tgcaactaca aagacaagct tggagaatg ggttggtttt gaaagccgac caattaggta | 5040 |
| ggttaggttt taatccaaat gaagttaaga atgtgattga aggtaatagt tttagtagta | 5100 |
| atgttagatt aagtaatatg cataatgatg ctagtgtagt taatgcttat aatgtgtata | 5160 |
| atcctgccag caatggcatc agaaagaaaa ttaagagttt gaataatagt gttaagattt | 5220 |
| ataacaccac tggggagtcc agtgtttaa | 5249 |

<210> SEQ ID NO 35
<211> LENGTH: 4918
<212> TYPE: DNA
<213> ORGANISM: Artificial sequence
<220> FEATURE:
<223> OTHER INFORMATION: polhAc-ie-01/hr1p6.9p10CVP60 RHDVb (N11)

<400> SEQUENCE: 35

| | |
|---|---|
| agttgaactc gaacttcttg tacttgcag

```
ggtggttgta gtaagacaag taatcgttag gttgcttgtc gcagaactcc gagtatgagt    1680
tgtcgaagct agcacgagag ggagtgctgg cagaggtgta ggaagcgttg aagttgattt    1740
gagtcatggt gacctggttg ttcacgatct tatcgccacc tgtgtccacc tgcagttgct    1800
gggcctcagc gcaggctgaa gtggcctcac aggagtaggg gctggaagca cagttggaag    1860
tcatgatgtt ttcttggacg ttcaggacgt ggctggatgt acggatcata gatctatcta    1920
gattcgaaag cggccgcgac tagtgagctc gtcgacgtag gcctttgaat tccgcgcgct    1980
tcggaccggg atccgcgccc gatggtggga cggtatgaat aatccggaat atttataggt    2040 tttttatta caaaactgtt acgaaaacag taaaatactt atttatttgc gagatggtta    2100
tcattttaat tatctccatg atctattaat attccggagt atacctaccc gtaaagcgag    2160
tttagttttg aaaacaaat gacatcattt gtaatgac atcatcccct gattgtgttt    2220
tacaagtaga attctatccg taaagcgagt tcagttttga aaacaatga gtcatacctaa   2280 aacacgttaa taatcttctg atatcagctt atgactcaag ttatgagccg tgtgcaaaac    2340
atgagataag tttatgacat catccactga tcgtgcgtta caagtagaat tctactcgta    2400
aagccagttc ggttatgagc cgtgtgcaaa acatgacatc agcttatgac tcatacttga    2460
ttgtgtttta cgcgtagaat tctactcgta aagcgagttc ggttatgagc cgtgtgcaaa    2520
acatgacatc agcttatgag tcataattaa tcgtgcgtta caagtagaat tctactcgta    2580
aagcgagttg aaggatcata tttagttgcg tttatgagat aagattgaaa gcacgtgtaa    2640
aatgtttccg agctcgtcga cgtaggcctt tgaattccgc gcgcttcgga ccgggatcgg    2700
taccaaattc cgttttgcga cgatgcgaga ttttgaaca ggctgctcaa acacatagat     2760
ccgtacccgc tcagtcggat gtattacaat gcagccaata ccatgtttta cacgactatg    2820
gaaaactatg ccgtgtccaa ttgcaagttc aacattgagg attacaataa catatttaag    2880
gtgatggaaa atattaggaa acacagcaac aaaaattcaa acgaccaaga cgagttaaac    2940
atatatttgg gagttcagtc gtcgaatgca aagcgtaaaa aatattaata aggtaaaaat    3000
tacagctaca taattacac aatttaaact gcagtctgga gatacggacc tttaattcaa     3060
cccaacacaa tatattatag ttaaataaga attattatca aatcatttgt atattaatta    3120
aaatactata ctgtaaatta cattttattt acaatcactc gacctcgaga taaatatgga    3180
gggtaaagcc agaacggcgt cgcaaggaga accgcagga acagctacaa ccgcaagcgt     3240
gccaggaaca acaaccgatg gaatggaccc tggtgtggtg gcaaccactt ccgttgtgac    3300
aacggagaac gcatctacct caatcgccac tgcaggaatt ggtggccctc cccagcaagt    3360
ggatcagcaa gaaacatgga ggacgaactt ctactacaac gacgttttca cctggagcgt    3420
ggcggatgct cctggtaaca tcctgtacac cgtcagcac tcgcctcaaa acaaccctt      3480 cactgctgtc ctctcccaga tgtacgccgg ctgggcaggt ggtatgcaat tcaggttcat    3540
cgtcgccggt tcaggcgttt tcggcggaag actcgtggct gccgtcattc caccgggcat    3600
cgagattgga ccgggtttgg aagtgaggca gttcccacac gtcgttatcg acgccagatc    3660
cctggagcct gtcacaatta cgatgccaga tttgcgcccg aacatgtacc atcctaccgg    3720
caaccccgga ttggtcccaa cttggttct gtcagtgtac aacaacctga tcaaccccctt   3780 cggtggcagt acctcggcta ttcaggttac cgtggagact cgccctagtg aggacttcga    3840
attcgtcatg atccgtgccc cctccagcaa gactgttgac tccattagcc ggcagatct     3900 gctcaccact cctgtgttga caggcgtcgg aacggataac cgctggaacg gagaaatcgt    3960
gggtctgcag cctgtccccg gaggtttcag cacatgcaac cgtcactgga acctcaacgg    4020
```

```
ctctaccttc ggatggtctt caccacgctt cgcagcgatc gaccatgatc gtggtaacgc    4080
tagctaccct ggcagttcgt ccagcaacgt gctggagttg tggtacgcct ctgcaggttc    4140
agctgccgac aaccccatct ctcagattgc tccggacggt ttccctgata tgtccttcgt    4200
ccccttcagc ggcacaacgg tgccaacagc tggttgggtc ggcttcggcg aatctggaa     4260
ctcttcaaac ggagcgccct tcgtcaccac tgttcaagct tacgaactgg gtttcgcgac    4320
tggcgctcca tcaaacccac agccgacaac gaccactagt ggtgcccaaa tcgttgcaaa    4380
gtcgatttac ggagtggcta caggtatcaa ccaggcgacg gctggactgt cgttatggc     4440
gagtggtgtg atctcgaccc ctaacagttc ggctattacc tacactcctc aacccaacag    4500
gatcgtgaac gcaccaggaa cacctgcagc tgctcccatc ggaaaaaaca cgccaattat    4560
gttcgcttcc gtggtccgcc gtactggcga catcaacgcc gaagcaggct ctacaaacgg    4620
aacgcagtac ggtgctggct cacaaccact gccggtcaca gttggactga gtctcaacaa    4680
ctactccagc gctctgatgc caggacagtt cttcgtgtgg caactcaact tcgcttccgg    4740
tttcatggag ttgggcctga gcgtcgacgg atacttctac gccggaaccg tgcgtctgc     4800
tactctcatc gacttgtcag aactggtcga tattaggcct gttggtccta gacccagcac    4860
gagcactctg gtctacaact tgggcggcac tactaacgga ttctcatacg tctaataa      4918
```

<210> SEQ ID NO 36
<211> LENGTH: 579
<212> TYPE: PRT
<213> ORGANISM: Rabbit hemorrhagic disease virus AST89

<400> SEQUENCE: 36

Met Glu Gly Lys Ala Arg Thr Ala Pro Gln Gly Glu Ala Ala Gly Thr
1               5                   10                  15

Ala Thr Thr Ala Ser Val Pro Gly Thr Thr Thr Asp Gly Met Asp Pro
                20                  25                  30

Gly Val Val Ala Thr Thr Ser Val Val Thr Ala Glu Asn Ser Ser Ala
            35                  40                  45

Ser Ile Ala Thr Ala Gly Ile Gly Gly Pro Pro Gln Gln Val Asp Gln
        50                  55                  60

Gln Glu Thr Trp Arg Thr Asn Phe Tyr Tyr Asn Asp Val Phe Thr Trp
65                  70                  75                  80

Ser Val Ala Asp Ala Pro Gly Ser Ile Leu Tyr Thr Val Gln His Ser
                85                  90                  95

Pro Gln Asn Asn Pro Phe Thr Ala Val Leu Ser Gln Met Tyr Ala Gly
                100                 105                 110

Trp Ala Gly Gly Met Gln Phe Arg Phe Ile Val Ala Gly Ser Gly Val
            115                 120                 125

Phe Gly Gly Arg Leu Val Ala Ala Val Ile Pro Pro Gly Ile Glu Ile
        130                 135                 140

Gly Pro Gly Leu Glu Val Arg Gln Phe Pro His Val Val Ile Asp Ala
145                 150                 155                 160

Arg Ser Leu Glu Pro Val Thr Ile Thr Met Pro Asp Leu Arg Pro Asn
                165                 170                 175

Met Tyr His Pro Thr Gly Asp Pro Gly Leu Val Pro Thr Leu Val Leu
                180                 185                 190

Ser Val Tyr Asn Asn Leu Ile Asn Pro Phe Gly Gly Ser Thr Ser Ala
            195                 200                 205

Ile Gln Val Thr Val Glu Thr Arg Pro Ser Glu Asp Phe Glu Phe Val

```
                    210                 215                 220
Met Ile Arg Ala Pro Ser Ser Lys Thr Val Asp Ser Ile Ser Pro Ala
225                 230                 235                 240

Gly Leu Leu Thr Thr Pro Val Leu Thr Gly Val Gly Asn Asp Asn Arg
                    245                 250                 255

Trp Asn Gly Gln Ile Val Gly Leu Gln Pro Val Pro Gly Gly Phe Ser
                260                 265                 270

Thr Cys Asn Arg His Trp Asn Leu Asn Gly Ser Thr Tyr Gly Trp Ser
            275                 280                 285

Ser Pro Arg Phe Ala Asp Ile Asp His Arg Arg Gly Ser Ala Ser Tyr
        290                 295                 300

Pro Gly Ser Asn Ala Thr Asn Val Leu Gln Phe Trp Tyr Ala Asn Ala
305                 310                 315                 320

Gly Ser Ala Ile Asp Asn Pro Ile Ser Gln Val Ala Pro Asp Gly Phe
                    325                 330                 335

Pro Asp Met Ser Phe Val Pro Phe Asn Gly Pro Gly Ile Pro Ala Ala
                340                 345                 350

Gly Trp Val Gly Phe Gly Ala Ile Trp Asn Ser Asn Ser Gly Ala Pro
            355                 360                 365

Asn Val Thr Thr Val Gln Ala Tyr Glu Leu Gly Phe Ala Thr Gly Ala
        370                 375                 380

Pro Gly Asn Leu Gln Pro Thr Thr Asn Thr Ser Gly Ser Gln Thr Val
385                 390                 395                 400

Ala Lys Ser Ile Tyr Ala Val Val Thr Gly Thr Ala Gln Asn Pro Ala
                    405                 410                 415

Gly Leu Phe Val Met Ala Ser Gly Val Ile Ser Thr Pro Ser Ala Asn
                420                 425                 430

Ala Ile Thr Tyr Thr Pro Gln Pro Asp Arg Ile Val Thr Thr Pro Gly
            435                 440                 445

Thr Pro Ala Ala Pro Val Gly Lys Asn Thr Pro Ile Met Phe Ala
        450                 455                 460

Ser Val Val Arg Arg Thr Gly Asp Val Asn Ala Thr Ala Gly Ser Ala
465                 470                 475                 480

Asn Gly Thr Gln Tyr Gly Thr Gly Ser Gln Pro Leu Pro Val Thr Ile
                    485                 490                 495

Gly Leu Ser Leu Asn Asn Tyr Ser Ser Ala Leu Met Pro Gly Gln Phe
                500                 505                 510

Phe Val Trp Gln Leu Thr Phe Ala Ser Gly Phe Met Glu Ile Gly Leu
            515                 520                 525

Ser Val Asp Gly Tyr Phe Tyr Ala Gly Thr Gly Ala Ser Thr Thr Leu
        530                 535                 540

Ile Asp Leu Thr Glu Leu Ile Asp Val Arg Pro Val Gly Pro Arg Pro
545                 550                 555                 560

Ser Lys Ser Thr Leu Val Phe Asn Leu Gly Gly Thr Ala Asn Gly Phe
                    565                 570                 575

Ser Tyr Val

<210> SEQ ID NO 37
<211> LENGTH: 579
<212> TYPE: PRT
<213> ORGANISM: Rabbit hemorrhagic disease virus N11

<400> SEQUENCE: 37

Met Glu Gly Lys Ala Arg Thr Ala Ser Gln Gly Glu Thr Ala Gly Thr
```

-continued

```
1               5                   10                  15
Ala Thr Thr Ala Ser Val Pro Gly Thr Thr Asp Gly Met Asp Pro
            20                  25                  30
Gly Val Val Ala Thr Thr Ser Val Thr Thr Glu Asn Ala Ser Thr
            35                  40                  45
Ser Ile Ala Thr Ala Gly Ile Gly Gly Pro Pro Gln Gln Val Asp Gln
    50                  55                  60
Gln Glu Thr Trp Arg Thr Asn Phe Tyr Tyr Asn Asp Val Phe Thr Trp
65                  70                  75                  80
Ser Val Ala Asp Ala Pro Gly Asn Ile Leu Tyr Thr Val Gln His Ser
                85                  90                  95
Pro Gln Asn Asn Pro Phe Thr Ala Val Leu Ser Gln Met Tyr Ala Gly
                100                 105                 110
Trp Ala Gly Gly Met Gln Phe Arg Phe Ile Val Ala Gly Ser Gly Val
            115                 120                 125
Phe Gly Gly Arg Leu Val Ala Ala Val Ile Pro Pro Gly Ile Glu Ile
            130                 135                 140
Gly Pro Gly Leu Glu Val Arg Gln Phe Pro His Val Val Ile Asp Ala
145                 150                 155                 160
Arg Ser Leu Glu Pro Val Thr Ile Thr Met Pro Asp Leu Arg Pro Asn
                165                 170                 175
Met Tyr His Pro Thr Gly Asn Pro Gly Leu Val Pro Thr Leu Val Leu
                180                 185                 190
Ser Val Tyr Asn Asn Leu Ile Asn Pro Phe Gly Gly Ser Thr Ser Ala
                195                 200                 205
Ile Gln Val Thr Val Glu Thr Arg Pro Ser Glu Asp Phe Glu Phe Val
    210                 215                 220
Met Ile Arg Ala Pro Ser Ser Lys Thr Val Asp Ser Ile Ser Pro Ala
225                 230                 235                 240
Asp Leu Leu Thr Thr Pro Val Leu Thr Gly Val Gly Thr Asp Asn Arg
                245                 250                 255
Trp Asn Gly Glu Ile Val Gly Leu Gln Pro Val Pro Gly Gly Phe Ser
                260                 265                 270
Thr Cys Asn Arg His Trp Asn Leu Asn Gly Ser Thr Phe Gly Trp Ser
                275                 280                 285
Ser Pro Arg Phe Ala Ala Ile Asp His Asp Arg Gly Asn Ala Ser Tyr
            290                 295                 300
Pro Gly Ser Ser Ser Asn Val Leu Glu Leu Trp Tyr Ala Ser Ala
305                 310                 315                 320
Gly Ser Ala Ala Asp Asn Pro Ile Ser Gln Ile Ala Pro Asp Gly Phe
                325                 330                 335
Pro Asp Met Ser Phe Val Pro Phe Ser Gly Thr Val Pro Thr Ala
                340                 345                 350
Gly Trp Val Gly Phe Gly Gly Ile Trp Asn Ser Ser Asn Gly Ala Pro
            355                 360                 365
Phe Val Thr Thr Val Gln Ala Tyr Glu Leu Gly Phe Ala Thr Gly Ala
            370                 375                 380
Pro Ser Asn Pro Gln Pro Thr Thr Thr Ser Gly Ala Gln Ile Val
385                 390                 395                 400
Ala Lys Ser Ile Tyr Gly Val Ala Thr Gly Ile Asn Gln Ala Thr Ala
                405                 410                 415
Gly Leu Phe Val Met Ala Ser Gly Val Ile Ser Thr Pro Asn Ser Ser
                420                 425                 430
```

```
Ala Ile Thr Tyr Thr Pro Gln Pro Asn Arg Ile Val Asn Ala Pro Gly
        435                 440                 445

Thr Pro Ala Ala Ala Pro Ile Gly Lys Asn Thr Pro Ile Met Phe Ala
    450                 455                 460

Ser Val Val Arg Arg Thr Gly Asp Ile Asn Ala Glu Ala Gly Ser Thr
465                 470                 475                 480

Asn Gly Thr Gln Tyr Gly Ala Gly Ser Gln Pro Leu Pro Val Thr Val
                485                 490                 495

Gly Leu Ser Leu Asn Asn Tyr Ser Ser Ala Leu Met Pro Gly Gln Phe
            500                 505                 510

Phe Val Trp Gln Leu Asn Phe Ala Ser Gly Phe Met Glu Leu Gly Leu
            515                 520                 525

Ser Val Asp Gly Tyr Phe Tyr Ala Gly Thr Gly Ala Ser Ala Thr Leu
        530                 535                 540

Ile Asp Leu Ser Glu Leu Val Asp Ile Arg Pro Val Gly Pro Arg Pro
545                 550                 555                 560

Ser Thr Ser Thr Leu Val Tyr Asn Leu Gly Gly Thr Thr Asn Gly Phe
                565                 570                 575

Ser Tyr Val

<210> SEQ ID NO 38
<211> LENGTH: 3891
<212> TYPE: DNA
<213> ORGANISM: Artificial Sequence
<220> FEATURE:
<223> OTHER INFORMATION: polhAc-ie-01/hr1p6.9p10GFP

<400> SEQUENCE: 38
ttagttgaac tcgaacttct tgtacttgca gttgagcttt tgctcggcga atgtgatggc      60
gtcggagagt ggcaccagtc cctgcaggat caaggccaag agcttcagca gttgttgtg     120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg acgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg tagggggcga agtcgtttgt gaagtagtga gtgatctcct gggtggaagc   1200
```

```
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagattcgaa agcggccgcg actagtgagc tcgtcgacgt aggcctttga attccgcgcg   1980
cttcggaccg ggatccgcgc ccgatggtgg gacggtatga ataatccgga atatttatag   2040 gttttttat tacaaaactg ttacgaaaac agtaaaatac ttatttattt gcgagatggt   2100
tatcatttta attatctcca tgatctatta atattccgga gtatacctac ccgtaaagcg   2160
agtttagttt tgaaaaacaa atgacatcat ttgtataatg acatcatccc ctgattgtgt   2220
tttacaagta gaattctatc cgtaaagcga gttcagtttt gaaaacaaat gagtcatacc   2280
taaacacgtt aataatcttc tgatatcagc ttatgactca agttatgagc cgtgtgcaaa   2340
acatgagata agtttatgac atcatccact gatcgtgcgt tacaagtaga attctactcg   2400
taaagccagt tcggttatga gccgtgtgca aaacatgaca tcagcttatg actcatactt   2460
gattgtgttt tacgcgtaga attctactcg taaagcgagt tcggttatga gccgtgtgca   2520
aaacatgaca tcagcttatg agtcataatt aatcgtgcgt tacaagtaga attctactcg   2580
taaagcgagt tgaaggatca tatttagttg cgtttatgag ataagattga agcacgtgt   2640 aaaatgtttc cgagctcgtc gacgtaggcc tttgaattcc gcgcgcttcg gacccgggatc   2700 ggtaccaaat tccgtttgc gacgatgcag agtttttgaa caggctgctc aaacacatag   2760
atccgtaccc gctcagtcgg atgtattaca atgcagccaa taccatgttt tacacgacta   2820
tggaaaacta tgccgtgtcc aattgcaagt tcaacattga ggattacaat aacatattta   2880
aggtgatgga aaatattagg aaacacagca acaaaaattc aaacgaccaa gacgagttaa   2940
acatatattt gggagttcag tcgtcgaatg caaagcgtaa aaaatattaa taaggtaaaa   3000
attacagcta cataaattac acaatttaaa ctgcagtctg gagatacgga cctttaattc   3060
aacccaacac aatatattat agttaaataa gaattattat caaatcattt gtatattaat   3120
taaaatacta tactgtaaat tacattttat ttacaatcac tcgacctcga gatggtgagc   3180
aagggcgagg agctgttcac cggggtggtg cccatcctgg tcgagctgga cggcgacgta   3240
aacggccaca gttcagcgt gtccggcgag ggcgagggcg atgccaccta cggcaagctg   3300 acccctgaagt tcatctgcac caccggcaag ctgcccgtgc cctggcccac cctcgtgacc   3360
accctgacct acggcgtgca gtgcttcagc cgctacccg accacatgaa gcagcacgac   3420
ttcttcaagt ccgccatgcc cgaaggctac gtccaggagc gcaccatctt cttcaaggac   3480
gacggcaact acaagacccg cgccgaggtg aagttcgagg gcgacaccct ggtgaaccgc   3540
```

-continued

| | | | | |
|---|---|---|---|---|
| atcgagctga | agggcatcga | cttcaaggag | gacggcaaca | tcctggggca caagctggag | 3600 |
| tacaactaca | acagccacaa | cgtctatatc | atggccgaca | agcagaagaa cggcatcatg | 3660 |
| gtgaacttca | agatccgcca | caacatcgag | gacggcagcg | tgcagctcgc cgaccactac | 3720 |
| cagcagaaca | cccccatcgg | cgacggcccc | gtgctgctgc | ccgacaacca ctacctgagc | 3780 |
| acccagtccg | ccctgagcaa | agacccaaac | gagaagcgcg | atcacatggt cctgctggag | 3840 |
| ttcgtgaccg | ccgccgggat | cactctcggc | atggacgagc | tgtacaagta a | 3891 |